United States Patent
Gustincich et al.

(10) Patent No.: US 12,134,768 B2
(45) Date of Patent: Nov. 5, 2024

(54) STRUCTURAL DOMAINS OF ANTISENSE RNA MOLECULES UP-REGULATING TRANSLATION

(71) Applicant: Fondazione Istituto Italiano Di Tecnologia, Genoa (IT)

(72) Inventors: Stefano Gustincich, Trieste (IT); Silvia Zucchelli, Trieste (IT); Peter Podbevsek, Trieste (IT); Janez Plavec, Trieste (IT); Piero Carninci, Yokohama (JP); Hazuki Takahashi, Trieste (IT); Toshio Yamazaki, Trieste (IT); Takako Ohyama, Trieste (IT); Harshita Sharma, Trieste (IT)

(73) Assignee: FONDAZIONE ISTITUTO ITALIANO DI TECNOLOGIA (IT)

( * ) Notice: Subject to any disclaimer, the term of this patent is extended or adjusted under 35 U.S.C. 154(b) by 124 days.

(21) Appl. No.: 16/967,254

(22) PCT Filed: Feb. 5, 2019

(86) PCT No.: PCT/IB2019/050914
§ 371 (c)(1),
(2) Date: Aug. 4, 2020

(87) PCT Pub. No.: WO2019/150346
PCT Pub. Date: Aug. 8, 2019

(65) Prior Publication Data
US 2021/0139898 A1     May 13, 2021

(30) Foreign Application Priority Data

Feb. 5, 2018   (IT) ................ 102018000002411

(51) Int. Cl.
*C12N 15/113*     (2010.01)
*C12N 15/67*      (2006.01)
*C12Q 1/68*       (2018.01)

(52) U.S. Cl.
CPC ............ *C12N 15/113* (2013.01); *C12N 15/67* (2013.01); *C12N 2310/11* (2013.01); *C12N 2310/531* (2013.01); *C12N 2310/532* (2013.01); *C12N 2320/11* (2013.01)

(58) Field of Classification Search
None
See application file for complete search history.

(56) References Cited

U.S. PATENT DOCUMENTS

2014/0107187 A1*   4/2014   Carninci ............... C12N 15/09
                                                        435/320.1

FOREIGN PATENT DOCUMENTS

WO   2012/133947 A1   10/2012
WO   2016/070853 A1   5/2016

OTHER PUBLICATIONS

International Search Report from PCT/IB2019/050914, mailed Jun. 13, 2019, 9 pages.
Written Opinion from PCT/IB2019/050914, mailed Jun. 13, 2019, 17 pages.
Demoor et al. (1998) "Antisense Nucleic Acids Targeted To The Thymidylate Synthase (TS) MRNA Translation Start Site Stimulate TS Gene Transcription" Experimental Cell Research, Elsevier, Amsterdam, NL, vol. 243, pp. 11-21.
Hayashi et al. (2012) "Activation of prokaryotic translation by antisense oligonucleotides binding to coding region of mRNA" Biochemical and Biophysical Research Communications, vol. 429, No. 1-2, pp. 105-110, (plus supplementary data).
Heyne et al. (2009) "Lightweight comparison of RNAs based on exact sequence-structure matches" Bioinformatics, vol. 25, pp. 2095-2102.
Kawagoe-Takaki et al. (2006) "Probing the secondary structure of salmon Smal SINE RNA" Gene, vol. 365, No. 1, pp. 67-73.
Patrucco et al. (2015) "Engineering mammalian cell factories with SINEUP noncoding RNAs to improve translation of secreted proteins" GENE, vol. 569, No. 2, pp. 287-293.
Podbevsek et al. (2018) "Structural determinants of the SINE B2 element embedded in the long non-coding RNA activator of translation AS Uchl1" Scientific Reports, vol. 8, No. 1, Article 3189 (13 pages).
Schein et al. (2016) "Identification of antisense long noncoding RNAs that function as SINEUPs in human cells", Scientific Reports, vol. 6, No. 1, Article 33605 (plus supplementary material) (15 pages).
Sun et al. (2006) "Common evolutionary trends for SINE RNA structures" Trends in Genetics, vol. 23, No. 1, pp. 26-33.
Sun et al. (2018) "Dynamic Regulation of RNA Structure in Mammalian Cells" bioRxiv preprint, https://doi.org/10.1101/399386 (22 pages).
Tijerina et al. (2007) "DMS Footprinting of Structured RNAs and RNA-Protein Complexes" Nature Protocols, vol. 2, No. 10, pp. 2608-2623.
Wijmenga et al. (1998) "The use of NMR methods for conformational studies of nucleic acids" Prog. Nucl. Magn. Reson. Spectrosc., vol. 32, No. 287-387.
Zarringhalam et al. (2012) "Integrating Chemical Footprinting Data into RNA Secondary Structure Prediction" PLoS ONE, vol. 7, No. 10, Article e45160 (13 pages).

(Continued)

*Primary Examiner* — Sean McGarry
(74) *Attorney, Agent, or Firm* — McAndrews, Held & Malloy, Ltd.

(57) ABSTRACT

There are disclosed functional nucleic acid molecules comprising a target binding sequence comprising a sequence reverse complementary to a target mRNA sequence for which protein translation is to be enhanced; and a regulatory sequence having two-dimensional structures comprising specific stem-loop and internal loop domains and displaying translation enhancing efficiency.

8 Claims, 55 Drawing Sheets
Specification includes a Sequence Listing.

(56) References Cited

OTHER PUBLICATIONS

Zucchelli et al. (2015) "SINEUPs are modular antisense long non-coding RNAs that increase synthesis of target proteins in cells" Frontiers in Cellular Neuroscience, vol. 9, Article 174 (12 pages).
Zucchelli et al. (2015) "SINEUPs: A new class of natural and synthetic antisense long non-coding RNAs that activate translation" RNA Biology, vol. 12, No. 8, pp. 771-779.
Indrieri et al. (2016) "Synthetic long non-coding RNAs (SINEUPs) rescue detective gene expression in vivo", Scientific Reports, vol. 6, No. 1, Article 27315. (8 pages).

* cited by examiner

A

B

A

B

C

A

| SINE name | Length | Distribution | Sequence |
|---|---|---|---|
| ID (BC1,...) | 75 | Rat/Rodentia rodent | GGGGTGGGGATTTAGCTCAGTGGTAGAGCGCTTGCCTAGCAAGCGCAAGGCCCTGGGTTCGGTCC TCAGCTCCG |
| SB8 | 95 | Brassica/Planta brassica | GCCGGACAGAATAGCCTAGTGGTAACACTAGAGTGAACTGGATTCCAAGGCACCTGGGTTCGAGT CCTCTGGGATTCCGGAGACGCCCGTGAC |
| p-SINE1 | 115 | rice/Planta rice | GAGAAACGCCCTGGGTTCCGGTACCTCCACAAGCTGGGCTAGCGACCTGGGTTCGAA GGTCACCCCTCTAATTATTGATATAGGTCCTTCCTAATATTCGTG |
| Smal | 140 | Salmonidae/Osteichthyes salmon | GGTCCTTCGTAGCTCAGTTGGTAGAGCATGGACCTGCTGTAACGCCAGGGTAGTGGGTTCGATTCCG GGACCACCCATACGTAAAAATGTATGCACACATGACTGTAAGTTGCTTTGGATAAAAGCGTCTGCTAA ATGGC |
| SB4 | 159 | Arabidopsis/Planta arabidopsis | ACCAAGCTGCTGTGGCCAGTGGTAAATCTCCCAGGTGAAGGTGCTGGGTTCGAGGCAAGTTGGG AGGGATCTTTCCAAAGAGATGAATTTAACCTGGTGTCCCGCCTCTAGAGATGTAGGGGC CTTGGGTTTGAACTTCCAGATATTC |
| SB1 | 171 | Brassica oleracea/Planta brassica | ACCCAGGAGACCTCTAGTCCAGTGGTACTACCTCCTCTTTGGGGAGGGAGGTTGGCTGTTGAACTC GCGGGAGGGGAGGCGGTGCCCAGGGCCCTAACCGGTACAGGGCACAGGCTGGCGGCGGGGCCTAG GTGGTTGGCTGGTCGAAGGCTGGTCAACACTGGTTAATCA |
| B2 | 185 | (unclear) | (unreadable) |
| Hpa1 | 189 | Salmonidae/Salmonoidei salmon | GGGGCGGCGGCAGGGTAGCCTAGCGGTTAGAGCGTTGGACTAGTAACCGAAAGGTTGCAAGTTCAAAT CCCCGAGCTGACAAGGTACAAATCTGTGTTCGCCCTGAACAAGGCAGTTAACCACTGTTCCTA GGCCTGTCATTGAAAATAAGAATTGTTCTTAACTGACTTGCCTAGTTAAAAAGGT |
| ERE-B2 | 235 | horses/Mammalia horses | GGGGCCCAGGCCCCTGCCGTGGCCTAGTGGTTAAGTTGGCGCGTCGGTCCCTTGGGGGGCCGGGTTGGCC GGTTGGAGGCAGTGGAGCGGACTACATAACTGCTAGGGCATGCTGGCGGCGGCGATGGGATGGAATATAA AATGAGCGAAGATTGGCACGAGATGGTAGCTCAGGGACGATCTCAAGAAAAAGAGGAAGAT GGCAACAGATGTTAGCTGAGGCGAATCCTCCTGAGC |
| Ther-1 (MIR) | 252 | Vertebrata human | GCAGTGTGGCGCAGTGGATAGAGCACGGACTCGAGTCAGGAAGACCTGGTTCGAATCCGGGC TCTGCCACTTACTAGCCTGTGTGACCTTGGGCAAGTCACTTAACCTCTGTGCCTCAGTTTCCTCATCT GTAAATCGGCTTAAGACAGTGCCTGGCACTAGTAAGCGCTATAGTAAGATGTT TAAAGCGGCTTAAGACAGTGAACAGTGCCTGGCACTAGTAAGCGCTATAGTGAGATATATATG |

Negative controls: GFP o/l (without ED)
Positive control: SINEUP-GFP

44-120 SINEUP-GFP:
BD GFP -40/+4
ED invB2(44-120) (wt: 77-79 GUG)

44-120 U78G SINEUP-GFP:
BD GFP -40/+4
ED invB2(44-120) (U78G)

44-120 GUG77-79CCC SINEUP-GFP:
BD GFP -40/+4
ED invB2(44-120) (GUG77-79CCC)

B

STRUCTURAL DOMAINS OF ANTISENSE RNA MOLECULES UP-REGULATING TRANSLATION

CROSS-REFERENCE TO RELATED APPLICATIONS

This application is a National Stage Entry of International Application No. PCT/IB2019/050914 filed Feb. 5, 2019, entitled "STRUCTURAL DOMAINS OF ANTISENSE RNA MOLECULES UPREGULATING TRANSLATION" which is herein incorporated by reference in its entirety, and which claims the priority from Italian Patent Application Ser. No. 102018000002411 filed on Feb. 5, 2018 entitled "STRUCTURAL DOMAINS OF ANTISENSE RNA MOLECULES UPREGULATING TRANSLATION" which is herein incorporated by reference in its entirety.

TECHNICAL FIELD OF THE INVENTION

The present invention relates to functional nucleic acid molecules comprising a target binding sequence comprising a sequence reverse complementary to a target mRNA sequence for which protein translation is to be enhanced; and a regulatory sequence having two-dimensional structures comprising specific stem-loop and internal loop domains and/or specific three-dimensional structures.

PRIOR ART

Large genomic projects such as ENCODE and FANTOM have shown that the majority of the genome is transcribed, but less than 5% of transcribed RNA encode for proteins. Indeed, long non-coding RNAs (lncRNAs) and transposable elements (TEs) seem to represent the major cellular transcriptional output. In the past ten years, an increasing number of studies are unveiling lncRNA functions. Altogether, it is becoming evident that lncRNAs act primarily as regulatory molecules, in the nucleus and in the cytoplasm, through a wide repertoire of mechanisms. Despite this progress, only a small portion of annotated lncRNAs has been functionally validated.

Recently, a novel functional class of antisense (AS) lncRNAs was identified, which increase translation of partially overlapping sense protein-coding mRNAs. These RNAs are also called SINEUPs, as they are antisense RNAs that contain SINE elements that cause UP-regulation of protein translations.

Antisense (AS) Uchl1, a lncRNA antisense to the mouse orthologue of human Uchl1/PARK5 gene, can be considered the representative member of SINEUPs as it was found to increase UchL1 protein synthesis acting at a post-transcriptional level. AS Uchl1 activity depends on the combination of two functional domains: at the 5' end, the overlapping region, indicated as "Binding Domain", dictates AS Uchl1 specificity towards Uchl1 mRNA; at the 3' end, the non-overlapping region contains an embedded inverted SINE B2 element, which acts as "Effector Domain" and triggers translation up-regulation of bound target mRNA.

More than 30 antisense lncRNAs promote translation up-regulation of partially overlapping mRNAs. By swapping the Binding Domain, it is possible to re-direct AS Uchl1 activity towards a target mRNA of choice.

These natural and synthetic molecules were named SINEUPs, as they require a SINE B2 element to UP-regulate translation and are disclosed in WO 2012/133947. AS Uchl1 can be considered the representative member of this new class of lncRNAs, where an embedded transposable element is exploited as functional RNA domain to achieve protein up-regulation.

The inverted SINE B2 element is an example of well-defined lncRNA domain. Evolutionary studies have indicated that the primary sequences of SINE elements, like lncRNAs in general, are poorly conserved. Partial conservation within SINE elements is only observed at A and B boxes, that, in non-embedded SINEs, represent internal promoters for RNA polymerase III. Interestingly, in spite of poor sequence identity, at least murine SINE B2 elements display functional conservation as a number of SINE B2 sequences have been shown to act as effector domains in natural and chimeric SINEUPs. Also a human SINE element was identified and proved to work as SINEUP (Schein A. et al., Sci Rep. (2016), 6:33605).

Therefore, domain functionality of embedded SINE has been hypothesized to reside on structural-based rather than sequence-based motifs.

RNA folding has been hypothesized to provide the functional cues to lncRNAs and embedded TEs. RNA sequences are capable of folding to form complex secondary and tertiary structures that are difficult to predict when only the primary nucleotide sequence is known. Computational methods for systematically identifying lncRNA secondary structure modules are still unsatisfactory. Current algorithms are capable of correctly predicting about 50-70% of known base pairs. Most importantly, a value of 50-70% accuracy in the secondary structure prediction model results from the average between regions where the model is correct and regions of profound inconsistency. Therefore, measuring the actual structure of RNA molecules in solution is the only available method to gain insights into RNA functions. Methods are available based on chemical modification of water-accessible residues (chemical footprinting) and based on the magnetic features of nucleic acids (NMR). More recently, a novel biochemical approach, termed icSHAPE (in vivo click selective 29-hydroxyl acylation and profiling experiment), has been developed, which enables the first global view of RNA secondary structures in living cells for all four bases.

In view of the above, there is a need to identify whether specific two-dimensional or three-dimensional molecular structures contribute to the function of lncRNAs in order to be able to effectively and efficiently exploit these molecules in further research and in the clinical setting. In particular, lncRNAs represent an ideal tool for a broad range of research activities, from studying gene function to industrial protein production and for in vivo applications, such as treatment of haploinsufficiencies.

SUMMARY OF THE INVENTION

It is an object of the present invention to identify the secondary and tertiary structure of the inverted SINE B2 element derived from mouse AS Uchl1, of other mouse SINEs and of SINEs from evolutionary distant species that are embedded in functional antisense lncRNAs with partial overlap to a protein-coding gene and translation up-regulation activity. The identification of motifs in the secondary and tertiary structures of these molecules and their appropriate combination would allow the design of SINE elements with increased translation up-regulation function.

In addition, the identification of these motifs and their appropriate combination would allow the design of shorter functional sequences. In fact, for therapeutic applications, the delivery of SINEUP RNA is a crucial challenge. RNA molecules are highly unstable in living organisms. Chemical modifications and/or encapsulation in lipid nanoparticles have been widely used to overcome the natural instability of RNAs. However, these delivery methods have been proven inefficient for long RNA molecules. The design of shorter variants of the inverted SINE B2 effector domain retaining only discrete and active structural elements "cleans" the effector domain from "non-essential" sequences to obtain the shortest active SINEUP RNA molecule.

This object is achieved by means of the functional nucleic acid molecule as defined in claim 1.

Definitions

By the term "miniSINEUP" there is intended a nucleic acid molecule consisting of a binding domain (complementary sequence to target mRNA), a spacer sequence (in the exemplified case a 21 nt spacer), and any SINE or SINE-derived sequence as the effector domain (Zucchelli et al., Front Cell Neurosci., 9: 174, 2015.).

In particular, by the term "miniSINEUP-GFP" there is intended that the binding domain of the miniSINEUP is designed to complementary sequence to EGFP mRNA (Zucchelli et al., Front Cell Neurosci., 9: 174, 2015.).

By "functional nucleic acid molecule" there is intended generally that the nucleic acid molecule is capable of enhancing the translation of a target mRNA of interest.

BRIEF DESCRIPTION OF THE DRAWINGS

In FIG. 40 panel A: the sequence "FL" is SEQ ID NO:93, the sequence "TM" is SEQ ID NO:94, the sequence "C" is SEQ ID NO:75, and the sequence "MC2" is SEQ ID NO:77. The sequence of FIG. 40 panel C is SEQ ID NO:93.

FIG. 41 shows the structure dynamics of AS-Uchl1 SINEB2. In FIG. 41 panel A, the sequence "FL" is SEQ ID NO:93 and the sequence "C" is SEQ ID NO:75.

122" is SEQ ID NO:48, the sequence "TM" is SEQ ID NO:94, and the sequence "MC2" is SEQ ID NO:96.

Figure 49:
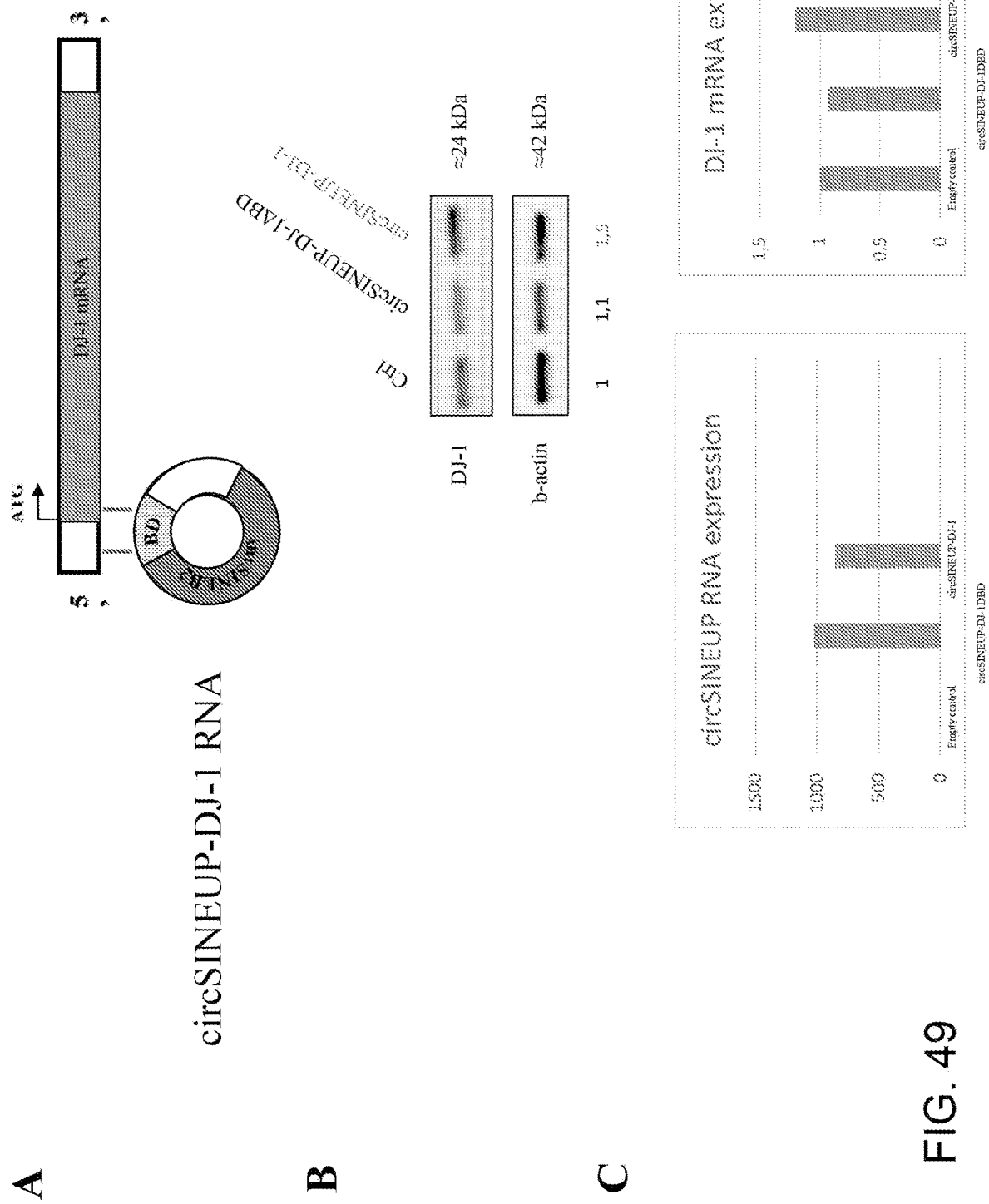

FIG. 49 related to Example 48 shows that SINEUP-DJ-1 is active when expressed as circular RNA.

DETAILED DESCRIPTION OF THE INVENTION

In the present invention, there is disclosed—among other things—the secondary and tertiary structure of inverted SINE B2 transposable element derived from AS Uchl1 as representative effector domain of SINEUPs.

Deletion mutants are used to show the structural elements required for SINEUP activity.

Further, the structure SINE B2 sequences from antisense lncRNAs with function of translation up-regulation (natural SINEUPs) is determined in living cells.

Structure-function relation is also defined based on biochemical characterization of SINEUP activity and icSHAPE profiles of active and inactive SINEs (the latter not shown).

Structure-based activity motifs of SINE B2 sequences are disclosed.

The translation up-regulation activity of functional effector domains of SINE sequences derived from evolutionary distant species whose primary sequence is not conserved and whose secondary structure elements are known is also disclosed.

In particular, functional experiments indicate that a short terminal hairpin loop structure, also referred to as the first stem-loop domain (SL-1), is the key structural determinant for the ability of SINEUPs to up-regulate translation of partially overlapping mRNAs and additional structural elements are also important for enhanced activity and discriminate those SINEs that are more active from those that are less active.

It is proved that the primary sequence of an RNA molecule does not necessarily lead to a predetermined secondary structure and that, depending on the conditions, alternative folding of the molecule can occur. In other words, the secondary structure obtained from a primary sequence of an RNA molecule is by no means predetermined and predictable only from the primary sequence.

In addition, several variants of effector domains of SINE sequences are provided which are mutated to strengthen the secondary structure and/or to limit the size of the molecule. These variants have been designed by identifying particularly relevant and conserved motifs in the secondary structure and combining them so as to arrive at the minimal structure required for function and at the optimum sequence and conditions to obtain such a structure.

Indeed, a functional nucleic acid molecule of the present invention comprises a target binding sequence comprising a sequence reverse complementary to a target mRNA sequence for which protein translation is to be enhanced, and a regulatory sequence having a two-dimensional structure comprising a first stem-loop domain (SL-1) comprising a stem with 8 to 12 paired nucleotides and a loop comprising 5 to 9 nucleotides. The regulatory sequence has protein translation enhancing efficiency.

According to the invention, it has been shown that, as long as the secondary structure is conserved, the bases of the primary sequence can vary to a large extent.

The target binding sequence needs to have only about 60% similarity with a sequence reverse complementary to the target mRNA. As a matter of fact, the target binding sequence can even display a large number of mismatches and retain activity. Indeed, miRNAs can affect their sense mRNA partners even having a large number of mismatches. This concept has already been shown in WO 2012/133947.

The target binding sequence and the regulatory sequence are preferably connected by a spacer/linker sequence.

Preferably, the stem of the first stem-loop domain (SL-1) is G/C rich, whereby by "G/C rich sequence" there is intended a sequence having more than 50% Gs and Cs, and preferably more than 75% Gs and Cs.

Preferably, the loop of the first stem-loop domain (SL1) is A/U rich, whereby by "A/U rich sequence" there is intended a sequence having more than 50% As and Us, and preferably more than 75% As and Us.

The stem of the first stem-loop domain (SL-1) preferably has 10 paired nucleotides and the loop of the first stem-loop domain (SL-1) preferably has 7 nucleotides.

A functional nucleic acid molecule of the present invention comprises a target binding sequence comprising a sequence reverse complementary to a target mRNA sequence for which protein translation is to be enhanced, and a regulatory sequence having a two-dimensional structure comprising a first stem-loop domain (SL-1) having a sequence with at least 50% identity with SEQ ID NO:1, preferably at least 75% identity with SEQ ID NO:1, more preferably at least 90% identity with SEQ ID NO:1.

In the exemplified inverted SINE B2 transposable element derived from AS Uchl1, the first stem-loop domain (SL-1) comprises SEQ ID NO:1, i.e. nucleotides 64 to 92 of SEQ ID NO:5 (the latter being the complete sequence of the inverted SINE B2 transposable element derived from AS Uchl1).

Preferably, the stem of the first stem-loop domain (SL-1) has an A-type helical three-dimensional structure, as shown by high-resolution NMR.

The two-dimensional structure of the regulatory sequence preferably further comprises a second stem-loop domain (SL-2) and a fourth internal loop domain (IL-4) or a fourth stem-loop domain (SL-4), the second stem-loop domain (SL-2) comprising a stem with 2 to 4 paired nucleotides and a loop comprising 6 to 10 nucleotides and the fourth internal loop domain (IL-4) comprising 14 to 24 nucleotides, and the fourth stem-loop domain (SL-4) comprising a stem with 3 to 5 paired nucleotides and a loop comprising 6 to 10 nucleotides.

The stem of the second stem-loop domain (SL-2) is preferably G/C rich. The loop of the second stem-loop domain (SL-2) and/or the fourth internal loop domain are/is preferably A/U rich.

The stem of the second stem-loop domain (SL-2) preferably has 3 paired nucleotides and the loop of the second stem-loop domain (SL-2) preferably has 8 nucleotides. The fourth internal loop domain (IL-4) preferably comprises 16 to 22 nucleotides.

A functional nucleic acid molecule of the present invention preferably comprises a regulatory sequence having a two-dimensional structure comprising a sequence with at least 50% identity with SEQ ID NO:2, preferably at least 75% identity with SEQ ID NO:2, more preferably at least 90% identity with SEQ ID NO:2.

In the exemplified inverted SINE B2 transposable element derived from AS Uchl1, the regulatory sequence comprises SEQ ID NO:2, i.e. nucleotides 52 to 112 of SEQ ID NO:5.

The two-dimensional structure of the regulatory sequence preferably further comprises a third internal loop domain (IL-3) comprising 6 to 14 nucleotides, preferably 7 to 13 nucleotides.

The two-dimensional structure of the regulatory sequence preferably further comprises a third stem-loop domain (SL- 3) comprising a stem with 1 to 3 paired nucleotides and a loop comprising 3 to 5 nucleotides.

The functional nucleic acid molecule of the present invention preferably comprises a regulatory sequence having a two-dimensional structure comprising a sequence with at least 50% identity with SEQ ID NO:3, preferably at least 75% identity with SEQ ID NO:3, more preferably at least 90% identity with SEQ ID NO:3.

In the exemplified inverted SINE B2 transposable element derived from AS Uchl1, the regulatory sequence comprises SEQ ID NO:3, i.e. nucleotides 36 to 133 of SEQ ID NO:5.

The two-dimensional structure of the regulatory sequence preferably further comprises a second internal loop domain (IL-2) comprising 6 to 12 nucleotides, preferably 7 to 11 nucleotides. The second internal loop domain (IL-2) is preferably asymmetrical and/or A/U rich.

The functional nucleic acid molecule of the present invention preferably comprises a regulatory sequence having a two-dimensional structure comprising a sequence with at least 50% identity with SEQ ID NO:4, preferably at least 75% identity with SEQ ID NO:4, more preferably at least 90% identity with SEQ ID NO:4.

In the exemplified inverted SINE B2 transposable element derived from AS Uchl1, the regulatory sequence comprises SEQ ID NO:4, i.e. nucleotides 22 to 150 of SEQ ID NO:5.

The two-dimensional structure of the regulatory sequence preferably further comprises a first internal loop domain (IL-1) comprising 6 to 12 nucleotides, preferably 7 to 11 nucleotides.

The functional nucleic acid molecule of the present invention preferably comprises a regulatory sequence having a two-dimensional structure comprising a sequence with at least 50% identity with SEQ ID NO:5, preferably at least 75% identity with SEQ ID NO:5, more preferably at least 90% identity with SEQ ID NO:5.

In the exemplified inverted SINE B2 transposable element derived from AS Uchl1, the regulatory sequence has SEQ ID NO:5.

Another functional nucleic acid molecule according to the present invention comprises a target binding sequence comprising a sequence reverse complementary to a target mRNA sequence for which protein translation is to be enhanced; and a regulatory sequence comprising a sequence having at least 50%, preferably at least 75%, even more preferably at least 90% identity with a sequence selected from the group consisting of SEQ ID NO:15, SEQ ID NO:16, SEQ ID NO:17, SEQ ID NO:18, SEQ ID NO:19, SEQ ID NO:20, SEQ ID NO:21, SEQ ID NO:15, SEQ ID NO:7, SEQ ID NO:22, and SEQ ID NO:23.

icSHAPE analysis shows that the number of paired nucleotides in the above disclosed stems and the number of nucleotides in the above disclosed loops can vary beyond the disclosed ranges.

Another functional nucleic acid molecule according to the present invention comprises a target binding sequence comprising a sequence reverse complementary to a target mRNA sequence for which protein translation is to be enhanced; and a regulatory sequence comprising a sequence having at least 50%, preferably at least 75%, even more preferably at least 90% identity with a sequence selected from the group consisting of SEQ ID NO:7, SEQ ID NO:21, SEQ ID NO:17, SEQ ID NO:22, SEQ ID NO:65, SEQ ID NO:66 and SEQ ID NO:67.

The regulatory sequence preferably comprises SEQ ID NO:7, SEQ ID NO:21, SEQ ID NO:17, SEQ ID NO:22, SEQ ID NO:65, SEQ ID NO:66 and SEQ ID NO:67.

In an alternative embodiment the functional nucleic acid comprises a regulatory sequence comprising a sequence having at least 50%, preferably at least 75%, even more preferably at least 90% identity with SEQ ID NO:12, even more preferably the sequence is SEQ ID NO:12.

Another functional nucleic acid molecule according to the present invention comprises a target binding sequence comprising a sequence reverse complementary to a target mRNA sequence for which protein translation is to be enhanced; and a regulatory sequence comprising one or more of the motifs formed by an RNA sequence having 50%, preferably 75%, even more preferably 90% identity with GCU (motif 1), AGGGC (motif 3), UGGAU (motif 4), UGGUGG (motif 6), or UGGA (motif 7) and by a hybridised reverse complementary RNA thereof, or the motif formed by an RNA sequence having 50%, preferably 75%, even more preferably 90% identity with AGGAGG (motif 2) and by a hybridised partially complementary reverse RNA thereof, or the motif formed by an RNA sequence having 50%, preferably 75%, even more preferably 90% identity with UGG (motif 5) and by a hybridised partially complementary reverse RNA thereof.

Even more preferably the motifs are respectively formed by GCU (motif 1), AGGGC (motif 3), UGGAU (motif 4), UGGUGG (motif 6), and UGGA (motif 7) and by a hybridised reverse complementary RNA thereof, AGGAGG (motif 2) and by a hybridised partially complementary reverse RNA thereof, and UGG (motif 5) and by a hybridised partially complementary reverse RNA thereof.

The regulatory sequence of the above-said functional nucleic acid molecule preferably comprises at least the motif formed by an RNA sequence having 90% identity with UGGUGG (motif 6) and by a hybridised reverse complementary RNA thereof. More preferably the motif is UGGUGG.

Preferred combinations of the above-said motifs are shown in FIGS. 24 to 39, 43 to 47 and 48B.

More specifically the above said functional nucleic acid molecule comprises as regulatory sequence a sequence having at least 50%, preferably 75%, even more preferably 90% identity with a sequence selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, and SEQ ID NO:77. Even more preferably, the sequence comprises SEQ ID NO:69, SEQ ID NO:70, SEQ ID NO:71, SEQ ID NO:72, SEQ ID NO:73, SEQ ID NO:74, SEQ ID NO:75, SEQ ID NO:76, and SEQ ID NO:77. Among these, the preferred sequence is SEQ ID NO:72, which represents an example of minimal functional sequence, which—despite the lack of several motifs of the full length SINEUP effector domain—maintains the ability of increasing translation of target RNA.

The functional nucleic acid molecule according to the present invention is preferably a circular molecule. This conformation leads to a much more stable molecule that is degraded with greater difficulty within the cell and therefore remains active for a longer time.

The present invention also relates to compositions comprising the above said functional nucleic acid molecules. Any compositions are included allowing to deliver the above said functional nucleic acid molecules by viral vectors (AAV, lentivirus and the like) and non-viral vectors (nanoparticles, lipid particles and the like).

EXAMPLES

Example 1

This example demonstrates the accessibility to chemical agents (DMS and CMCT) of each nucleotide in the inverted SINE B2 sequence from natural AS Uchl1. Accessibility to chemical agents is strictly dependent on the local structure of the molecule.

Figure 1:
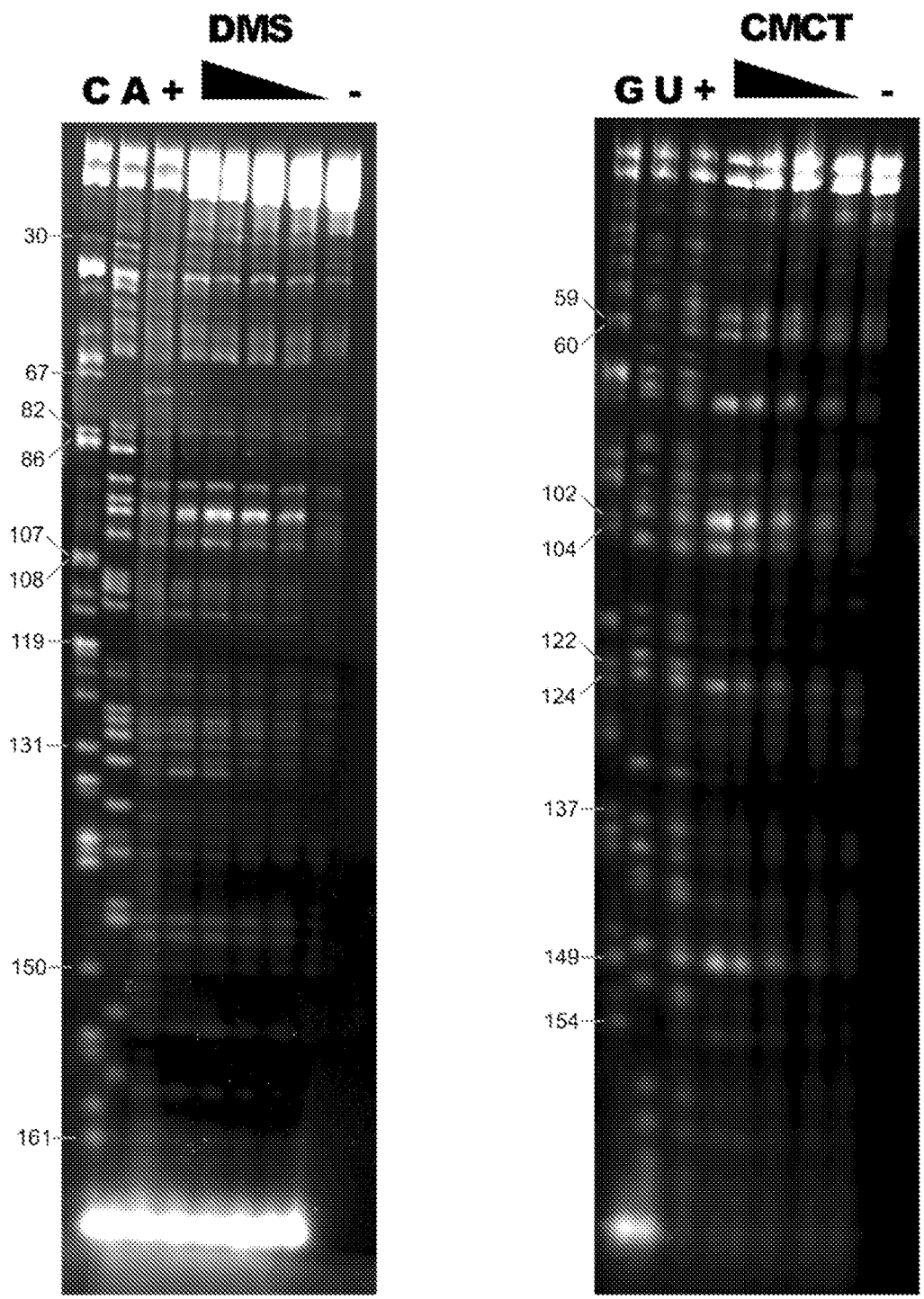
FIG. 1 related to Example 1 shows chemical footprinting of the inverted SINE B2 sequence from natural AS Uchl 1.

FIG. 1 shows chemical footprinting of the invSINEB2/183 RNA construct. The left panel shows a fluorescent gel with C and A sequencing lanes with nucleotide numbering. DMS lanes with invSINEB2/183 RNA treated with increasing DMS concentrations with positive (+) and negative (−) controls. The right panel shows a fluorescent gel with G and U sequencing lanes with nucleotide numbering. CMCT lanes with invSINEB2/183 RNA treated with increasing CMCT concentrations with positive (+) and negative (−) controls. Experiments were carried out as described in Tijerina P. et al., (2007), Nature Protocols 2:2608-2623.

Example 2

This example shows the two-dimensional structure of the inverted SINE B2 effector domain of functional AS Uchl1. The structure is organized in Stem-Loops (SL1, SL2 and SL3), Internal Loops (IL1, IL2, IL3 and IL4) and intervening stem structures. The structure is generated based on data from Example 1.

Figure 2:
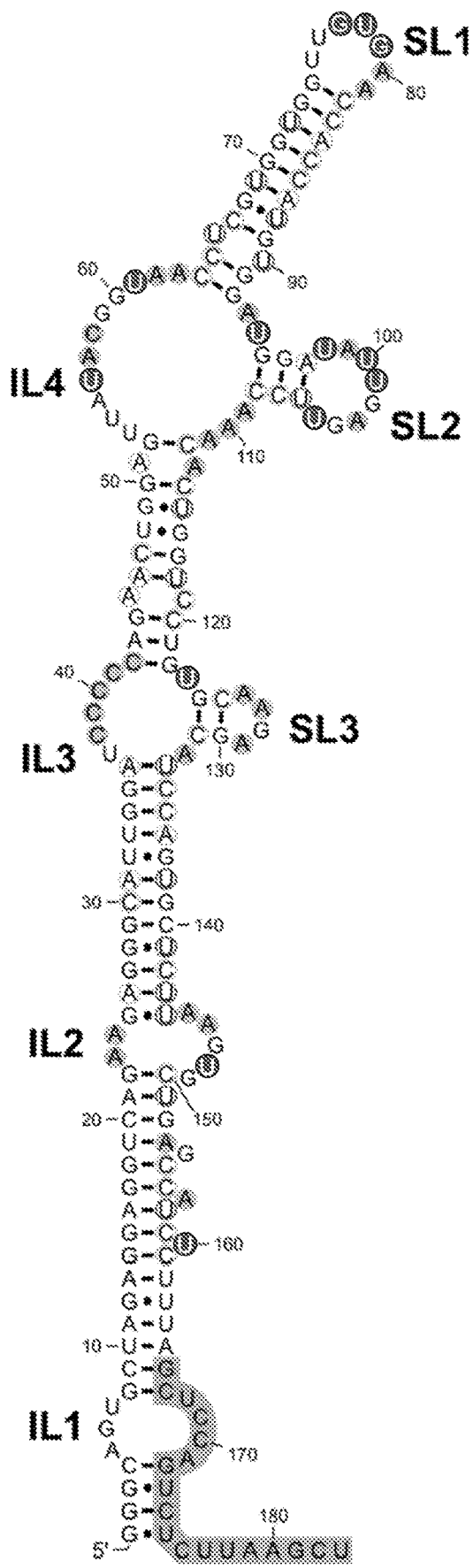
FIG. 2 related to Example 2 shows the secondary structure of the inverted SINEB2 sequence from natural AS Uchl 1 (SEQ ID NO:5).

FIG. 2 shows the secondary structure of the inverted SINE B2 effector domain of AS Uchl1. DMS reactive nucleotide are shown in black characters in circles with grey background and CMCT reactive nucleotides are shown in white characters in circles with black background, respectively. Internal loops and stem-loops are labeled as ILx and SLx, respectively. Non-reactive nucleotides are only circled. The segment shaded in gray corresponds to the DNA primer hybridization site.

Example 3

This example demonstrates that shorter fragments of the inverted SINE B2 sequence retain the terminal SL1 structure.

Figure 3:
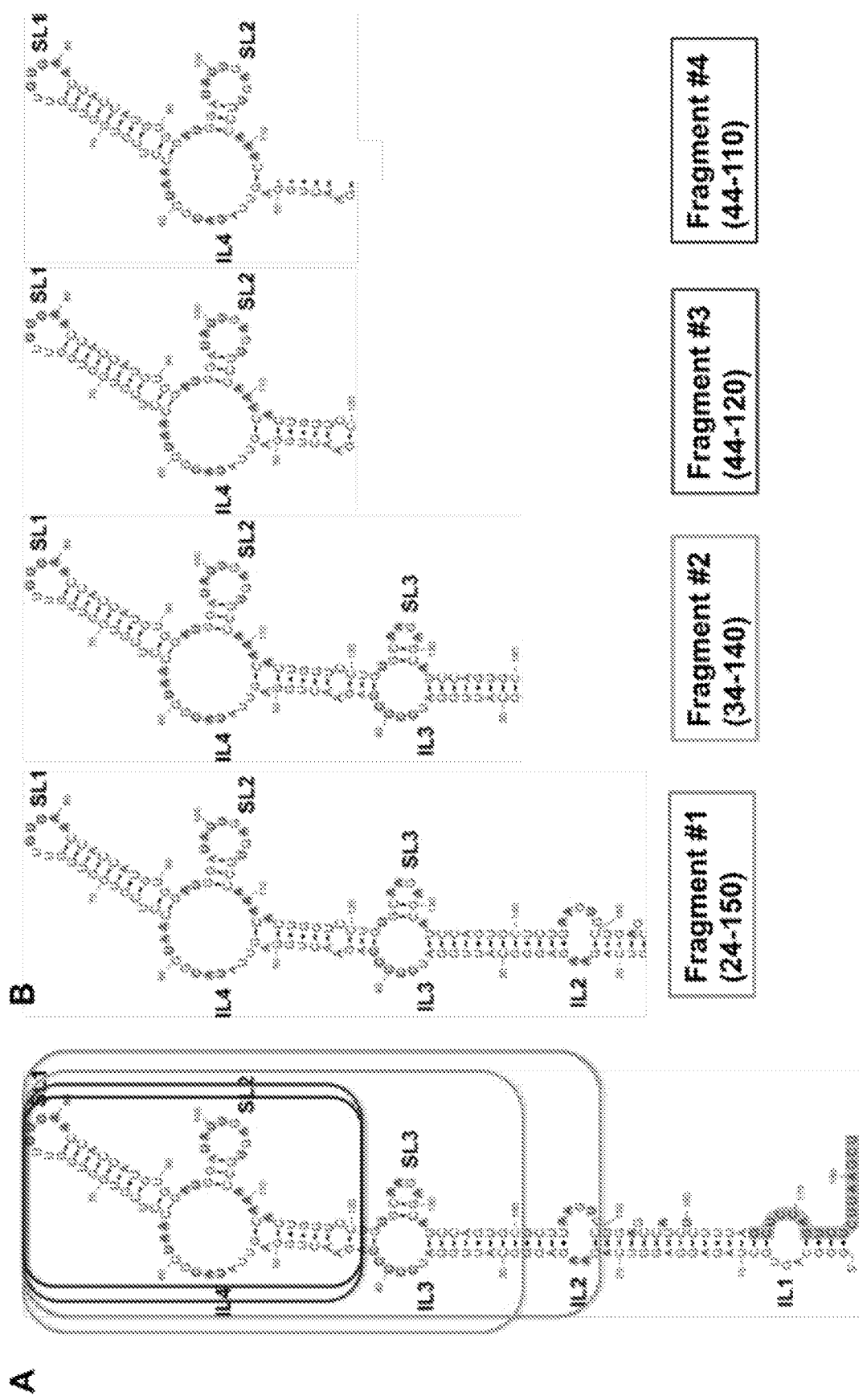
FIG. 3 related to Example 3 shows structures in solution of termini-deleted fragments of inverted SINE B2 RNA. The sequence in panel A is SEQ ID NO:5. The sequences in panel B are: fragment 1 is SEQ ID NO:78, fragment 2 is SEQ ID NO:79, fragment 3 is SEQ ID NO:7, and fragment 4 is SEQ ID NO:80.
Figure 3:
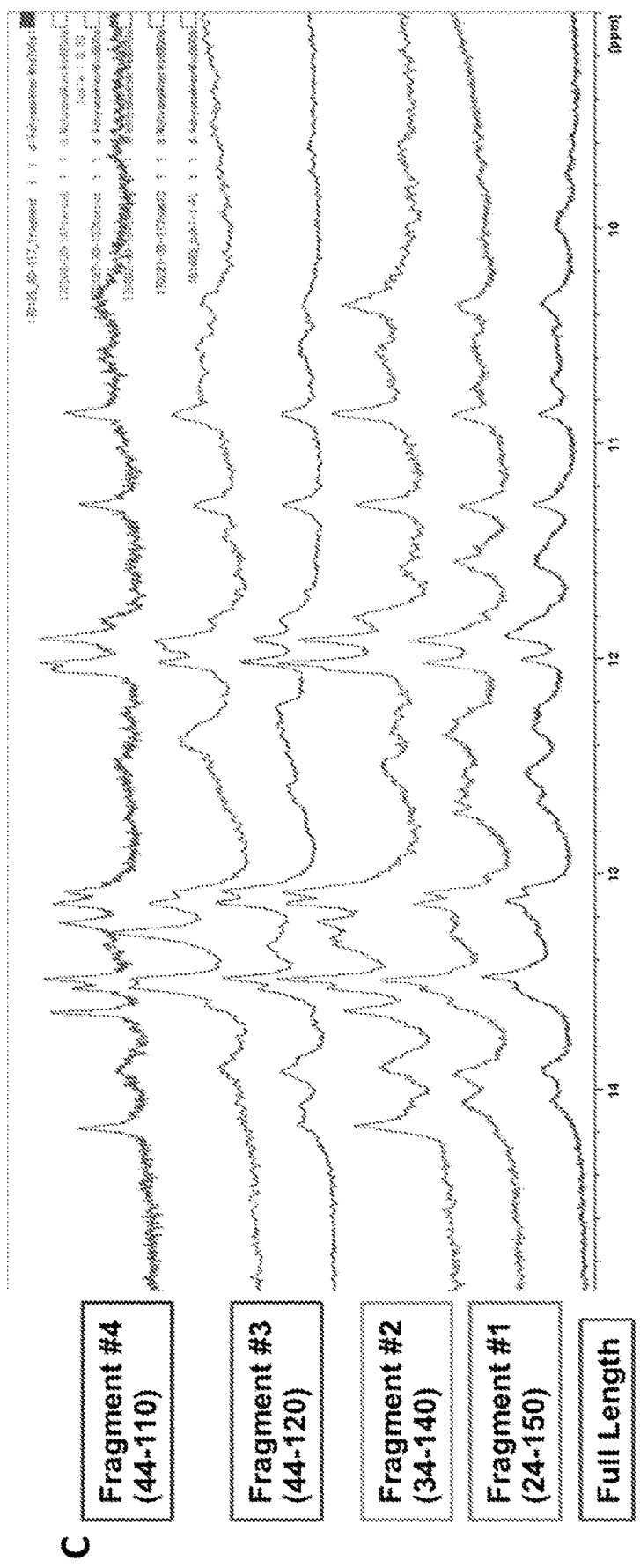

FIG. 3 shows the structures in solution of termini-deleted fragments of inverted SINE B2 RNA. FIG. 3A shows the 2D structure of the invSINEB2/183 effector domain of AS Uchl1. Regions with removed termini are indicated in squares. FIG. 3B shows the schematic structure of termini-deleted fragments. Nucleotide positions are indicated relative to the full-length sequence. FIG. 3C shows imino proton region of inverted SINE B2 from mouse AS Uchl1. Imino $^1$H signals are assigned for each termini-deleted fragment. Fragments #1 (SEQ ID NO:9), #2 (SEQ ID NO:8), #3 (SEQ ID NO:7) and #4 (SEQ ID NO:6) tracks are shown. The SL1 stem structure is observed in all fragments.

Example 4

This example demonstrates that SL1 is required for the activity of the inverted SINE B2 effector domain in functional nucleic acid molecule (AS Uchl1) for translation up-regulation.

Figure 4:
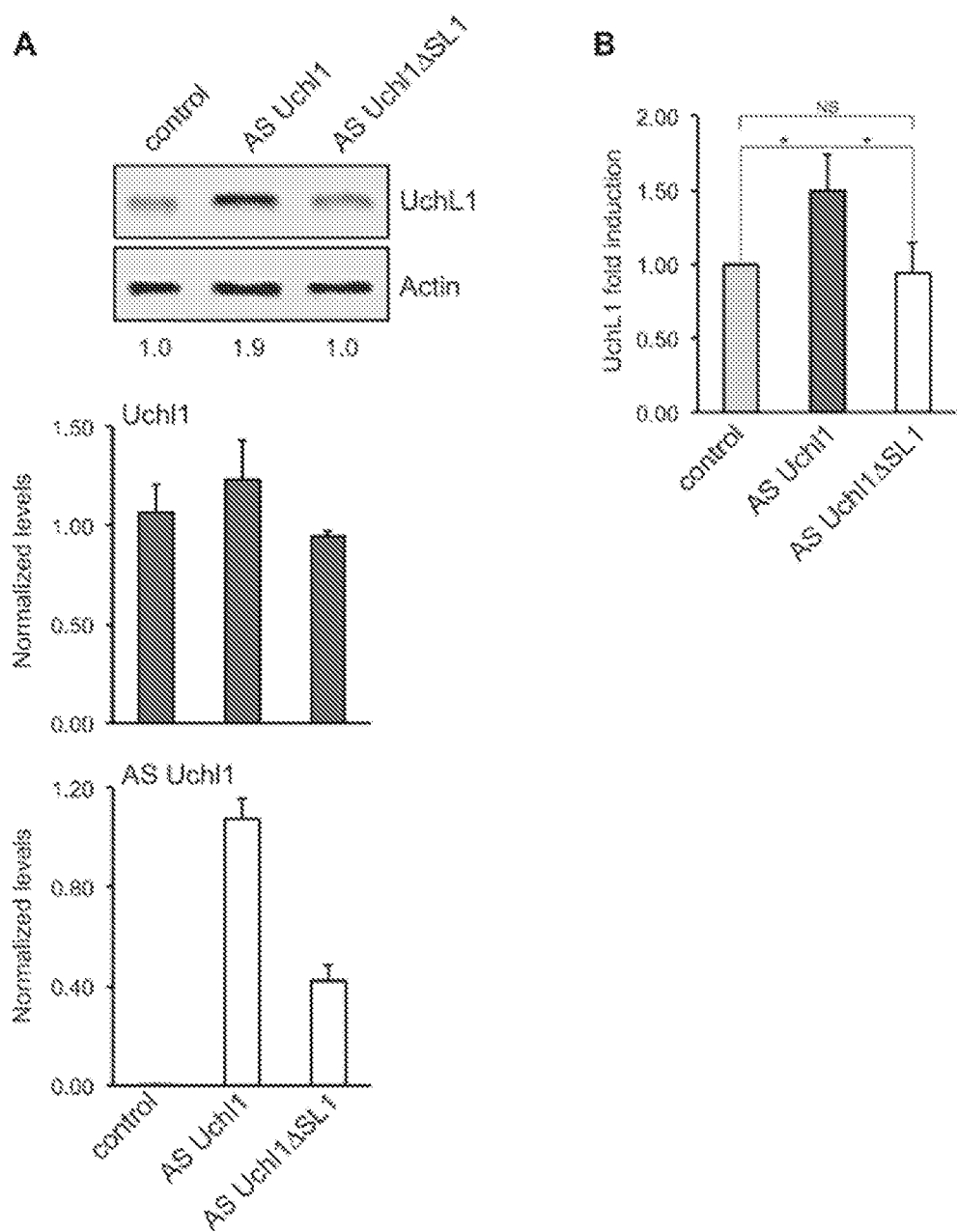
FIG. 4 related to Example 4 shows that the first stem-loop domain (SL-1) contributes to AS Uchl1 activity by Western blot and qRT-PCR.

Murine neuroblastoma N2a cells (ATCC Cat No. ATCC-CCL-131) were transfected with AS Uchl1 and ΔSL1 mutant constructs. In the ΔSL1 mutant construct, nucleotides 68-77 of embedded inverted SINE B2 are deleted (SEQ ID NO:10). In the ΔSL1 mutant the stem loop structure of SL-1 is destroyed, but the overall inverted SINE B2 assembly is retained. Control cells were transfected with an empty control plasmid. 48 hours after transfection, cells were lysed and processed for protein and RNA levels. Western blot was performed with anti-UCHL1 antibody (FIG. 4A). β-actin was used as loading control. Fold-induction was calculated on Western blot images normalized to β-actin and relative to empty control samples. Expressions of Uchl1 mRNA (gray bars) and AS Uchl1 (white bars) were monitored by qRT-PCR using specific primers. Data indicate mean±st. dev. Data are representative of N=5 independent replicas. FIG. 4B shows a graphical representation of AS Uchl1 and ΔSL1 translation enhancement activity on endogenous Uchl1 mRNA in N2a cells (N=5). *, p=0.01; NS, not significant (p>0.5).

Experiments were carried out as described in Zucchelli S. et al., (2015), Front Cell Neurosci. 9:174.

Example 5

This example demonstrates that SL-1 is required for translation up-regulation function of AS Uchl1 nucleic acid molecule in human hepatocellular cell line and with over-expressed mRNA. Indeed, the deletion of SL-1 abolishes AS Uchl1 activity when tested with overexpressed Uchl1-FLAG in human HepG2 cells (ATCC Cat No. ATCC-HB-8065).

Figure 5:
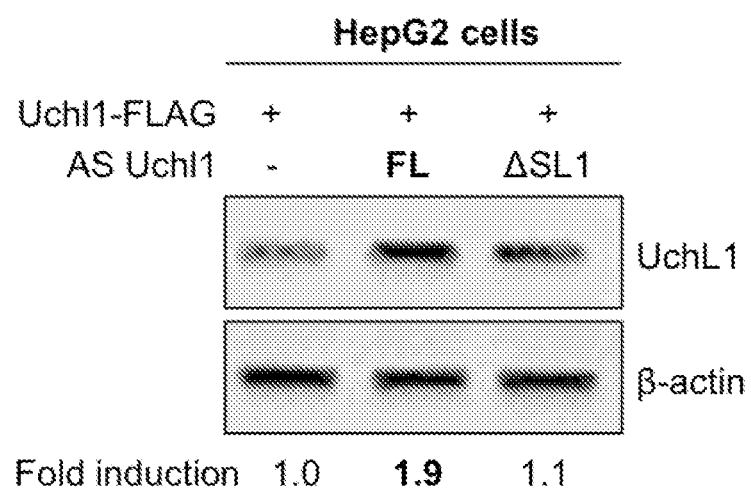
FIG. 5 related to Example 5 shows that the first stem-loop domain (SL-1) is required for translation up-regulation of AS Uchl1 nucleic acid molecule in human hepatocellular cell line and with overexpressed Uchl1-FLAG by Western blot and qRT-PCR.
Figure 5:
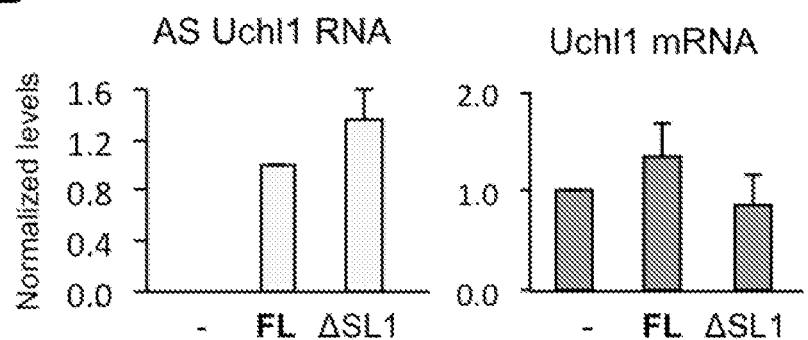

Human hepatocyte HepG2 cell line were transfected with Uchl1-FLAG construct in combination with AS Uchl1 and ΔSL1 mutant constructs. Control cells were transfected with an empty control plasmid. 48 hours after transfection, cells were lysed and processed for protein quantities by Western blot. Western blot was performed with anti-FLAG antibody to monitor overexpressed protein (FIG. 5A). β-actin was used as loading control. Fold-induction was calculated on Western blot images normalized to β-actin and relative to empty control samples. AS Uchl1 translation enhancer activity is highlighted in bold. Cells treated as disclosed above were processed for RNA quantification (FIG. 5B). Expressions of Uchl1 mRNA (right) and AS Uchl1 (left) were monitored by qRT-PCR using specific primers. Data indicate mean±st. dev.

Example 6

This example demonstrates that SL-1 is required for translation up-regulation function of synthetic functional nucleic acid molecule targeting overexpressed mRNA (SINEUP-GFP). Additional structural elements are preferably also required since StemDM mutant (which destabilize the stem) has diminished, but not abolished effector domain activity.

Figure 6:
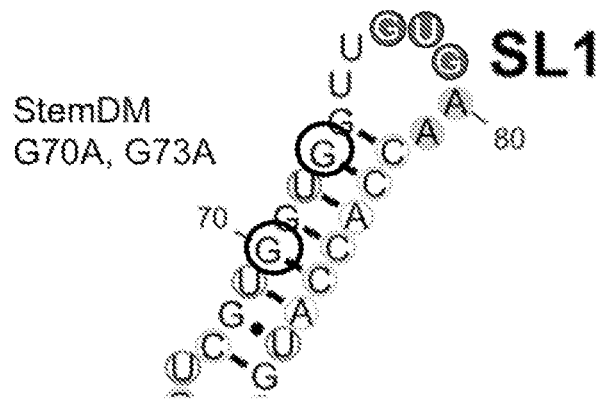
FIG. 6 related to Example 6 shows that the first stem-loop domain (SL-1) contributes to the translation up-regulation activity of antisense lncRNA overlapping with GFP mRNA (SINEUP-GFP) in HEK 293T/17 cells by Western blot and qRT-PCR. The sequence in panel A is SEQ ID NO:81.
Figure 6:
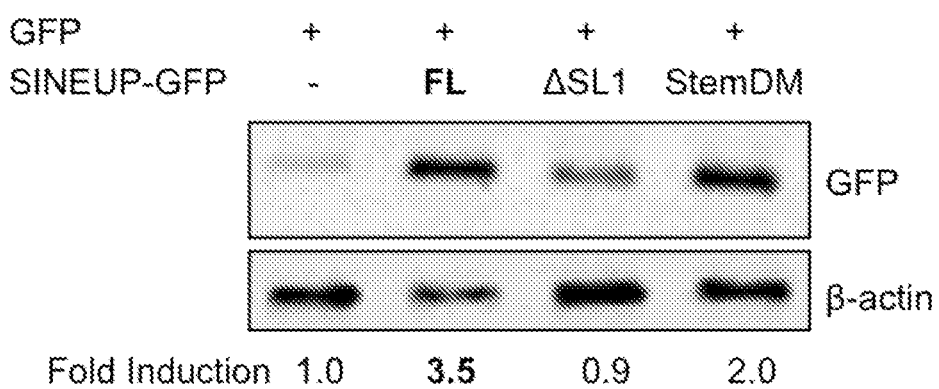
Figure 6:
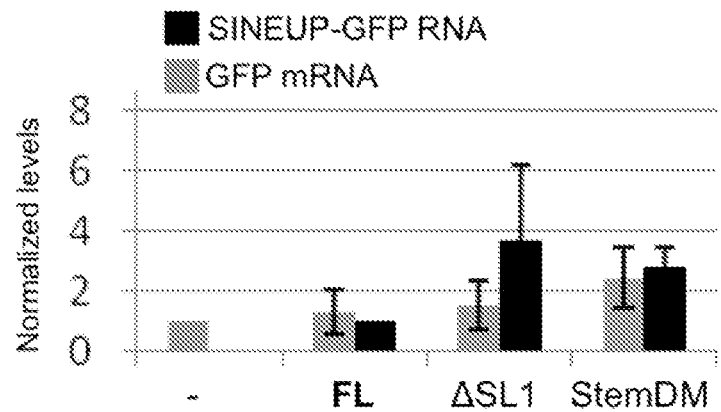

FIG. 6 shows that the SL-1 structural element contributes to SINEUP-GFP activity in HEK 293T/17 cells (ATCC Cat No. ATCC-CRL-11268). FIG. 6A is a zoomed-in image of the terminal hairpin structure (SL-1) from the inverted SINE B2 effector domain. A ΔSL1 mutant was generated by deletion in the SINE B2 effector domain of SINEUP-GFP. Similarly, site-directed mutations (G70A and G73A, circled) were introduced in SINEUP-GFP to generate the StemDM mutant (SEQ ID NO:11). In FIG. 6B HEK 293T/17 cells were transfected with eGFP expressing plasmid in combination with an empty vector (−), or SINEUP-GFP full-length (FL), ΔSL1 or StemDM mutants, as indicated. Western blot was performed with anti-GFP antibody to monitor overexpressed protein. β-actin was used as loading control. Fold-induction was calculated on Western blot images normalized to β-actin and relative to empty control samples. SINEUP-GFP translation enhancer activity is highlighted in red. In FIG. 6C, cells treated as in FIG. 6B were used to prepare RNA. Expressions of GFP mRNA (grey) and SINEUP-GFP (black) were monitored by qRT-PCR using specific primers. Data indicate mean±st. dev.

Example 7

This example demonstrates that the inverted SINE B2 fragment (38 nucleotide) covering the SL1 structural region (SEQ ID NO:12) adopts a single structure in solution as determined by NMR. In this experiment, NMR data validate the structure of SL-1 in shorter fragment (as observed by other techniques in Examples 1, 2 and 3).

Figure 7:
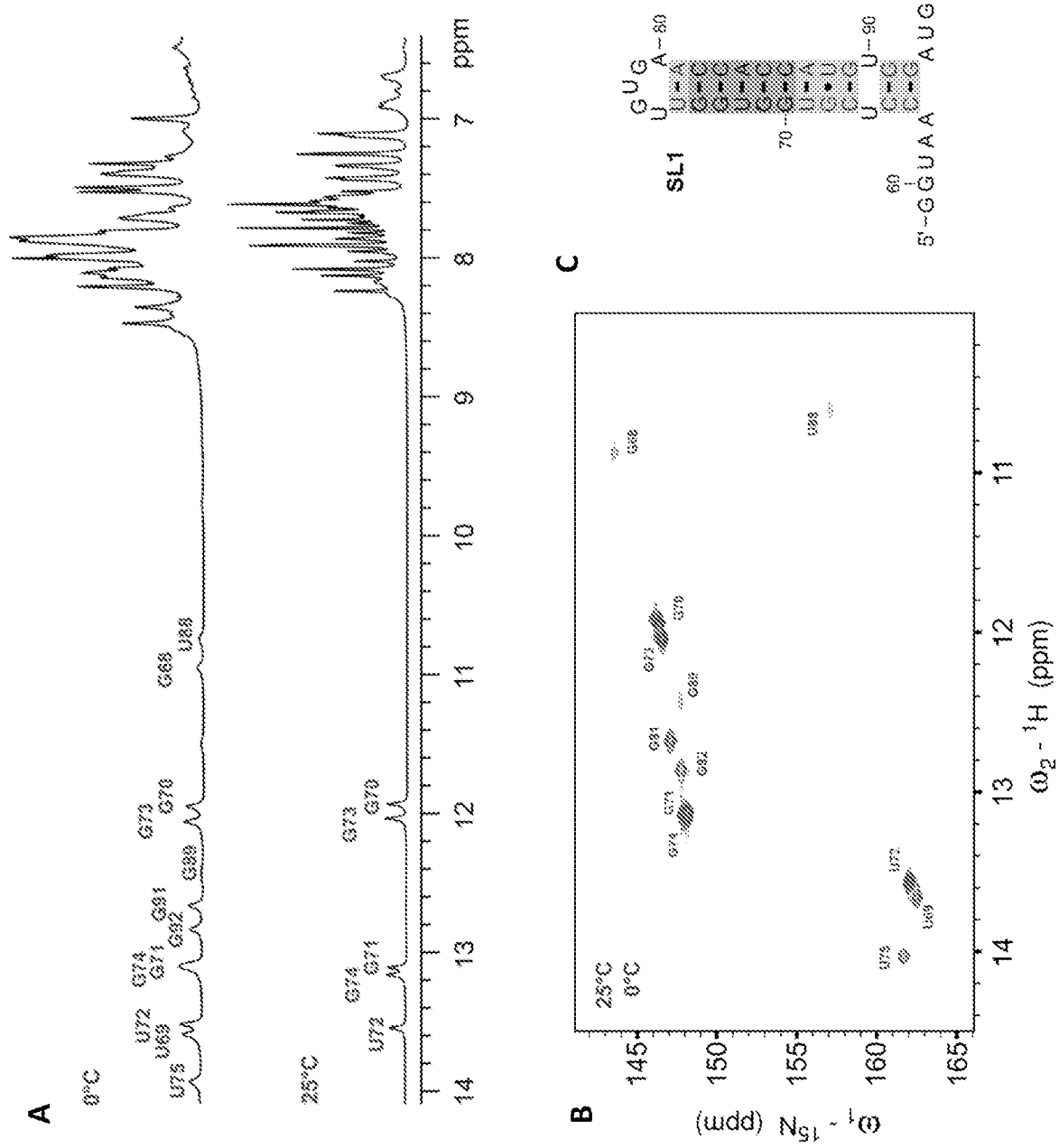
FIG. 7 related to Example 7 shows determination of structure in solution of the inverted SINE B2 fragment (38 nt) by NMR. The sequence in panel C is SEQ ID NO:12.

FIG. 7A shows imino and aromatic regions of $^1$H NMR spectra of 38 nt RNA in 5% $^2$H$_2$O/95% H$_2$O acquired at 0 and 25° C. Imino $^1$H signals are assigned. FIG. 7B shows imino region of the $^{15}$N HSQC NMR spectra. Signals observed at 25 and 0° C. are in dark grey and light grey, respectively. FIG. 7C shows the secondary structure of the SINEB2/38 construct. Base pairs with imino signals observable at 25 and 0° C. are shaded in dark grey and light grey, respectively. Experiments were carried out as described in Sybren S. et al., (1998), Prog. Nucl. Magn. Reson. Spectrosc. 32:287-387.

Example 8

This example demonstrates that NMR signals can be assigned in 2D NOESY NMR spectrum to properly reconstruct the 3D structure of inverted SINE B2 38 nt fragment.

Figure 8:
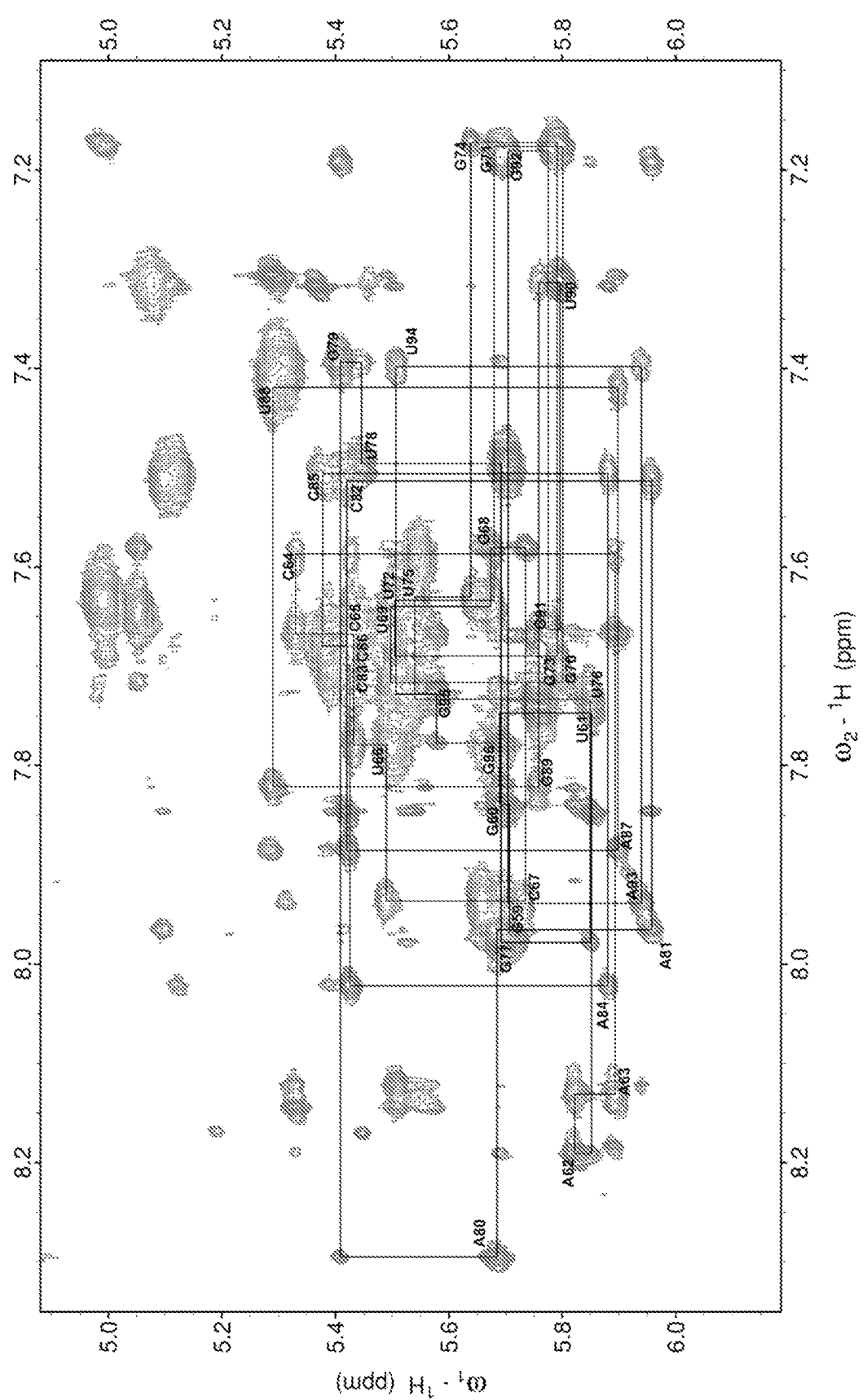
FIG. 8 related to Example 8 shows aromatic-anomeric region of a 2D NOESY NMR spectrum (τm=250 ms) of invSINEB2/38.

FIG. 8 shows the assignment of relevant resonances. Aromatic-anomeric region of a 2D NOESY NMR spectrum (τm=250 ms) of invSINEB2/38. The sequential walk is depicted as a black line.

Example 9

This example demonstrates the connectivity map of NMR signals that is used to properly reconstruct the 3D structure of inverted SINE B2 38 nt fragment.

Figure 9:
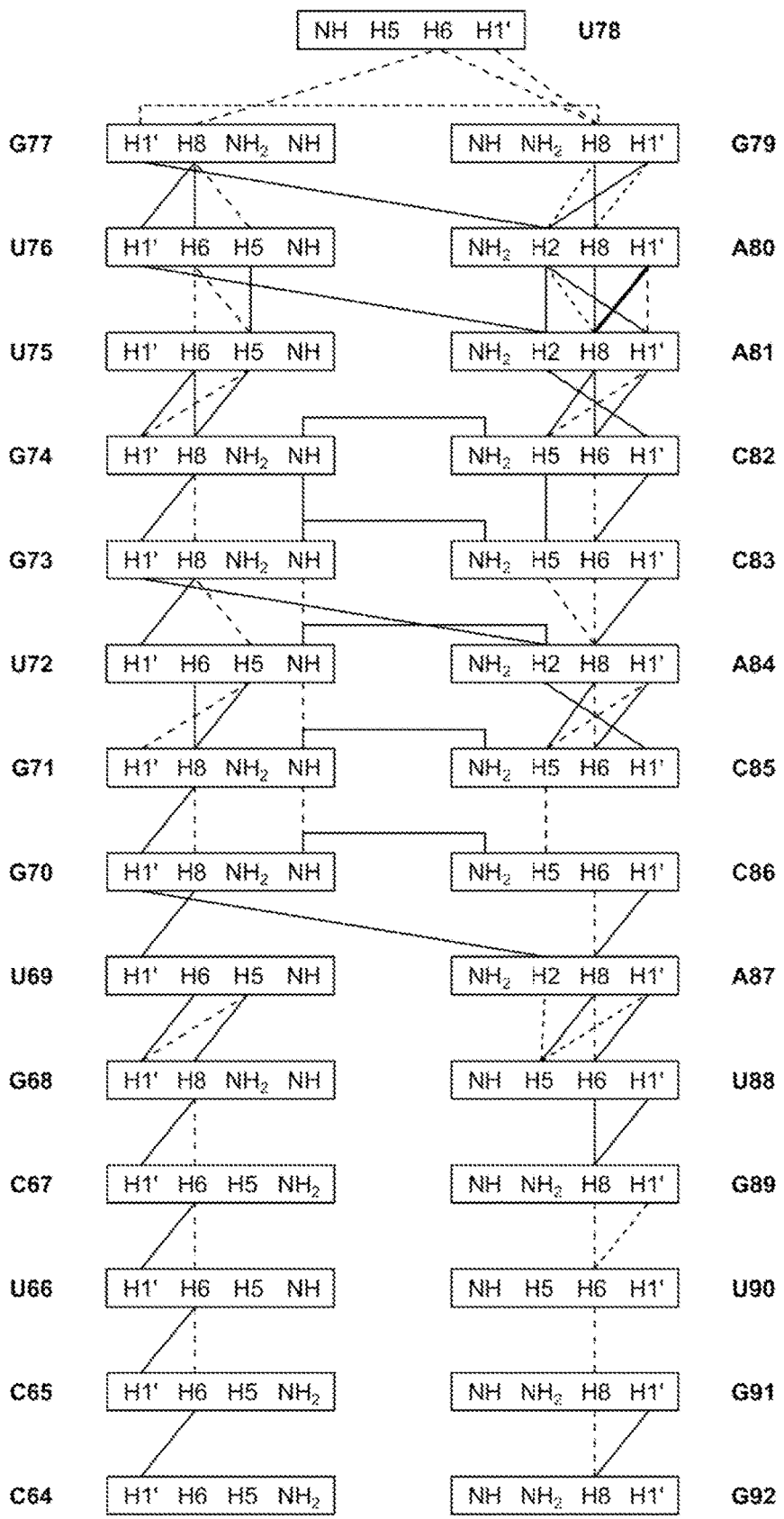
FIG. 9 related to Example 9 shows the connectivity map of NMR signals used to properly reconstruct the 3D structure of inverted SINE B2 38 nt fragment.

FIG. 9 shows a diagram of NOE connectivies. A diagram of strong (bold line) medium (solid line) and weak (dashed line) NOE connectivities for the invSINEB2/38 molecule.

Example 10

This example demonstrates the high-resolution 3D structure of the SL-1 region of the inverted SINE B2 effector domain. The hairpin adopts an A-type helical stem. The loop exhibits dynamic properties in solution.

Figure 10:
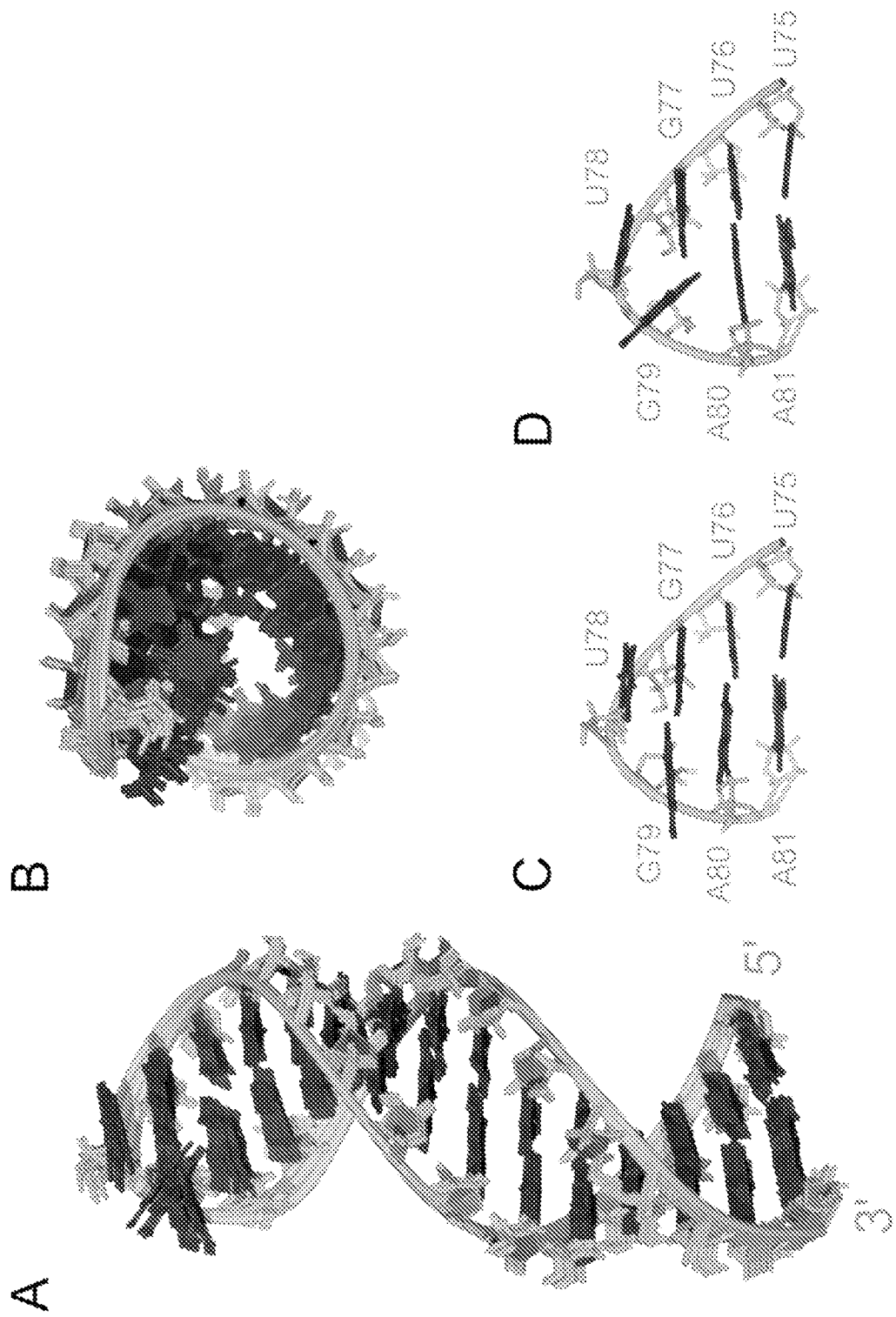
FIG. 10 related to Example 10 shows high-resolution 3D structure of the SL-1 region of the inverted SINE B2 effector domain.

FIG. 10 shows the high-resolution structure of SL1. FIG. 10A shows a side view and FIG. 10B shows top views of the 10 lowest energy structures of the 29 nt hairpin (SEQ ID NO:1). FIGS. 10C and 10D are representative structures of loops with orientations of G77, U78 and G79 bases.

Example 11

This example demonstrates that additional structural elements (IL3-SL3 region, IL4 and basal stem structure) contribute to inverted SINE B2 effector domain activity in functional nucleic acid molecule (in particular, SINEUP-GFP).

Figure 11:
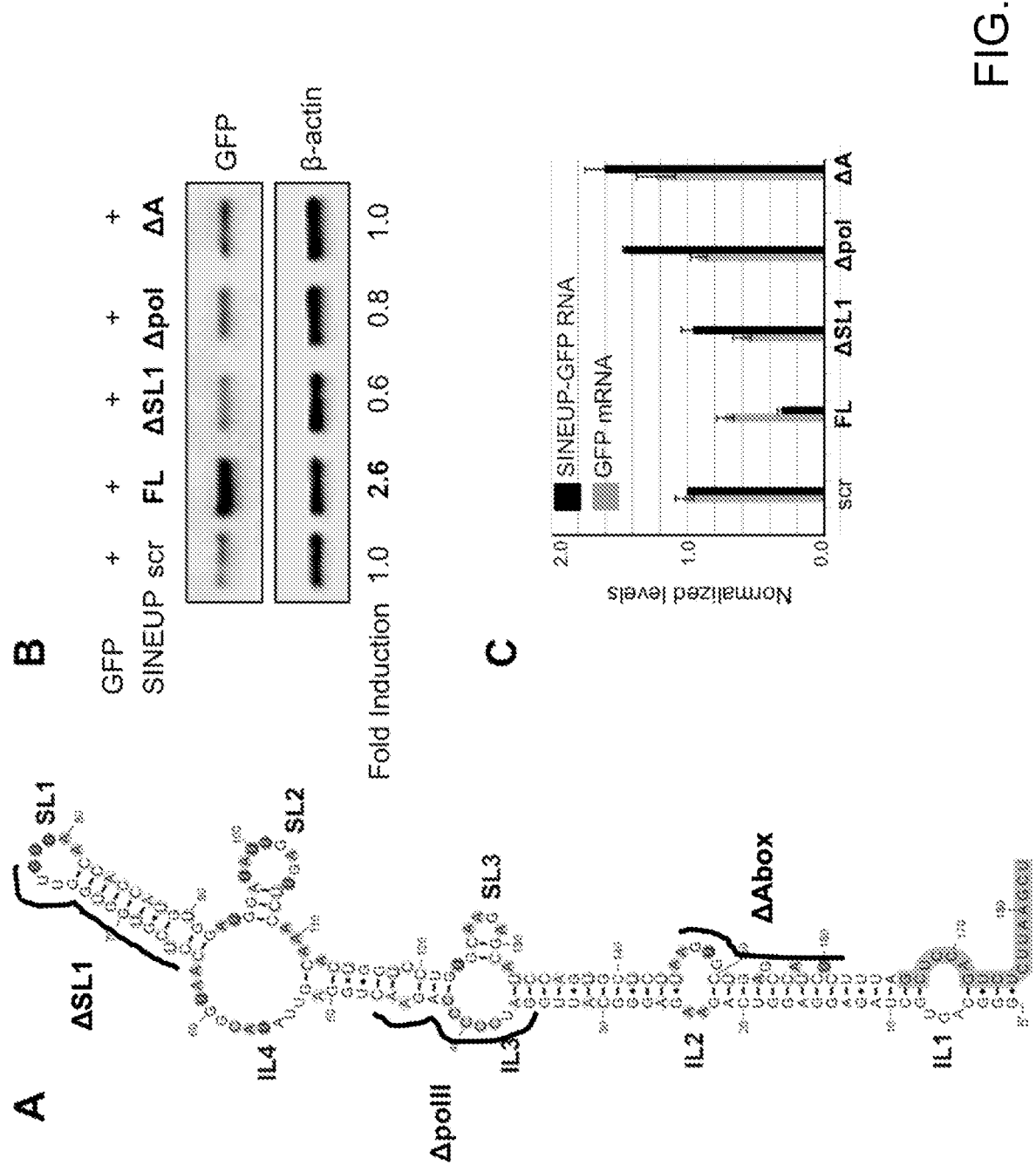
FIG. 11 related to Example 11 shows deleted sequences on the inverted SINE B2 and the effect of these deletions on inverted SINE B2 activity (Western blot and qRT-PCR). The sequence in panel A is SEQ ID NO:5.

FIG. 11A is a schematic representation of ΔSL1 (SEQ ID NO:10), ΔpolII (SEQ ID NO:13) and ΔBox (SEQ ID NO:14) deleted sequences annotated on inverted SINE B2 secondary structure. In FIG. 11B, HEK 293T/17 cells were transfected with eGFP expressing plasmid in combination with an empty vector (−), or SINEUP-GFP full-length (FL), ΔSL1, ΔpolII or ΔBox mutants, as indicated. Western blot was performed with anti-GFP antibody to monitor overexpressed protein. β-actin was used as loading control. Fold-induction was calculated on Western blot images normalized to β-actin and relative to empty control samples. SINEUP-GFP translation enhancer activity is highlighted in bold. The contribution of structural mutants is shown in red. In FIG. 11C, cells treated as in FIG. 11B were used to prepare RNA. Expressions of GFP mRNA (grey) and SINEUP-GFP (black) were monitored by qRT-PCR using specific primers. Data indicate mean±st. dev.

Example 12

This example demonstrates that new synthetic effector domain sequences can be designed based on structural features (intervening stem structure at the base of IL-4, SL-2, SL-1). These sequences can enhance translation up-regulation activity in functional nucleic acid molecule with overexpressed mRNA. Enhanced activity is obtained with different primary nucleotide sequence, but same structure.

In particular, structure-based variants of the inverted SINE B2 display increased translation up-regulation activity as effector domain in SINEUP-GFP. FIG. 12A shows a schematic representation of structure-based mutations annotated on inverted SINE B2 secondary structure. In circles: single point mutations; in squares: sequence swapping of structural elements (stem and loop-base). In FIG. 12B, HEK 293T/17 cells were transfected with eGFP expressing plasmid in combination with an empty vector (−), or SINEUP-GFP full-length (FL) as positive control. SINEUP-GFP constructs with structure-based mutations were transfected as indicated. Western blot was performed with anti-GFP antibody to monitor overexpressed protein. β-actin was used as loading control. FIG. 12C shows the relative increase in GFP protein levels (left panel) and unchanged GFP mRNA levels (right panel) in N=9 experiments, that have been performed as in B. The expression of each SINEUP-GFP structural mutant (AS GFP) is monitored by qRT-PCR and included in the right panel. All mutants are expressed at the same level.

Example 13

This example demonstrates that new synthetic effector domain sequences can be designed based on structural features (intervening stem structure at the base of IL-4, SL-2, SL-1) and obtain enhanced translation up-regulation activity in functional nucleic acid molecule with overexpressed mRNA. Enhanced activity is obtained with different primary nucleotide sequence, but same structure.

In particular, a shorter and structure-based variant of the inverted SINE B2 display increased translation up-regulation activity as effector domain functional nucleic acid molecule targeting endogenous mRNA.

Figure 13:
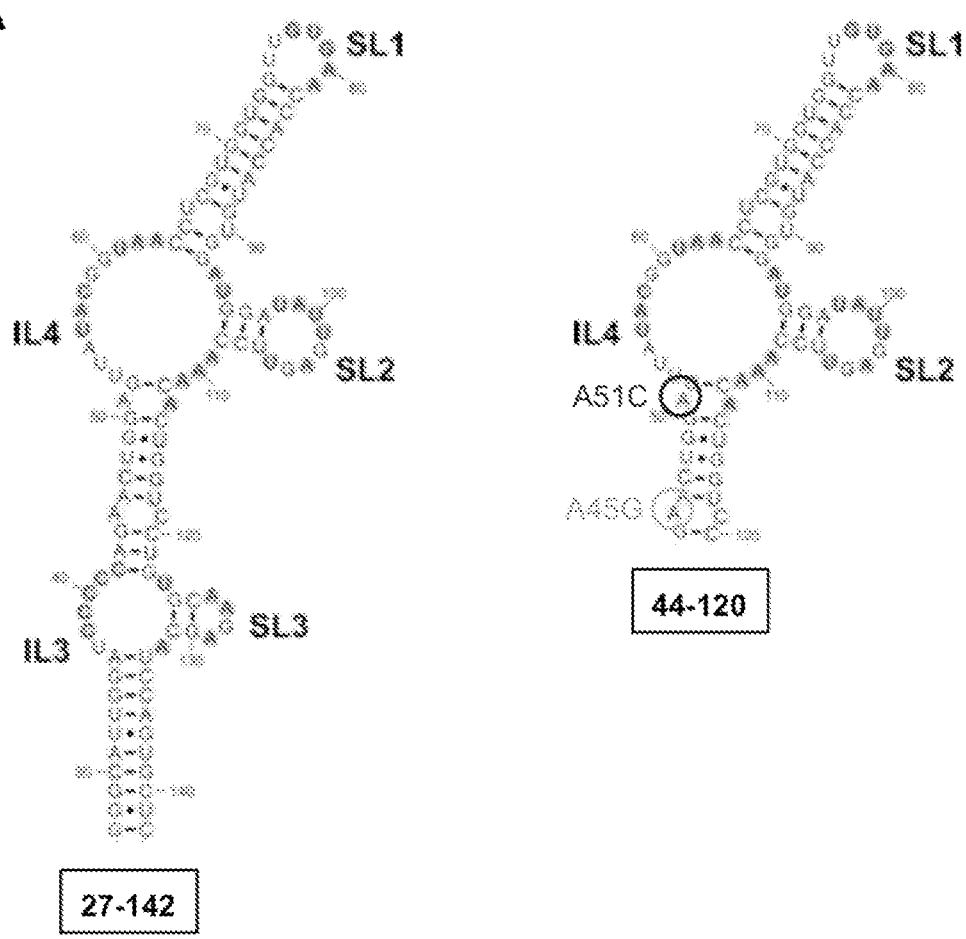
FIG. 13 related to Example 13 shows mutated sequences on a shorter version of the inverted SINE B2 and the effect of these mutations on inverted SINE B2 activity. The sequence of 27-142 is SEQ ID NO:21. The sequence of 44-120 is SEQ ID NO:7.
Figure 13:
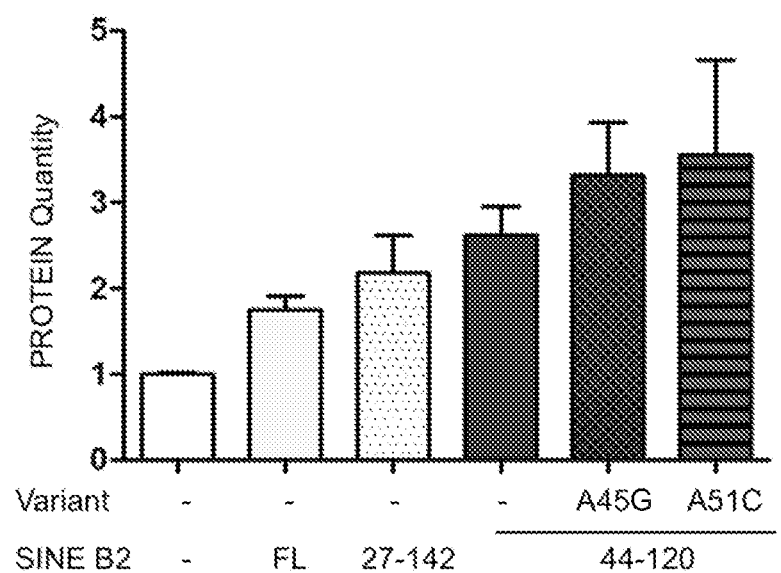

FIG. 13A is a schematic representation of structure-based mutations annotated on inverted SINE B2 secondary structure (27-142 corresponds to SEQ ID NO:21, 44-120 corresponds to SEQ ID NO:7, 44-120 with A45G corresponds to SEQ ID NO:22 and 44-120 A51C corresponds to SEQ ID NO:23). Single point mutations are indicated. FIG. 13B shows translation up-regulation activity of functional nucleic acid molecules targeting endogenously expressed mRNA in which the effector domain is a synthetic sequence with improved structural features. Depending on the conditions, alternative folding occurs and may become stronger such as SEQ ID NO:7.

Example 14

This example demonstrates that SINE sequences from natural antisense long non-coding RNAs are effector domains in functional nucleic acid molecules for translation up-regulation of partially overlapping mRNA.

In particular, SINEB2 elements from different mouse AS lncRNAs can act as Effector Domain in miniSINEUPs and up-regulate GFP protein expression in HEK293T (Riken Brc Cat. No. RCB2202).

Figure 14:
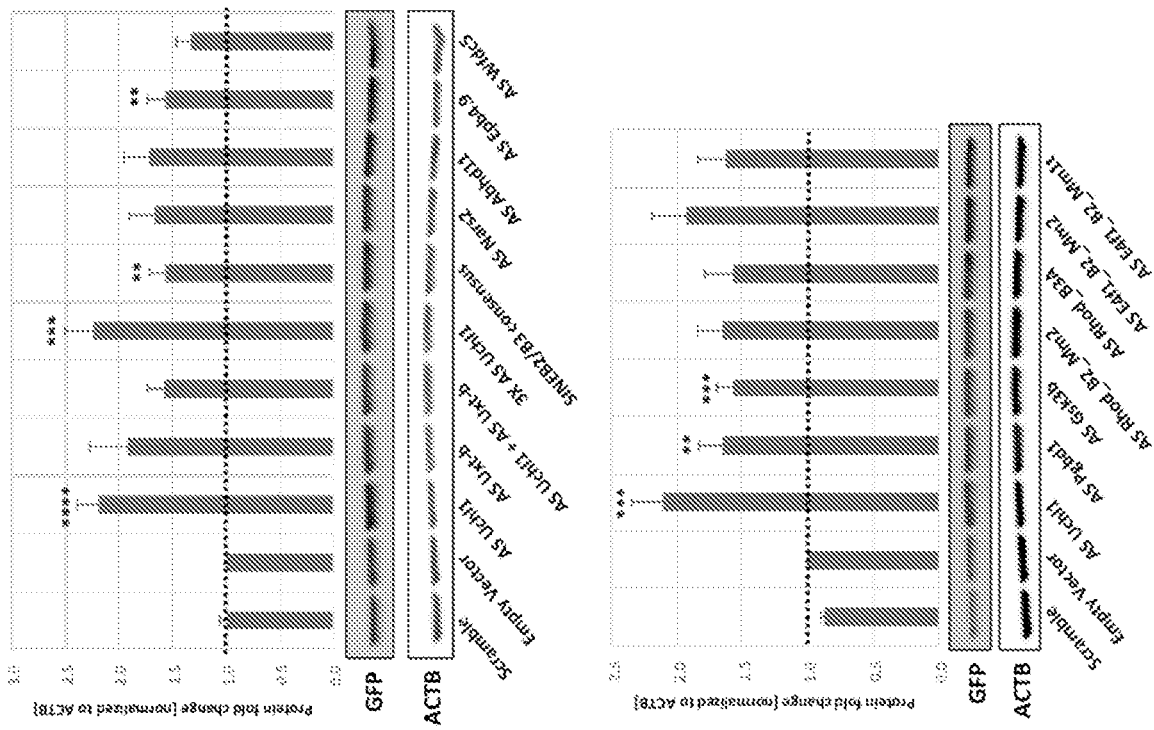
FIG. 14 related to Example 14 shows that SINEB2 elements from different mouse AS lncRNAs can act as Effector Domain in miniSINEUPs and up-regulate GFP protein expression in HEK293T (Western blot).
Figure 14:
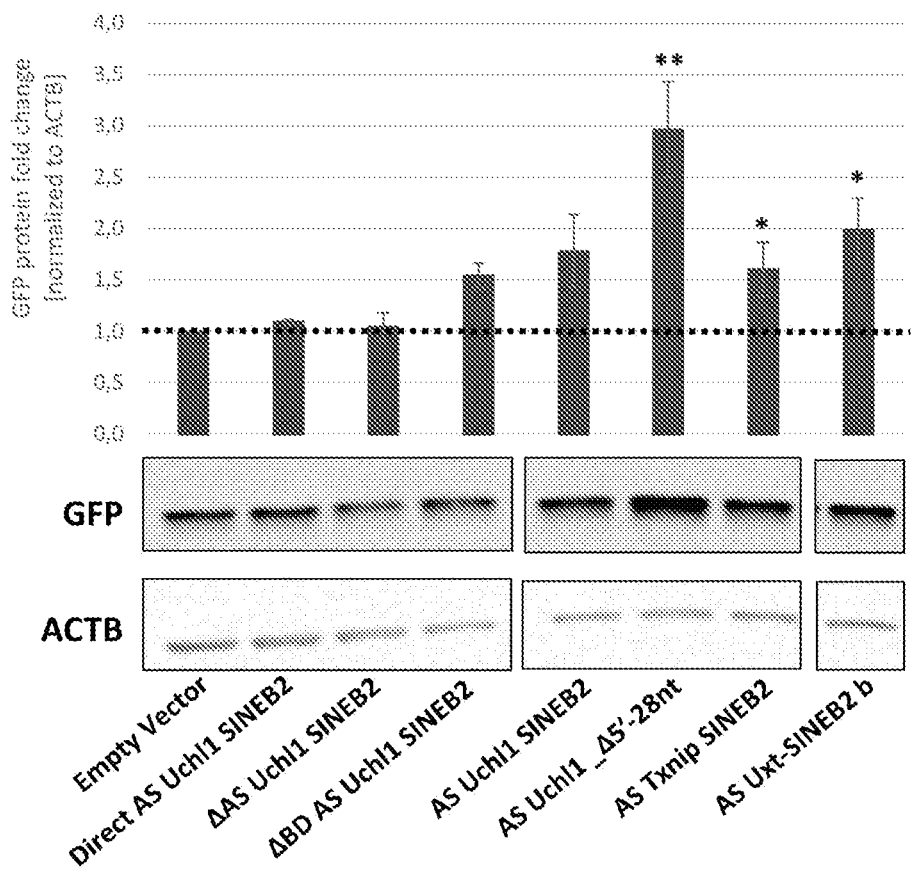

FIG. 14A shows SINE B2 sequences derived from natural functional antisense lncRNAs, which were cloned into miniSINEUP-GFP to replace the original inverted SINE B2 sequence from AS Uchl1 as Effector Domain. GFP targeting sequence was −40/+4 nucleotides, relative to initiating AUG codon. Sequences are in the order: SEQ ID NO:44, SEQ ID NO:47, SEQ ID NO:50 to SEQ ID NO:62. FIG. 14B shows GFP protein fold induction in HEK293T cells after co-transfection with sense EGFP and miniSINEUP-GFP (24 h post-transfection). Western blot images and corresponding GFP band intensities (normalized to ACTB expression level) are calculated using ImageJ software. Empty vector is used as negative control while AS Uchl1 (AS Uchl1 SINEB2 containing miniSINEUP) as positive control. Sample labels indicate names of AS lncRNAs from which SINEB2 sequences were isolated. SINEB2 sequences representing four sub-families (based on RepeatMasker annotation) namely B3, B3A, Mm2, and Mm1t were tested. SINEB2 elements are from B3 sub-family unless specifically stated. AS Uchl1+AS Uxt-b means AS Uchl1 SINEB2 and second SINEB2 of AS Uxt combined in ED. 3X indicates three repeats of SINEB2 and SINEB2/B3 consensus is the B3 sub-family consensus sequence taken from RepBase database. n=5; error bars±SEM; ** P<0.00005; * P<0.0005; ** P<0.005; * P<0.05; two-tailed Student's t-test FIG. 14C shows SINEB2 sequences tested as ED in SINEUP-GFP.

FIG. 14D shows Western blot images with anti-GFP and anti-ACTB antibodies and corresponding GFP band intensities (normalized to ACTB expression level) calculated using ImageJ software. ACTB is used as loading control. Here, AS Uchl1 SINEB2 represents SINEUP-GFP with −40/+32 BD design with respect to the EGFP start codon (+21 nt spacer sequence), and AS Uchl1 SINEB2 as ED in addition to the Alu and 3' tail from AS Uchl1. AS Txnip SINEB2 and AS Uxt-SINEB2 b follow the same design except that the AS Uchl1 SINEB2 is replaced by the SINEB2 elements from AS Txnip and AS Uxt (SINEB2-b) respectively. AS Uchl1_Δ5'-28 nt is same as AS Uchl1 SINEB2 but with shorter BD (−40/+4 with respect to EGFP start codon). Direct=direct orientation of SINEB2; Δ=deletion. n=3; error bars±SEM; ** P<0.005; * P<0.05; two-tailed Student's t-test Example 15

This example demonstrates that active SINE sequences in functional nucleic acid molecules for translation up-regulation function have poor sequence identity. This example suggests structure-dependence of effector domain functionality.

Figure 15:
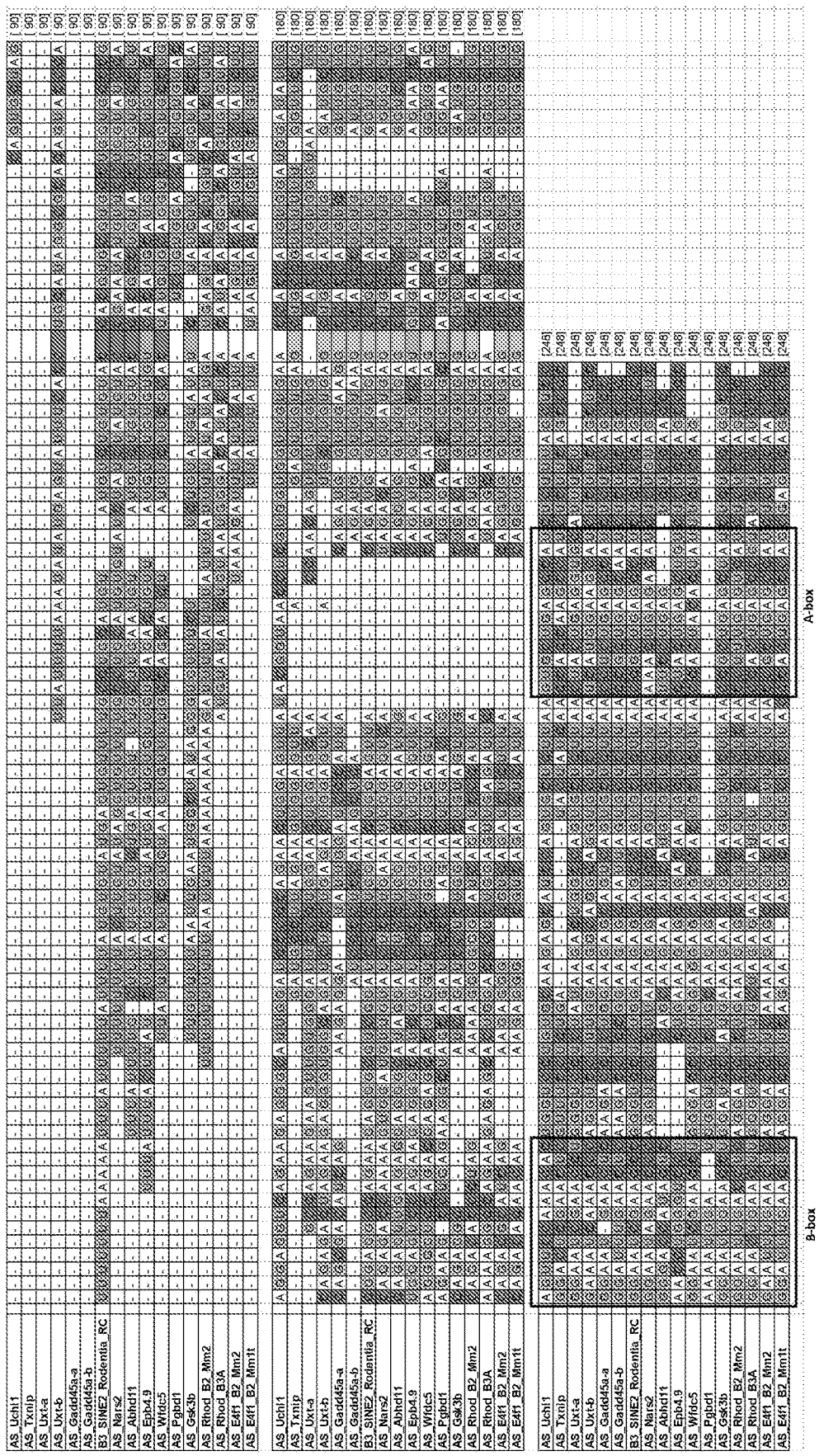
FIG. 15 related to Example 15 shows ClustalW sequence alignment of SINEB2 elements from different mouse AS lncRNAs. The sequence of AS_Uchl1 is SEQ ID NO:44. The sequence of AS_Txnip is SEQ ID NO:45. The sequence of AS_Uxt-a is SEQ ID NO:46. The sequence of AS_Uxt-b is SEQ ID NO:47. The sequence of AS_Gadd45a-a is SEQ ID NO: 48. The sequence of AS_Gadd45a-B is SEQ ID NO:49. The sequence of B3_SINE2 Rodentia RC is SEQ ID NO:52. The sequence of AS_Nars2 is SEQ ID NO:53. The sequence of AS_Abhd11 is SEQ ID NO:54. The sequence of AS_Epb4.9 is SEQ ID NO:55. The sequence of AS_Wfdc5 is SEQ ID NO:56. The sequence of AS_Pgbd1 is SEQ ID NO:57. The sequence of AS_Gsk3b is SEQ ID NO:58. The sequence of AS_Rhod_B2_Mm2 is SEQ ID NO:59. The sequence of AS Rhod_B3A is SEQ ID NO:60. The sequence of AS_E4f1 B2_Mm2 is SEQ ID NO: 61. The sequence of AS_E4f1_B2_Mmlt is SEQ ID NO:62.

FIG. 15 shows ClustalW sequence alignment of SINEB2 elements from different mouse AS lncRNAs. Mouse SINEB2 sequences that were selected for translation up-regulation function in SINEUP-GFP and miniSINEUP-GFP (example 14) are aligned by ClustalW in MEGAS software. Sequences are in the order: SEQ ID NO:44 to SEQ ID NO:49 and SEQ ID NO:52 to SEQ ID NO:62. Gap in the alignment is indicated by "−". Bases are highlighted by four different shades of grey. A and B-box are denoted by black squares. Alignment is showing sequence variation within the members of same family of SINE.

Example 16

This example demonstrates that SINE sequences from evolutionary distant species act as effector domain in antisense functional nucleic acid molecules with translation up-regulation activity.

As shown in FIG. 16A, SINE sequences from evolutionary distant species and with defined secondary structures (Sun et al. (2006) "Common evolutionary trends for SINE RNA structures" Trends in Genetics, Vol. 23, No., 1, pp. 26-33) were selected for the analysis. These sequences display poor sequence identity by alignment analysis. The sequence listing includes RNA sequences corresponding to the DNA sequences shown in FIG. 16A (SEQ ID NO:24 to SEQ ID NO:33). The sequence listing also includes the inverted RNA sequences (SEQ ID NO:34 to SEQ ID NO:43). In FIG. 16B, HEK 293T/17 cells were transfected with eGFP expressing plasmid in combination with an empty vector (−), or SINEUP-GFP with original inverted SINE sequence (dark blue, B2) or with the indicated Effector Domain swapping mutants, cloned in direct and inverted orientation, as indicated. GFP autofluorescence was recorded using CeligoS automated imaging system. Data indicate the results of GFP fluorescence normalized to empty vector (pCDNA3.1) transfected cells (N>7 replicas). Data indicate mean+stdev. The framed columns show conditions where SINEUP activity is enhanced as compared to SINE B2 positive control. As shown in FIG. 16C, qRT-PCR analysis indicate that protein up-regulation occurs with stable GFP mRNA levels (post-transcriptional). After the Celigo S measurement, RNAs were extracted and purified. GFP mRNAs and SINEUP-GFP RNAs were analyzed qRT-PCR with specific primers. N=3, SINE B2 is set to 1.

Example 17

This example demonstrates that more potent translation up-regulation activity of SINE sequences from evolutionary distant species correlates with more complex secondary structures (combinations of stem loops).

Figure 17:
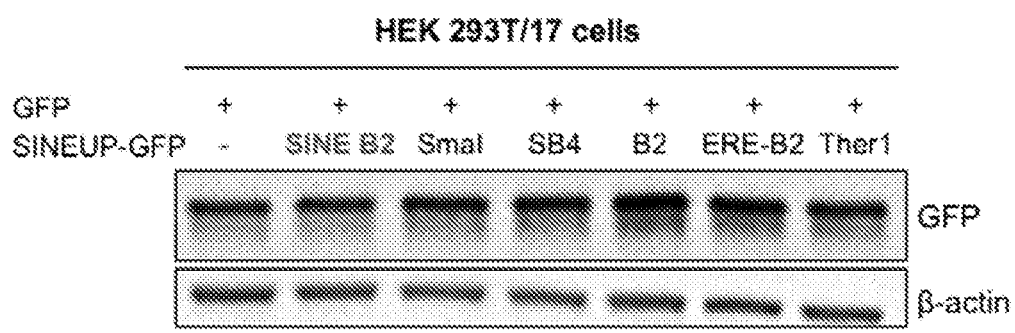
FIG. 17 related to Example 17 shows the correlation between more potent translation up-regulation activity of SINE sequences from evolutionary distant species and more complex structures.
Figure 17:
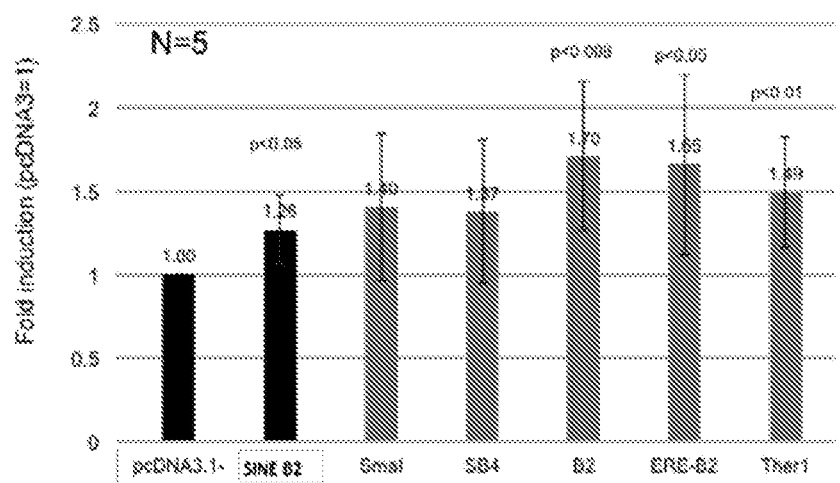
Figure 17:
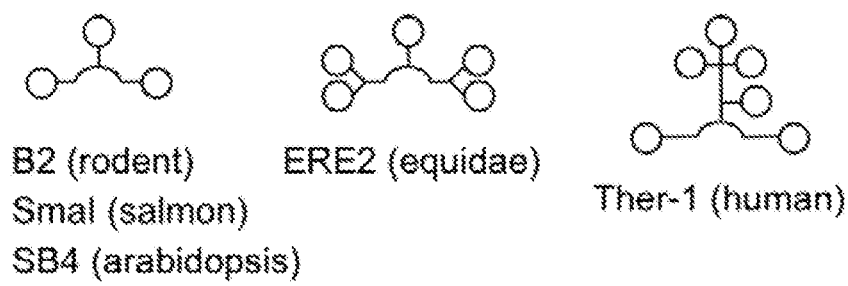

In FIG. 17A, HEK 293T/17 cells were transfected with eGFP expressing plasmid in combination with an empty vector (−), or SINEUP-GFP with original inverted SINE sequence (SINE B2) or with the indicated Effector Domain swapping mutants. Western blot analysis was performed with anti-GFP antibody to monitor overexpressed protein. β-actin was used as loading control. In FIG. 17B, GFP protein quantities were calculated by image analysis, upon normalization to β-actin control. Data from N=5 replicas are represented as mean±stdev. Statistical analysis was performed using t-test (p values shown). FIG. 17C shows the most active SINEs from various species, with their relative structure. Overall SINE structures are represented with lines (stems) and circles (hairpin loops). It should be noted that all of the most active SINEs share a conserved apical stem loop structure. Indeed, this stem-loop structure is shown to be a key element for translation up-regulation activity in SINEs of evolutionary distant species.

Example 18

This example demonstrates that structural motifs (motif 1, IL-3/SL-3 and motif 2, SL-1) are shared between the more potent SINE sequences in functional nucleic acid molecules.

Figure 18:
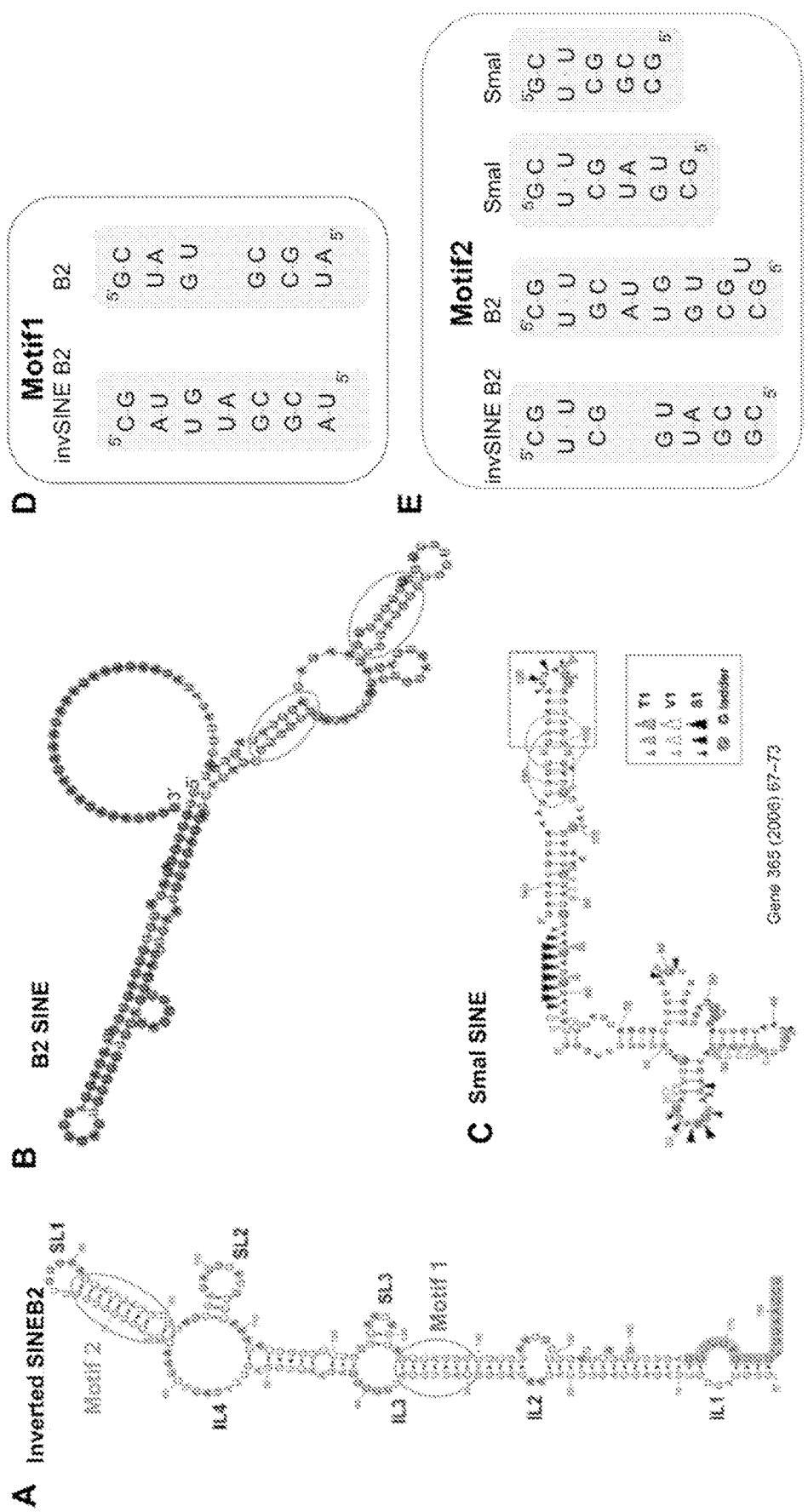
FIG. 18 related to Example 18 shows 2D structure motif analysis of SINE sequences from evolutionary distant species. The sequence of panel A is SEQ ID NO:5. The sequence of panel B is SEQ ID NO:30. The sequence of panel C is SEQ ID NO:92.

FIG. 18 shows the 2D structure motif analysis of SINE sequences from evolutionary distant species that have translation up-regulation activity in functional nucleic acid molecules. FIG. 18A shows the 2D structure of inverted SINE B2 RNA from example 2 (SEQ ID NO:5). FIG. 18B shows the predicted 2D structure of B2 consensus SINE RNA (SEQ ID NO:30) determined by RNA fold WebServer with default settings. FIG. 18C shows the 2D structure of SmaI SINE RNA (SEQ ID NO:27) using enzymatic probing. The putative recognition region for LINE RT are boxed by dashed line (H Kawagoe-Takaki et al. Gene 365 (2006), 67-73). FIG. 18D shows the stem structure Motif1 (intermediate stem, IL-3, SL-3) from 2D structure of inverted SINE B2 and B2 SINE. Motif 1 structures stem between middle loop structures. FIG. 18E shows the stem structure Motif2 (SL-1) from 2D structure of inverted SINE B2, B2 SINE and SmaI SINE. Motif2 structures stem close to the edge loop structure.

Again it is noted that the three structures in FIGS. 18A, 18B and 18C share a conserved apical stem loop structure.

Example 19

Figure 19:
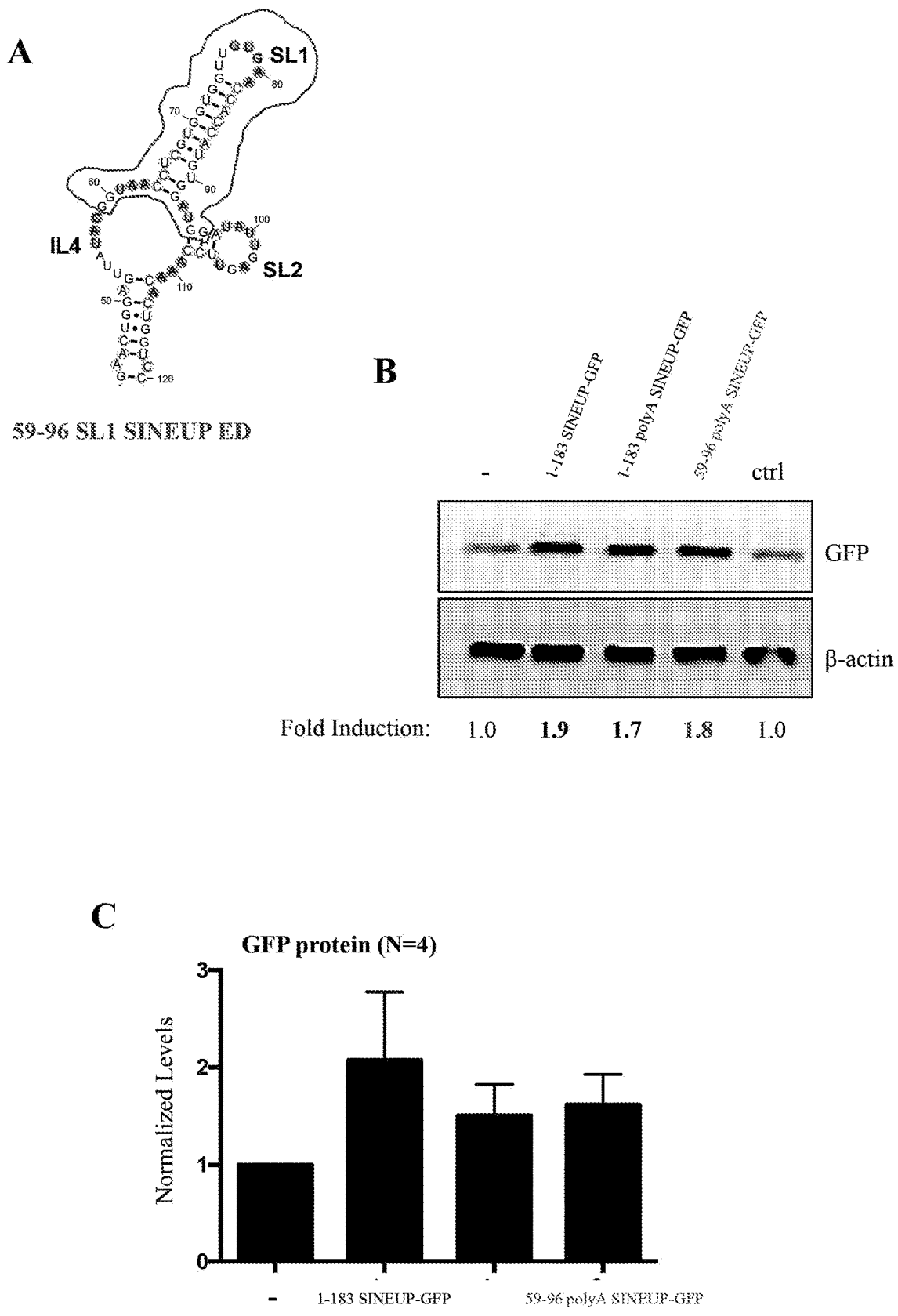
FIG. 19 related to Example 19 shows that the first stem loop domain (SL-1) is sufficient for translation up regulation activity of antisense lncRNA overlapping with GFP mRNA (59-96 SL1 SINEUP-GFP) in HEK 293T/17 cells. The sequence of panel A is SEQ ID NO:7.

This example demonstrates that new synthetic effector domain sequences can be designed based on structural features (38 nt, stem loop structure SL1) and that these possess translation up-regulation activity in functional nucleic acid molecule with overexpressed mRNA. Activity is obtained with different primary nucleotide sequence, but same structure. In particular, a shorter and structure-based variant of the inverted SINE B2 displays translation up-regulation activity as effector domain functional nucleic acid molecule targeting endogenous mRNA (59-96 SL1 SINEUP-GFP). FIG. 19A is a schematic representation of structure based mutations annotated on inverted SINE B2 secondary structure highlighting SL1 (59-96 nt corresponds to SEQ ID NO:12). FIG. 19B shows translation up-regulation activity of functional nucleic acid molecules targeting endogenously expressed GFP mRNA in which the effector domain is a shorter synthetic sequence with conserved structural features (38 nt SL1). HEK 293T/17 cells were transfected with eGFP expressing plasmid in combination with an empty vector (−), or 1-183 SINEUP-GFP (including SEQ ID NO:5), 1-183 SINEUP-GFP polyA (SEQ ID NO:63) and SL1 59-96 polyA SINEUP-GFP (SEQ ID NO:64), as indicated. Western blot was performed with anti-GFP antibody to monitor overexpressed protein. β-actin was used as loading control. Fold-induction was calculated on Western blot images normalized to β-actin and relative to empty control samples. Data from 4 independent experiments are shown in FIG. 19C. SL1 SINEUP-GFP translation enhancer activity is indicated in red. Data indicate mean±st. dev.

This experiment shows that the first stem loop domain (SL-1) is sufficient for translation up regulation activity of antisense lncRNA overlapping with GFP mRNA (59-96 SL1 SINEUP-GFP) in HEK 293T/17 cells.

Example 20

Figure 20:
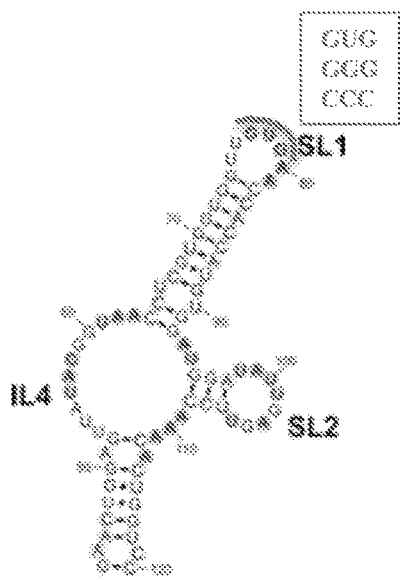
FIG. 20 related to Example 20 shows that a structure-based shorter version of the inverted SINE B2 is sufficient for translation up regulation of antisense lncRNA overlapping with GFP mRNA (44-120 SINEUP-GFP) in HEK 293T/17 cells by Western blot. The sequence of panel A is SEQ ID NO:7.
Figure 20:
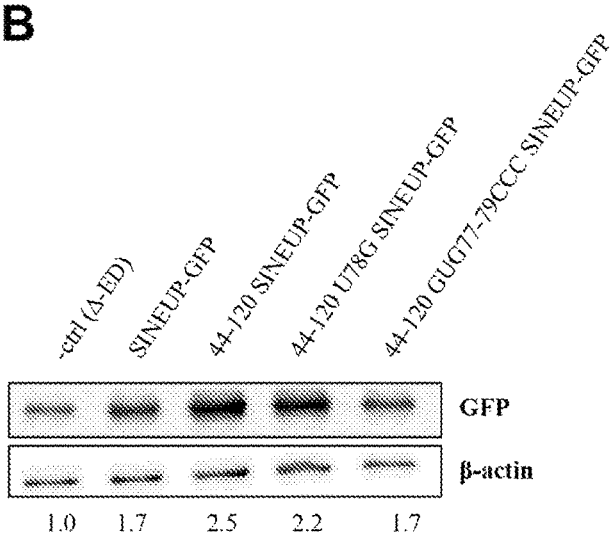

This example demonstrates that new synthetic effector domain sequences can be designed based on structural features (44-120 nt SINEUP, containing IL4, SL1 and SL2 and corresponding to SEQ ID NO:7) and that they possess translation up-regulation activity in functional nucleic acid molecule with overexpressed mRNA. Activity is obtained with different primary nucleotide sequence, but same structure. In particular, a shorter and structure-based variant of the inverted SINE B2 displays translation up-regulation activity as effector domain functional nucleic acid molecule targeting endogenous mRNA. Furthermore, the mutation U78G within the SINEUP with the truncated inverted SINE B2 element 44-120 maintains a similar translational up-regulation activity while the triple mutation GUG77-79CCC diminishes considerably the activity proving the functional importance of nucleotides 77-79. FIG. 20A is a schematic representation of structure based mutations annotated on the truncated inverted SINE B2 secondary structure highlighting the wild type and mutated sequences (44-120 with U78G corresponds to SEQ ID NO:65; 44-120 with GUG77-79CCC corresponds to SEQ ID NO:66). FIG. 20B shows translation up-regulation activity of functional nucleic acid molecules targeting endogenously expressed GFP mRNA in which the effector domain is a shorter synthetic sequence with wt or mutated sequences in 77-79 nucleotides positions. HEK 293T/17 cells were transfected with eGFP expressing plasmid in combination with an empty vector (−), or 44-120 SINEUP-GFP, 44-120 SINEUP-GFP with U78G and 44-120 SINEUP-GFP with GUG77-79CCC. Western blot was performed with anti-GFP antibody to monitor overexpressed protein. β-actin was used as loading control. Fold-induction was calculated on Western blot images normalized to β-actin and relative to empty control samples. 44-120 SINEUP-GFP activity was similar both to the SINEUP-GFP activity with the entire inverted SINE B2 sequence and to the 44-120 SINEUP-GFP with the truncated 44-120 effector domain with the U78G mutation. By comparison, 44-120 SINEUP-GFP with GUG77-79CCC displayed a reduced activity.

This experiment shows that a structure-based shorter version of the inverted SINE B2 is sufficient for translation up regulation of antisense lncRNA overlapping with GFP mRNA (44-120 SINEUP-GFP) in HEK 293T/17 cells. It also shows that nucleotides 77-79 of the inverted SINE B2 sequences are important for the ability to up-regulate translation. All three constructs are functional and the secondary structure presents in an optimal manner the three nucleotides of the 77-79 loop. Even if these three nucleotides are modified, the molecule retains functions.

Example 21

This example demonstrates that new synthetic effector domain sequences can be designed based on structural features (44-120 nt SINEUP, containing IL4, SL1 and SL2 corresponds to SEQ ID NO:7) and that they possess translation up-regulation activity in functional nucleic acid molecule with endogenously expressed mRNA. Activity is obtained with different primary nucleotide sequence, but same structure. In particular, a shorter and structure-based variant of the inverted SINE B2 displays translation up-regulation activity as effector domain functional nucleic acid molecule targeting endogenous mRNA. Furthermore, structure based mutations annotated on the truncated inverted SINE B2 secondary structure can increase the translational activator ability (a 44-120 SINEUP-DJ-1 variant with 6 point mutations: A45G; U48C; U66G; U88C; U90O; U115O in the truncated inverted SINE B2 sequence and called 44-120 SINEUP-DJ-1-Strong corresponding to SEQ ID NO:67) while other structure based mutations annotated on the truncated inverted SINE B2 secondary structure can keep the translational up-regulation ability unchanged or lower (a 44-120 SINEUP-DJ-1 variant with 5 point mutations: G49A; U66A; G68A; G116A; C119A in the truncated inverted SINE B2 sequence and called 44-120 SINEUP-DJ-1-Weak corresponding to SEQ ID NO:68). The rationale behind the design of the two variants is that, according to the structure of the 44-120 SINEUP, in the two stretches of dsRNA (44-50 with 114-120 and 64-74 with 82-92) there are 5 base pairs mismatches (45-119; 48-116; 49-115; 66-90; 68-88). In 44-120 SINEUP Strong, mutant base pairs have been designed to establish G:C pairs. In 44-120 SINEUP Weak, mutant base pairs have been designed to establish U:A pairs. Since G:C pairs are more stable due to, among other factors, the formation of three versus two hydrogen bonds, the mutant 44-120 SINEUP with 5 G:C pairs has been indicated as Strong while the mutant 44-120 SINEUP with 5 U:A pairs has been indicated as weak.

Figure 21:
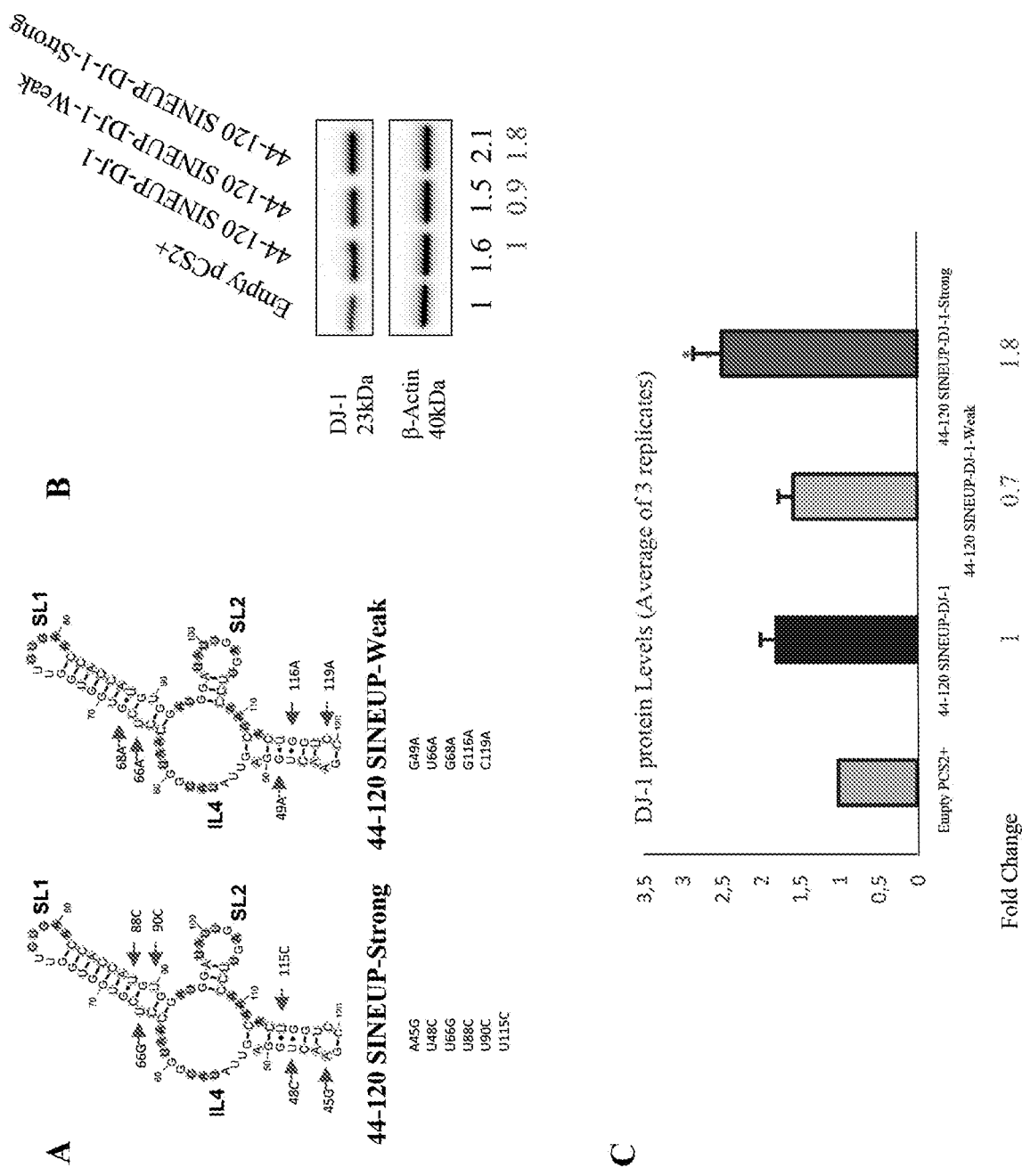
FIG. 21 related to Example 21 shows that a structure-based shorter version of the inverted SINE B2 is sufficient for translation up regulation of antisense lncRNA overlapping endogenous DJ-1 mRNA (44-120 SINEUP-DJ-1) in HEK 293T/17 cells. The function of two variants with point mutations has also been tested. The sequences of panel A are both SEQ ID NO:7.
Figure 22:
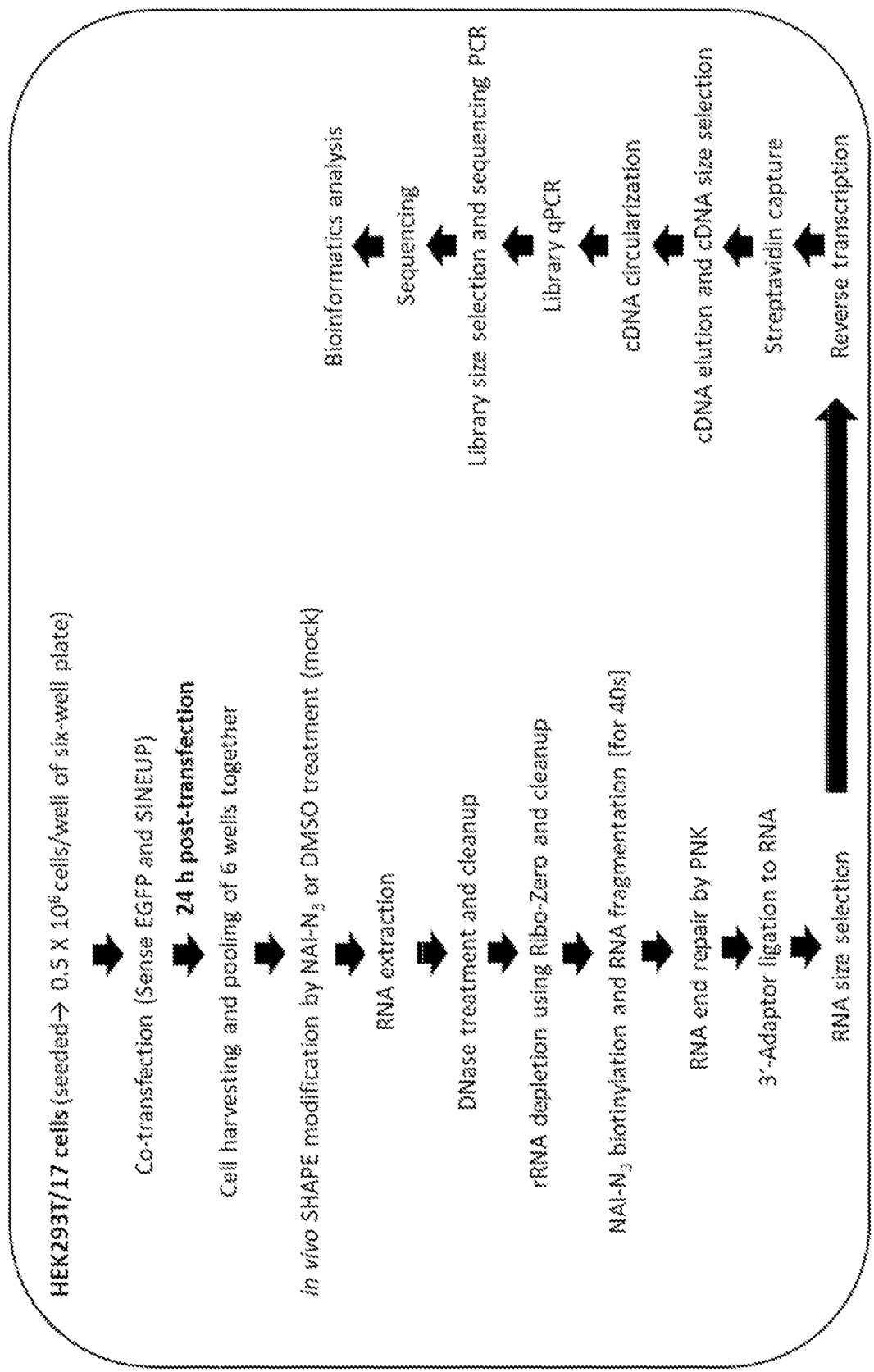
FIG. 22 shows a schematic overview of the SINEUP-icSHAPE experiment.

FIG. 21A is a schematic representation of structure based mutations annotated on the truncated inverted SINE B2 secondary structure for 44-120 SINEUP-DJ-1-Strong and 44-120 SINEUP-DJ-1-Weak. The positions of mutations are indicated by arrows. FIG. 21B shows translation up-regulation activity of functional nucleic acid molecules targeting endogenously expressed DJ-1 mRNA in which the effector domain is a shorter synthetic sequence (44-120 SINEUP-DJ-1) or the same sequence modified with 6 points mutations (44-120 SINEUP-DJ-1-Strong) or 5 point mutations (44-120 SINEUP-DJ-1-Weak). HEK 293T/17 cells were transfected with eGFP expressing plasmid in combination with an empty vector (−), or 44-120 SINEUP-DJ-1, 44-120 SINEUP-DJ-1-Strong and 44-120 SINEUP-DJ-1-Weak. Western blot was performed with anti-DJ-1 antibody to monitor overexpressed protein. β-actin was used as loading control. Fold-induction was calculated on Western blot images normalized to β-actin and relative to empty control samples. Data from 3 independent experiments are shown in FIG. 21C. 44-120 SINEUP-DJ-1 activity was similar to 44-120 SINEUP-DJ-1-Weak while 44-120 SINEUP-DJ-1-Strong was higher in a statistically significant manner. Data indicate mean±st. dev.

This experiment shows that a structure-based shorter version of the inverted SINE B2 is sufficient for translation up regulation (44-120 SINEUP-DJ-1). Furthermore, 44-120 SINEUP-DJ-1-Strong presents higher translational activator activity with respect to 44-120 SINEUP-DJ-1. 44-120 SINEUP-DJ-1-Weak presents a translational up-regulation activity similar or lower than 44-120 SINEUP-DJ-1.

Example 22

FIG. 23A shows icSHAPE data guided secondary structure of AS Uchl1 SINEB2 in miniSINEUP-GFP. icSHAPE enrichment score data was used as soft constraint in RNAfold tool of ViennaRNA. Linear mapping method was used to derive pairing probabilities and method described by Zarringhalam et al. (2012) (Zarringhalam et al. (2012) "Integrating Chemical Footprinting Data into RNA Secondary Structure Prediction" PLOS ONE, Vol. 7, No. 10, Article e45160 (13 pages)) was selected to incorporate guiding pseudo energies into folding algorithm. To draw the secondary structure forna server was used. Dark dot, icSHAPE enrichment score ≥0.8; light dot, enrichment score 0.5-0.8. Enrichment scores are scaled on 0 to 1 scale where 1 indicates high probability for a nucleotide to be in unpaired state and 0 for tendency of being paired. B-box and A-box regions of SINEB2 are marked with lines (respectively in higher part of the Figure and lower part of the Figure). Sequence and icSHAPE-guided 2D structure of all of the SINEB2s functionally tested in this study were pairwise compared to this structure and sequence of AS Uchl1 SINEB2 using ExpaRNA tool (Heyne, S. et al. Bioinformatics, 2009, 25:2095-2102) which computes the exact matching sequence-structure motifs common to two RNAs. Thus derived motif files from all of the pairwise comparisons were then screened to extract the positions of AS Uchl1 SINEB2 which were present in one or multiple motifs of at least 2mer in length in all of the comparisons. The position of similar sequence and structure motifs shared among all of the SINEB2s are indicated with squares with their corresponding motif number. As 2mers and longer motifs were taken into account to identify the common regions and SINEB2 sequence are highly variable, in most of the cases only partial match could be found. FIG. 23B shows a zoomed in view of common sequence and structure motifs shown in FIG. 23A. It is to be noted that motifs 2 and 3, and motifs 4, 5, 6 and 7 are similar and mainly composed of AGG and UGG trinucleotides respectively. The different motif no. is assigned based on their sequence and structure neighborhood and position on SINEB2. Due to their similar sequence composition, sometimes one hit in query sequence matches to multiple motifs, or one motif matches to multiple positions in the query sequence.

Example 23

Figure 24:
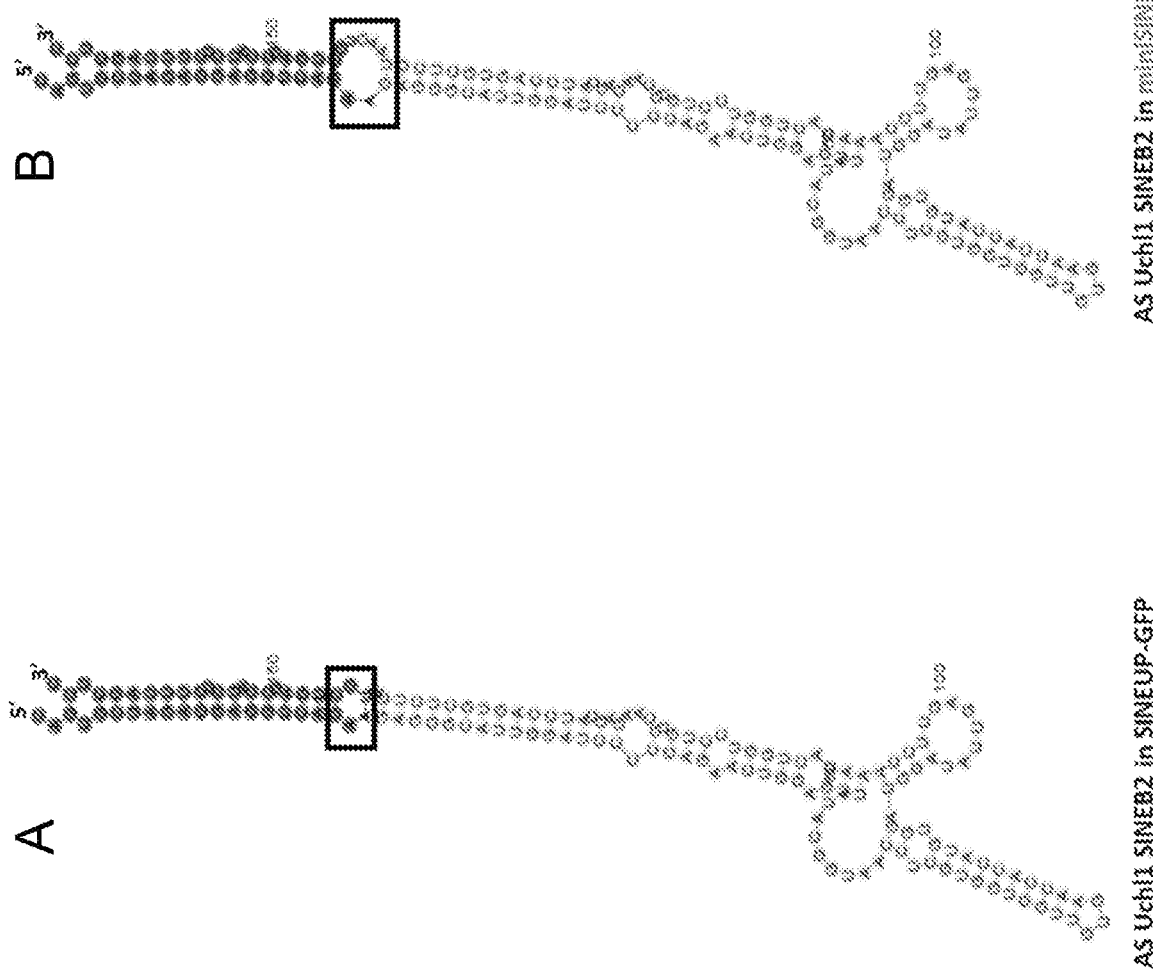
FIG. 24 shows a comparison of 2D structures of AS Uchl1 SINEB2 (A) in long SINEUP-GFP and (B) in miniSINEUP-GFP using ExpaRNA. The sequence of panel A is SEQ ID NO:44. The sequence of panel B is SEQ ID NO:44.

FIG. 24 shows a comparison of 2D structures of AS Uchl1 SINEB2 (A) in SINEUP-GFP and (B) in miniSINEUP-GFP using ExpaRNA. Different shaded regions indicate corresponding exact match of sequence and structure between two RNAs. The AS Uchl1 SINEB2 2D structure in and miniSINEUP-GFP is almost identical which suggests that this structure is highly stable and dominant inside the cell. The only region of structure variation is marked with a black rectangle.

Example 24

Figure 25:
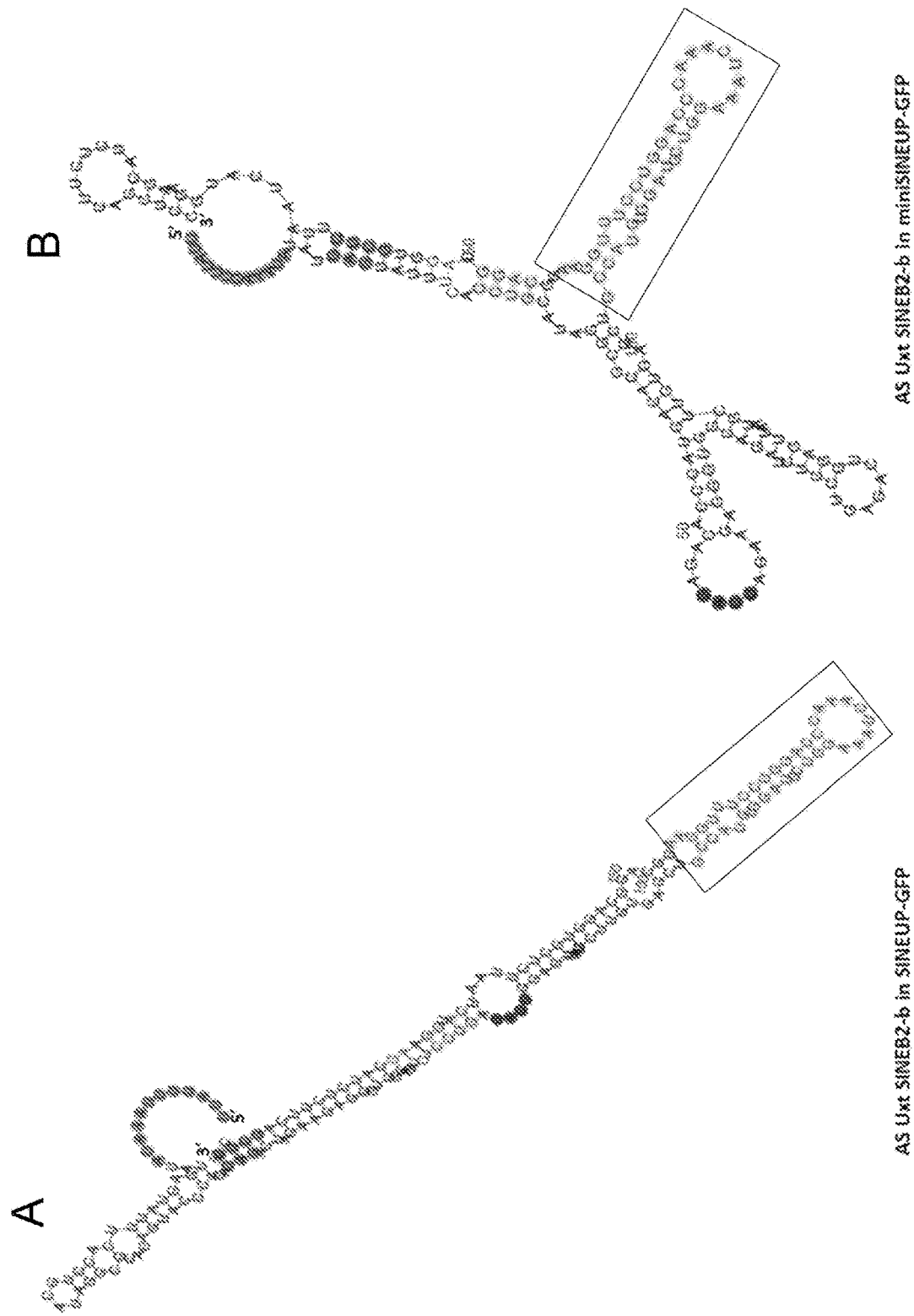
FIG. 25 shows ExpaRNA exact pattern match result for 2D structures of AS Uxt SINEB2-b (A) in long SINEUP-GFP and (B) in miniSINEUP-GFP. The sequence of panel A is SEQ ID NO:47. The sequence of panel B is SEQ ID NO:47.

FIG. 25 shows ExpaRNA exact pattern match result for 2D structures of AS Uxt SINEB2-b (A) in SINEUP-GFP and (B) in miniSINEUP-GFP. Different shaded regions indicate corresponding exact match of sequence and structure between two RNAs. The overall structure is quite different between SINEUPs and miniSINEUPs here, but some regions preserved the structure (eg.—boxed region) which might be crucial for the SINEUP function.

Example 25

Figure 26:
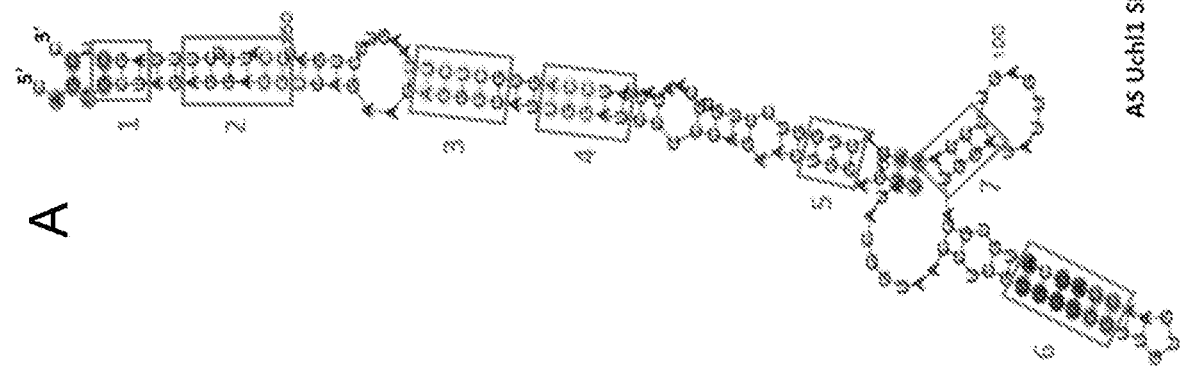
FIG. 26 shows ExpaRNA exact pattern match result for 2D structures of (A) AS Uchl1 SINEB2 in miniSINEUP-GFP and (B) AS Txnip SINEB2 in long SINEUP-GFP. The sequence of panel A is SEQ ID NO:44. The sequence of panel B is SEQ ID NO:45.
Figure 26:
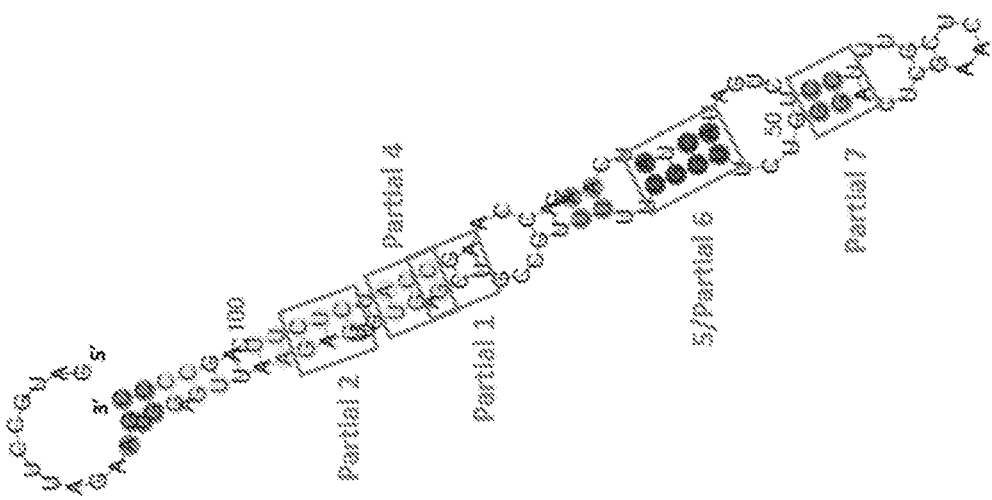

FIG. 26 shows ExpaRNA exact pattern match and motif analysis result for 2D structures of (A) AS Uchl1 SINEB2 in miniSINEUP-GFP and (B) AS Txnip SINEB2 in SINEUP-GFP. Different shaded regions indicate corresponding unique patterns of exact sequence and structure match between two RNAs. The position of similar sequence and structure motifs shared among all of the SINEB2s are indicated with squares with their respective motif numbers. Due to their similar sequence composition, in some instances motifs 2 and 3 may overlap, and same goes for motifs 4, 5, 6, and 7.

Example 26

Figure 27:
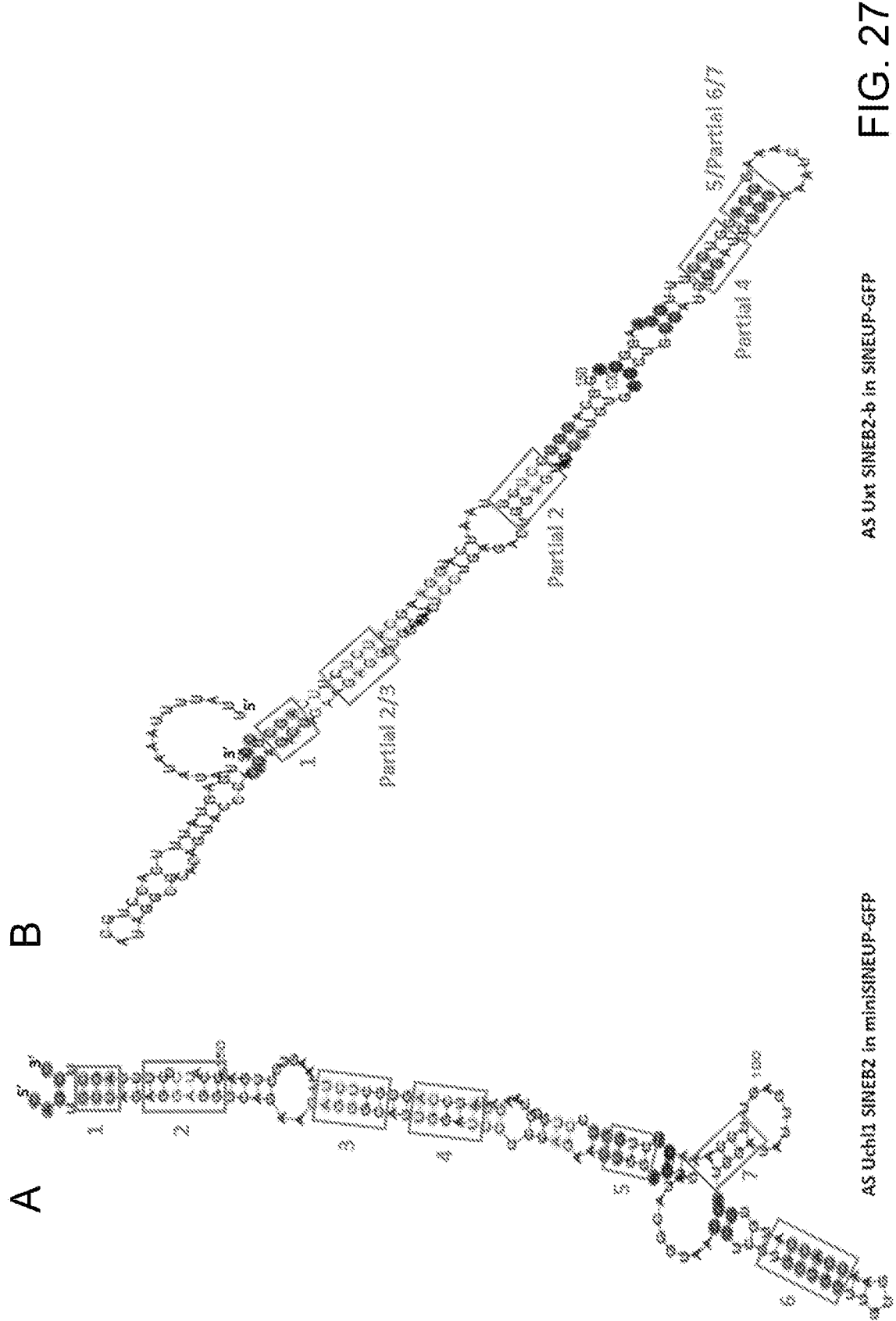
FIG. 27 shows ExpaRNA exact pattern match result for 2D structures of (A) AS Uchl1 SINEB2 in miniSINEUP-GFP and (B) AS Uxt SINEB2-b in long SINEUP-GFP. The sequence of panel A is SEQ ID NO:44. The sequence of panel B is SEQ ID NO:47.

FIG. 27 shows ExpaRNA exact pattern match and motif analysis result for 2D structures of (A) AS Uchl1 SINEB2 in miniSINEUP-GFP and (B) AS Uxt SINEB2-b in SINEUP-GFP. The same as above applies.

Example 27

Figure 28:
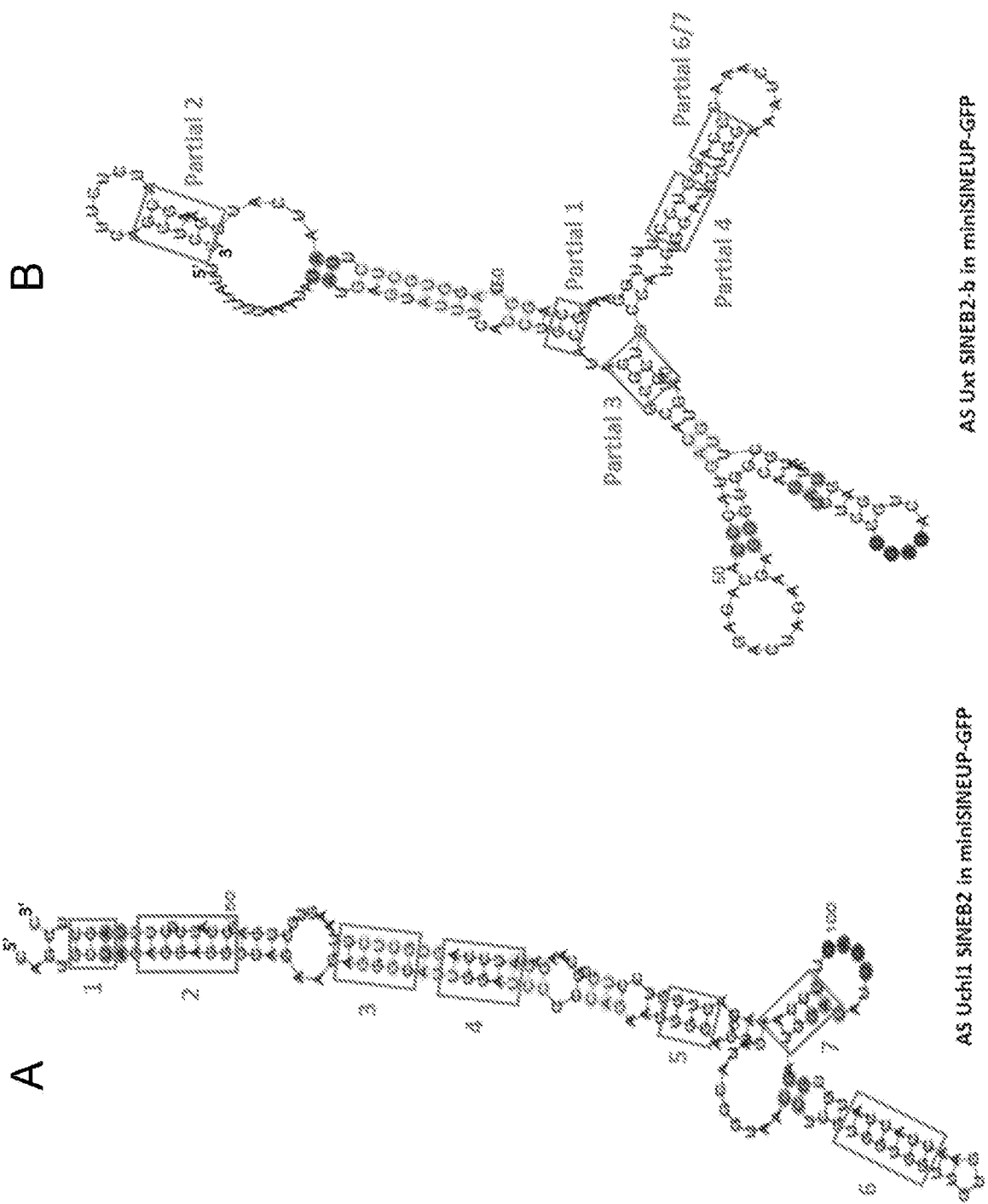
FIG. 28 shows ExpaRNA exact pattern match result for 2D structures of (A) AS Uchl1 SINEB2 in miniSINEUP-GFP and (B) AS Uxt SINEB2-b in miniSINEUP-GFP. The sequence of panel A is SEQ ID NO:44. The sequence of panel B is SEQ ID NO:47.

FIG. 28 shows ExpaRNA exact pattern match and motif analysis result for 2D structures of (A) AS Uchl1 SINEB2 in miniSINEUP-GFP and (B) AS Uxt SINEB2-b in miniSINEUP-GFP. Different shaded regions indicate corresponding unique patterns of exact sequence and structure match between two RNAs. The same as above applies.

Example 28

Figure 29:
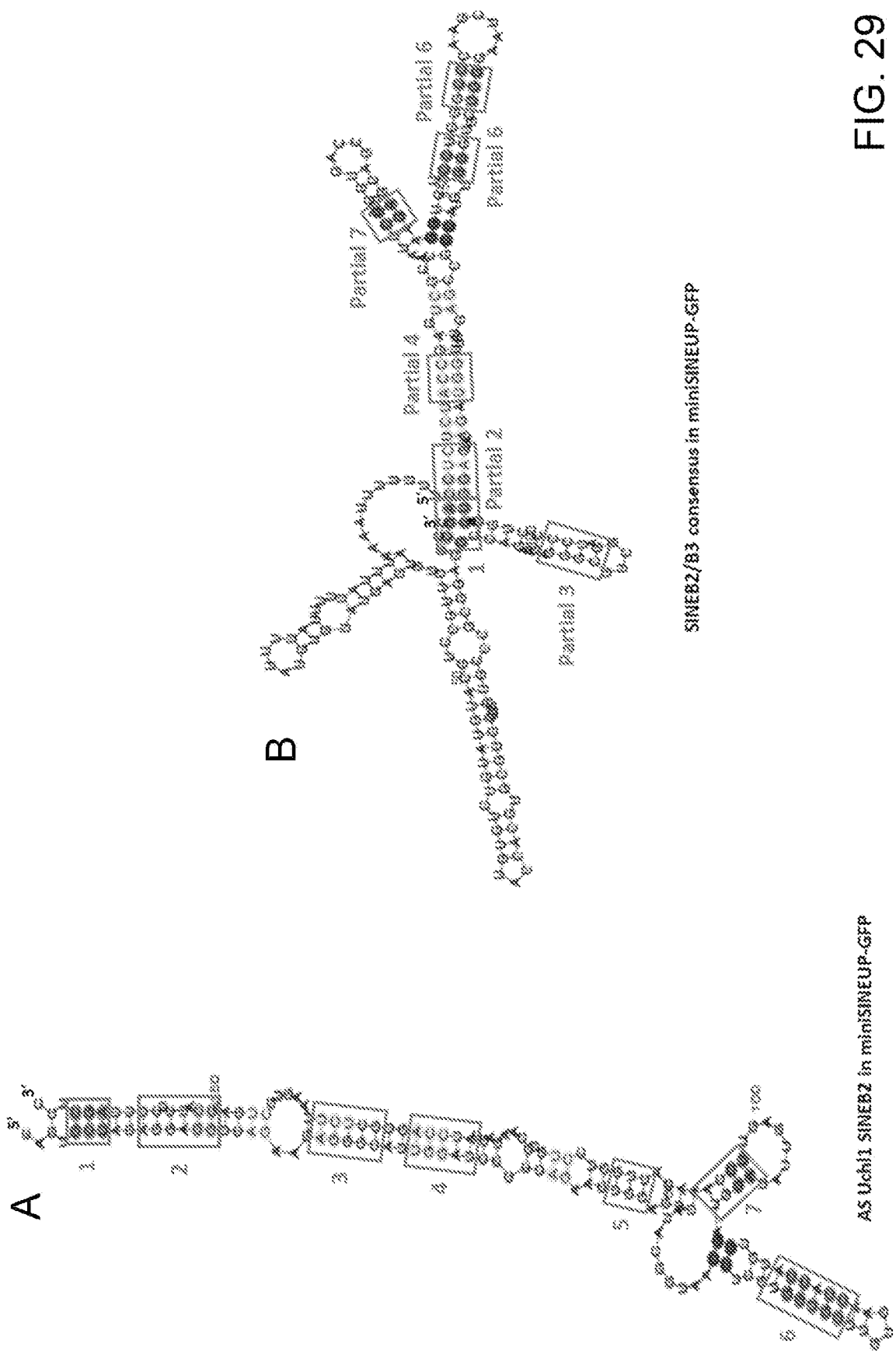
FIG. 29 shows ExpaRNA exact pattern match result for 2D structures of (A) AS Uchl1 SINEB2 in miniSINEUP-GFP and (B) SINEB2/B3 consensus (reverse complement) in miniSINEUP-GFP. The sequence of panel A is SEQ ID NO:44. The sequence of panel B is SEQ ID NO:52.

FIG. 29 shows ExpaRNA exact pattern match and motif analysis result for 2D structures of (A) AS Uchl1 SINEB2 and (B) SINEB2/B3 consensus (reverse complement) in miniSINEUP-GFP. The same as above applies.

Example 29

Figure 30:
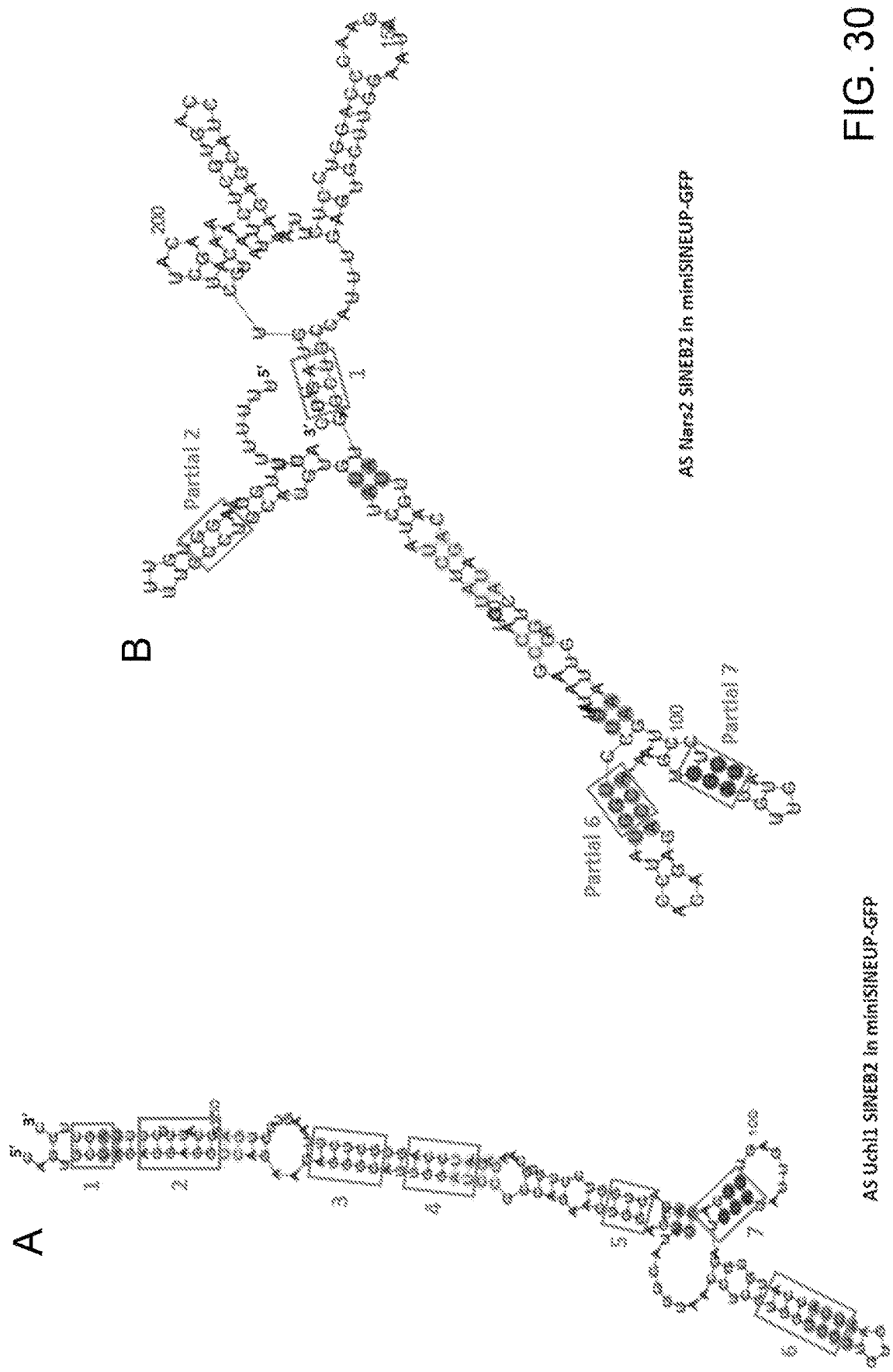
FIG. 30 shows ExpaRNA exact pattern match result for 2D structures of (A) AS Uchl1 SINEB2 in miniSINEUP-GFP and (B) AS Nars2 SINEB2 in miniSINEUP-GFP. The sequence of panel A is SEQ ID NO:44. The sequence of panel B is SEQ ID NO:53.

FIG. 30 shows ExpaRNA exact pattern match and notif analysis result for 2D structures of (A) AS Uchl1 SINEB2 and (B) AS Nars2 SINEB2 in miniSINEUP-GFP. The same as above applies.

Example 30

Figure 31:
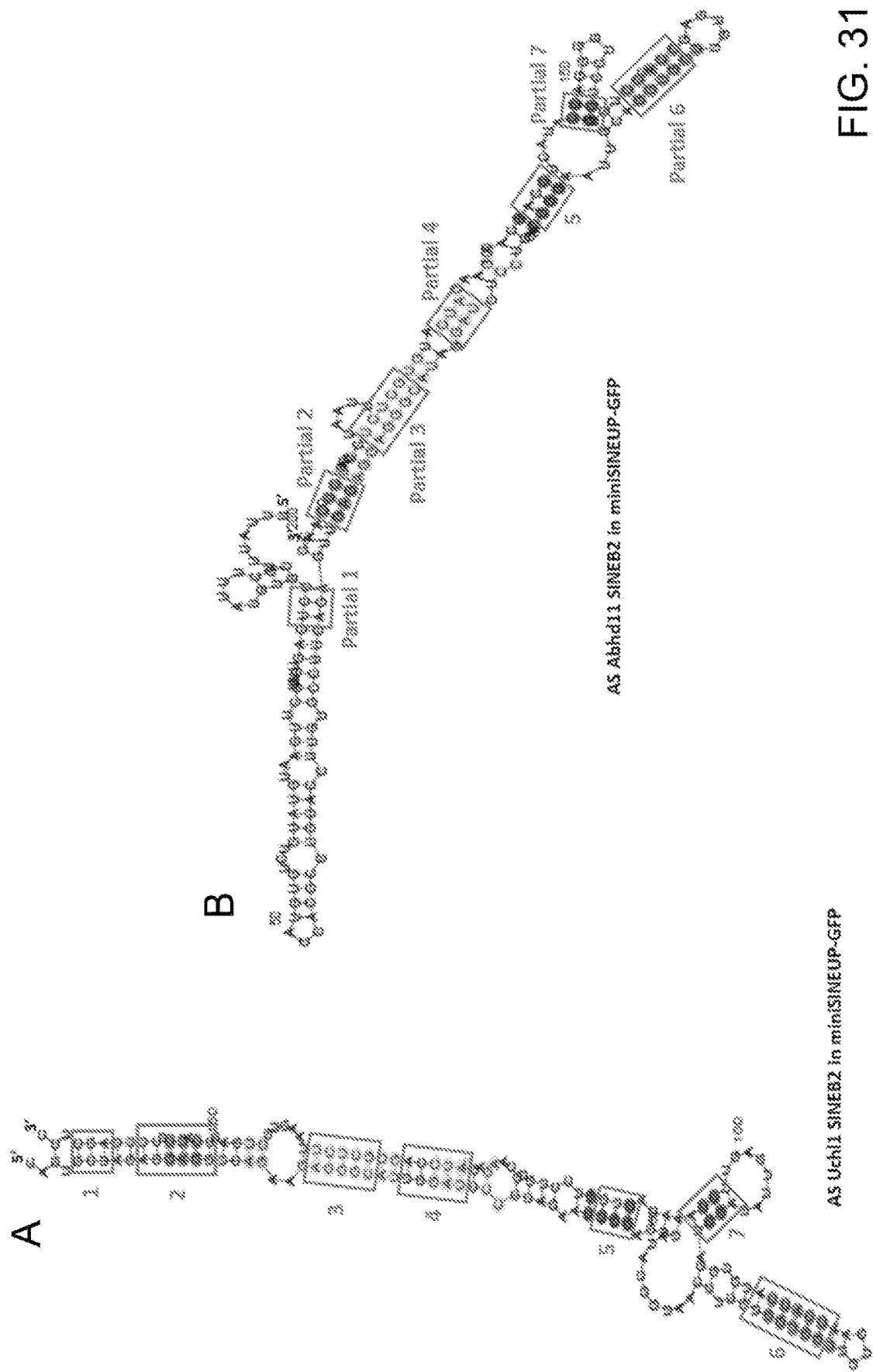
FIG. 31 shows ExpaRNA exact pattern match result for 2D structures of (A) AS Uchl1 SINEB2 in miniSINEUP-GFP and (B) AS Abhd11 SINEB2 in miniSINEUP-GFP. The sequence of panel A is SEQ ID NO:44. The sequence of panel B is SEQ ID NO:54.

FIG. 31 shows ExpaRNA exact pattern match and motif analysis result for 2D structures of (A) AS Uchl1 SINEB2 and (B) AS Abhd11 SINEB2 in miniSINEUP-GFP. The same as above applies.

Example 31

Figure 32:
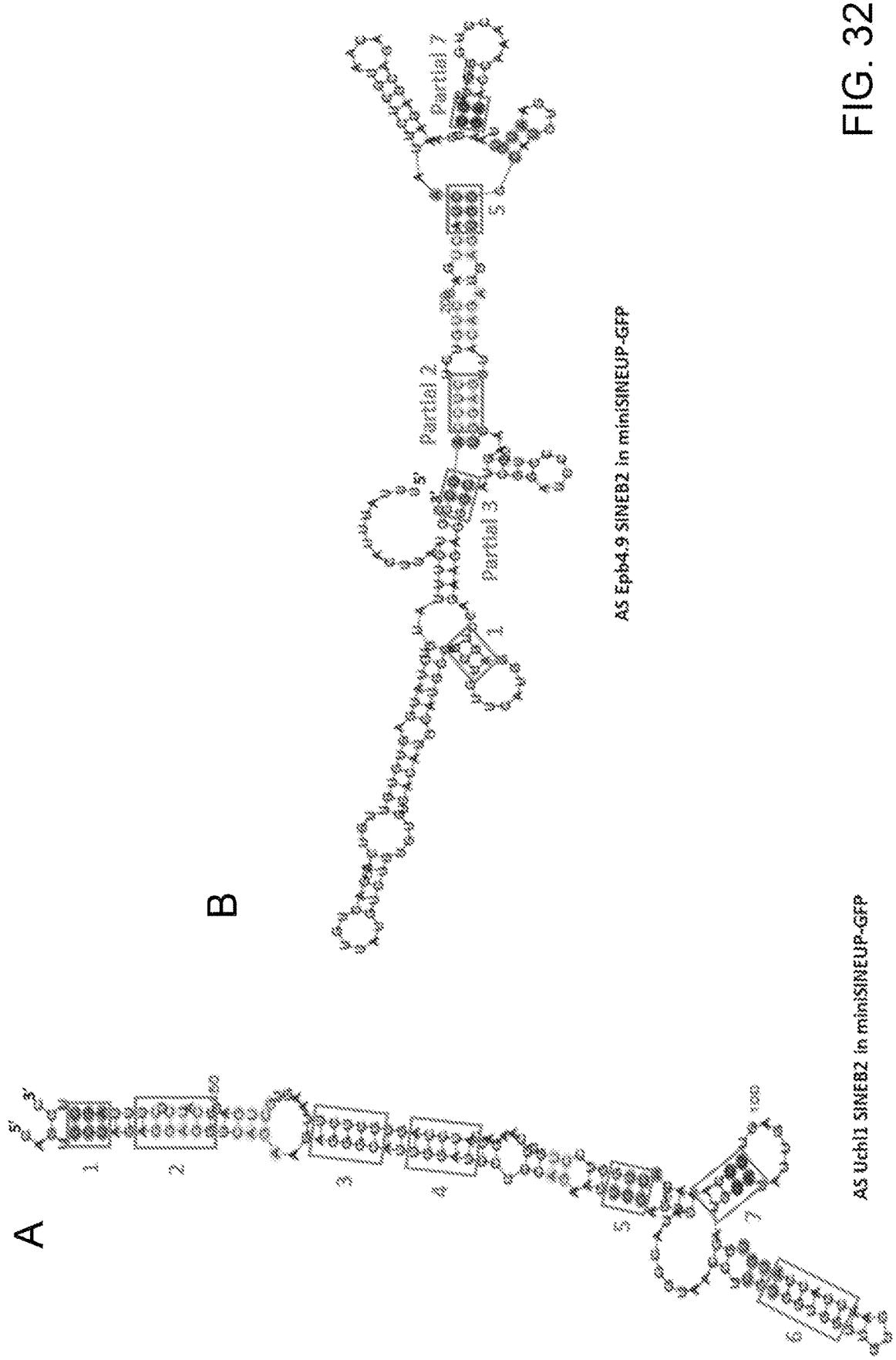
FIG. 32 shows ExpaRNA exact pattern match result for 2D structures of (A) AS Uchl1 SINEB2 in miniSINEUP-GFP and (B) AS Epb4.9 SINEB2 in miniSINEUP-GFP. The sequence of panel A is SEQ ID NO:44. The sequence of panel B is SEQ ID NO:55.

FIG. 32 shows ExpaRNA exact pattern match and motif analysis result for 2D structures of (A) AS Uchl1 SINEB2 and (B) AS Epb4.9 SINEB2 in miniSINEUP-GFP. The same as above applies.

Example 32

Figure 33:
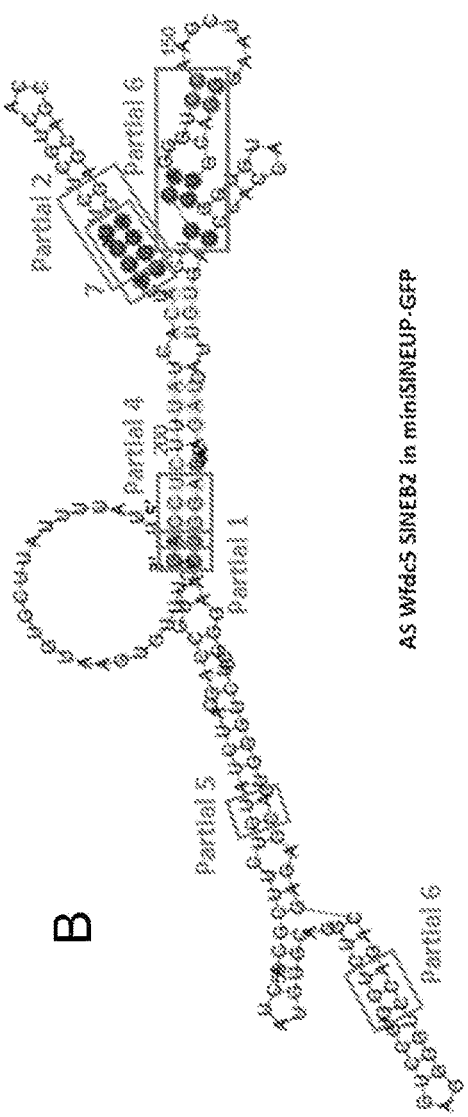
FIG. 33 shows ExpaRNA exact pattern match result for 2D structures of (A) AS Uchl1 SINEB2 in miniSINEUP-GFP and (B) AS Wfdc5 SINEB2 in miniSINEUP-GFP. The sequence of panel A is SEQ ID NO:44. The sequence of panel B is SEQ ID NO:56.
Figure 33:
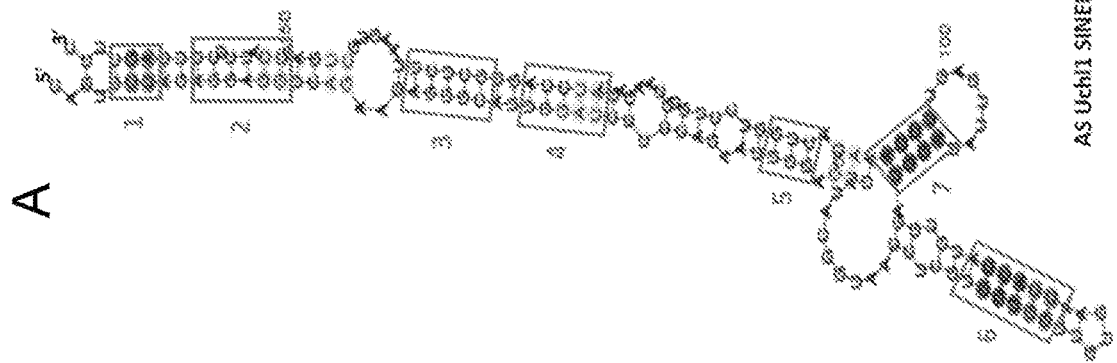

FIG. 33 shows ExpaRNA exact pattern match and motif analysis result for 2D structures of (A) AS Uchl1 SINEB2 and (B) AS Wfdc5 SINEB2 in miniSINEUP-GFP. The same as above applies.

Example 33

Figure 34:
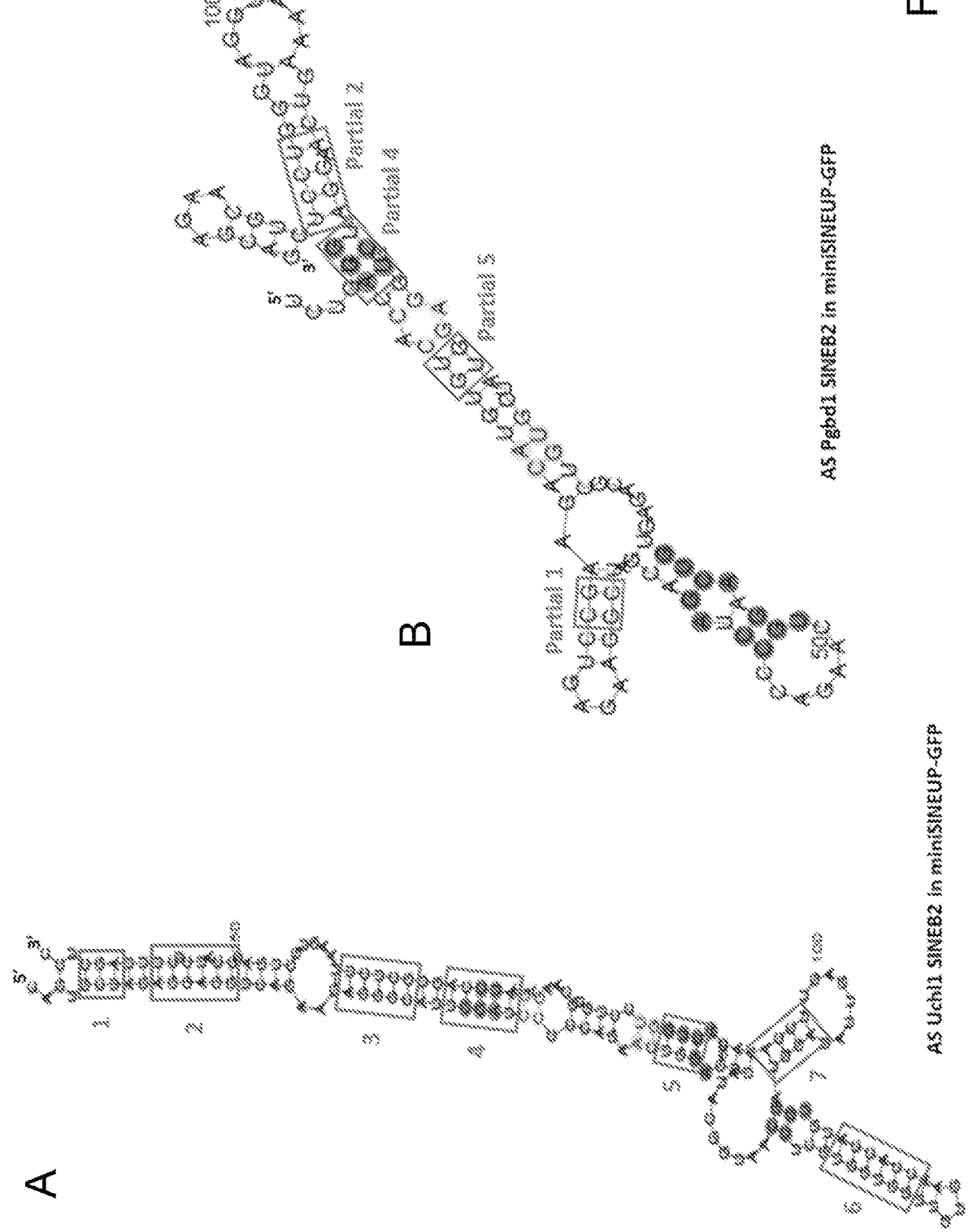
FIG. 34 shows ExpaRNA exact pattern match result for 2D structures of (A) AS Uchl1 SINEB2 in miniSINEUP-GFP and (B) AS Pgbd1 SINEB2 in miniSINEUP-GFP. The sequence of panel A is SEQ ID NO:44. The sequence of panel B is SEQ ID NO:57.

FIG. 34 shows ExpaRNA exact pattern match and motif analysis result for 2D structures of (A) AS Uchl1 SINEB2 and (B) AS Pgbd1 SINEB2 in miniSINEUP-GFP. The same as above applies.

Example 34

Figure 35:
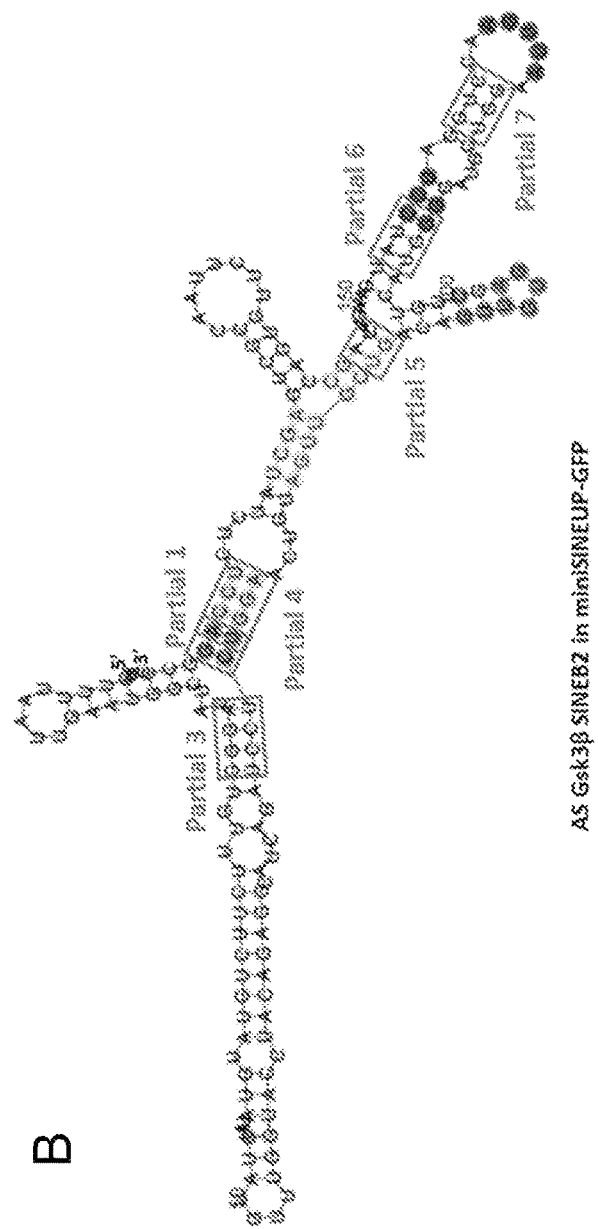
FIG. 35 shows ExpaRNA exact pattern match result for 2D structures of (A) AS Uchl1 SINEB2 in miniSINEUP-GFP and (B) AS Gsk3B SINEB2 in miniSINEUP-GFP. The sequence of panel A is SEQ ID NO:44. The sequence of panel B is SEQ ID NO:58.
Figure 35:
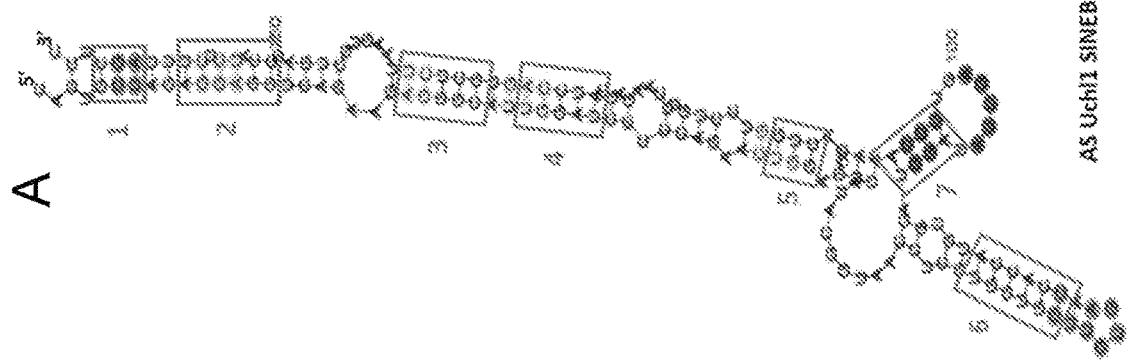

FIG. 35 shows ExpaRNA exact pattern match and motif analysis result for 2D structures of (A) AS Uchl1 SINEB2 and (B) AS Gsk3β SINEB2 in miniSINEUP-GFP. The same as above applies.

Example 35

Figure 36:
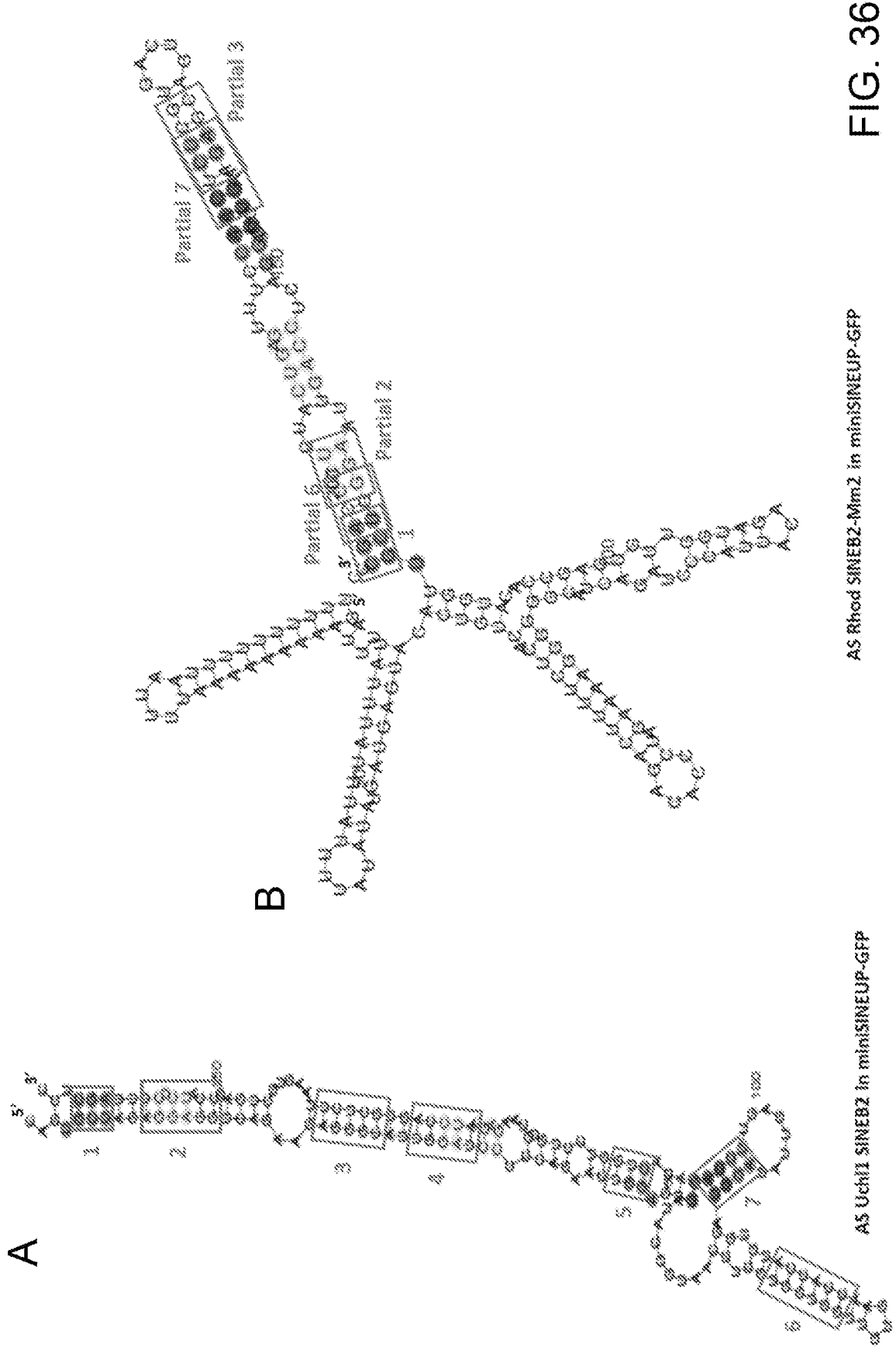
FIG. 36 shows ExpaRNA exact pattern match result for 2D structures of (A) AS Uchl1 SINEB2 in miniSINEUP-GFP and (B) AS Rhod SINEB2-Mm2 in miniSINEUP-GFP. The sequence of panel A is SEQ ID NO:44. The sequence of panel B is SEQ ID NO:59.

FIG. 36 shows ExpaRNA exact pattern match and motif analysis result for 2D structures of (A) AS Uchl1 SINEB2 and (B) AS Rhod SINEB2-Mm2 in miniSINEUP-GFP. The same as above applies.

Example 36

Figure 37:
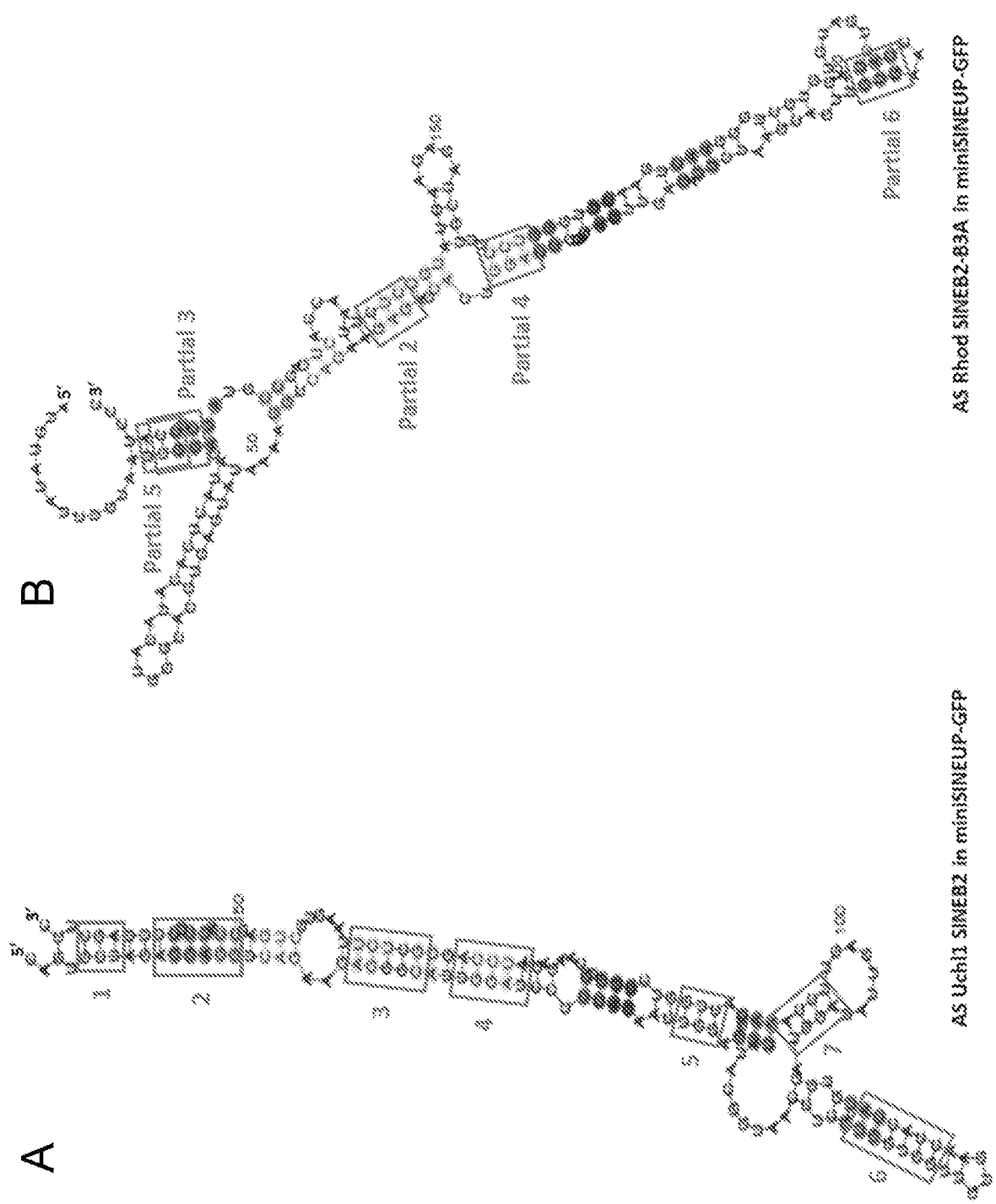
FIG. 37 shows ExpaRNA exact pattern match result for 2D structures of (A) AS Uchl1 SINEB2 in miniSINEUP-GFP and (B) AS Rhod SINEB2-B3A in miniSINEUP-GFP. The sequence of panel A is SEQ ID NO:44. The sequence of panel B is SEQ ID NO:60.

FIG. 37 shows ExpaRNA exact pattern match and motif analysis result for 2D structures of (A) AS Uchl1 SINEB2 and (B) AS Rhod SINEB2-B3A in miniSINEUP-GFP. The same as above applies.

Example 37

Figure 38:
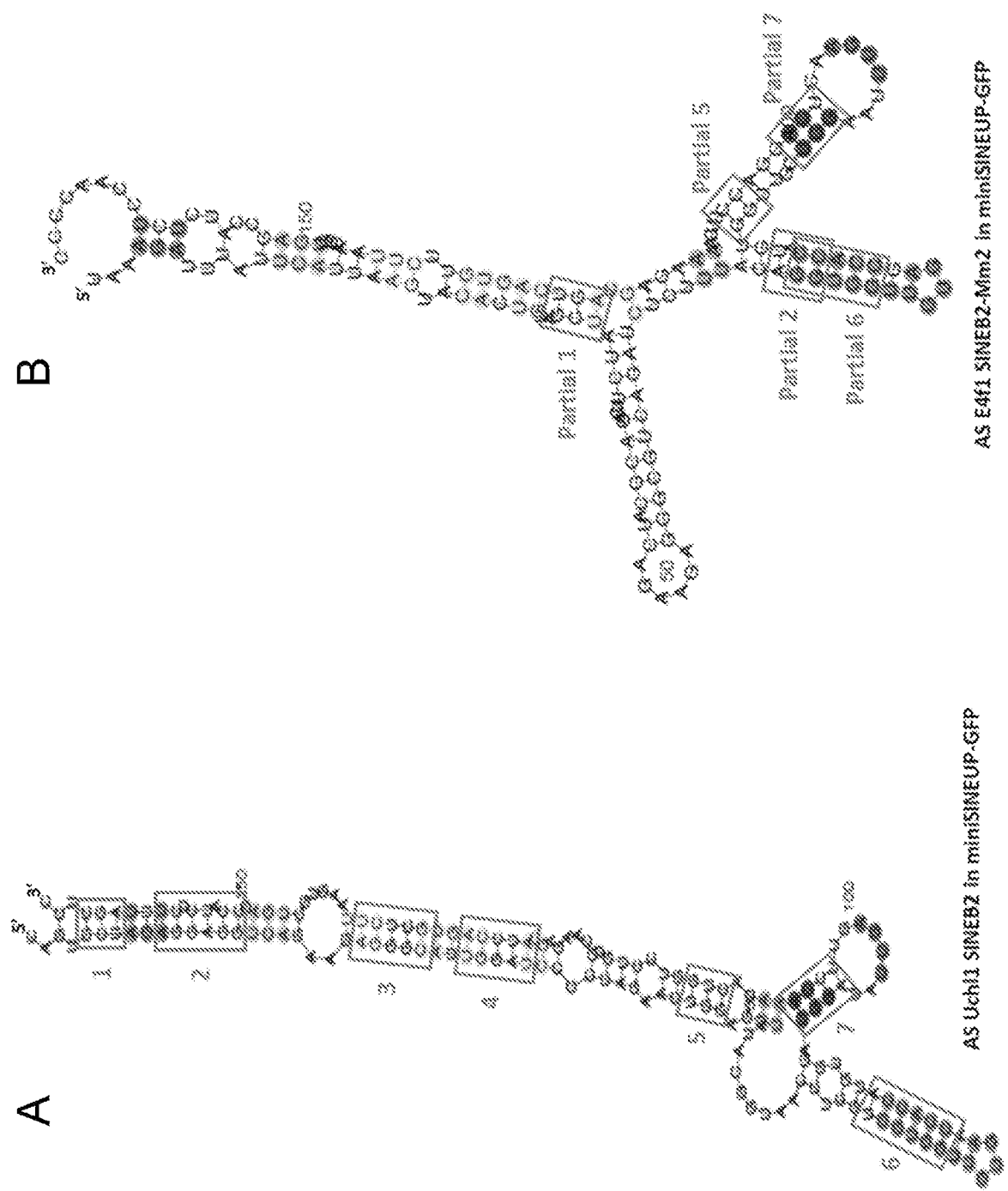
FIG. 38 shows ExpaRNA exact pattern match result for 2D structures of (a) AS Uchl1 SINEB2 in miniSINEUP-GFP and (b) AS E4f1 SINEB2-Mm2 in miniSINEUP-GFP. The sequence of panel A is SEQ ID NO:44. The sequence of panel B is SEQ ID NO:61.

FIG. 38 shows ExpaRNA exact pattern match and motif analysis result for 2D structures of (a) AS Uchl1 SINEB2 and (b) AS E4f1 SINEB2-Mm2 in miniSINEUP-GFP. The same as above applies.

Example 38

Figure 39:
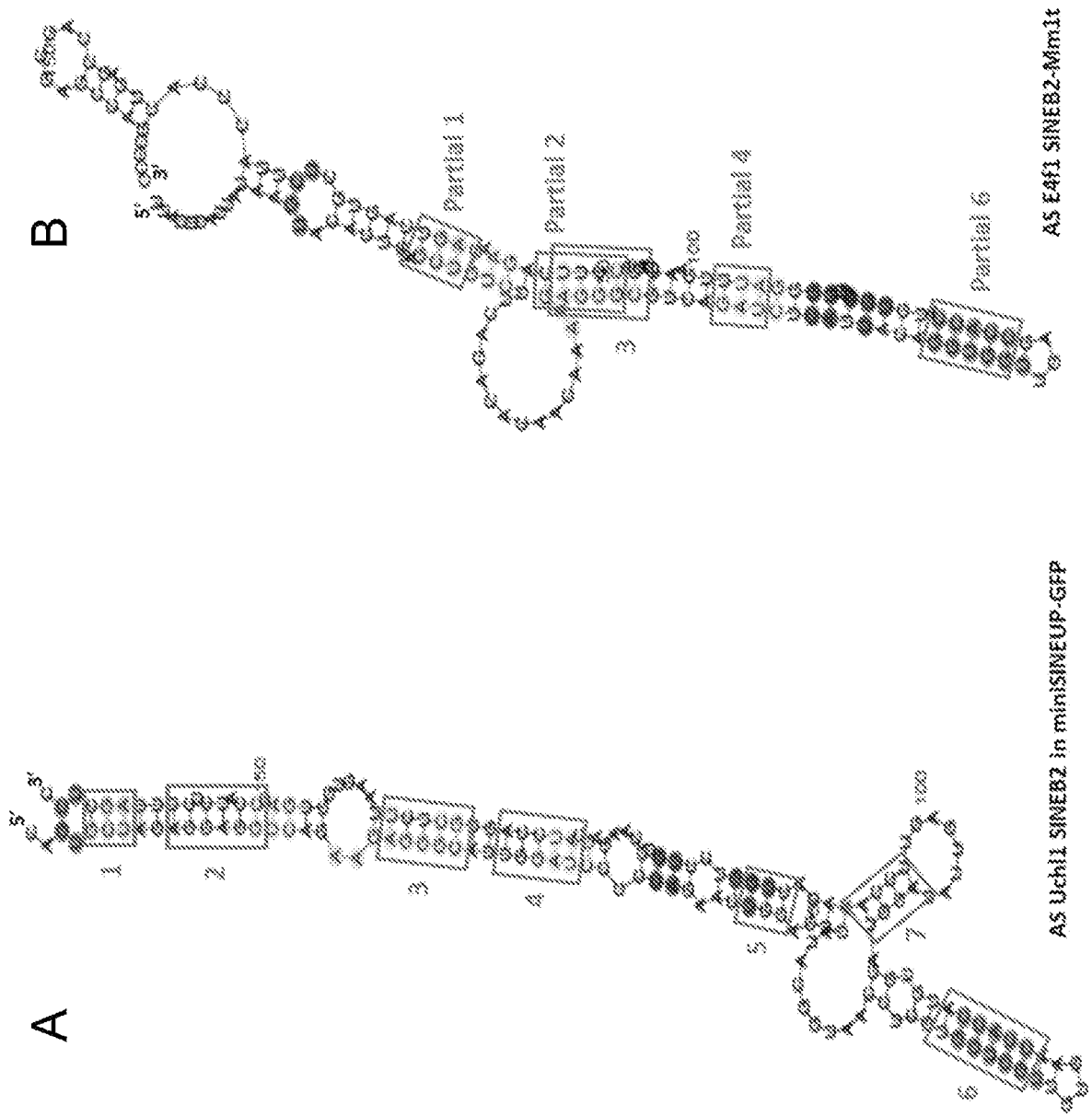
FIG. 39 shows ExpaRNA exact pattern match result for 2D structures of (a) AS Uchl1 SINEB2 in miniSINEUP-GFP and (b) AS E4f1 SINEB2-Mmlt in miniSINEUP-GFP. The sequence of panel A is SEQ ID NO:44. The sequence of panel B is SEQ ID NO:62.

FIG. 39 shows ExpaRNA exact pattern match and motif analysis result for 2D structures of (a) AS Uchl1 SINEB2 and (b) AS E4f1 SINEB2-Mm1t in miniSINEUP-GFP. The same as above applies.

Example 39

Figure 40:
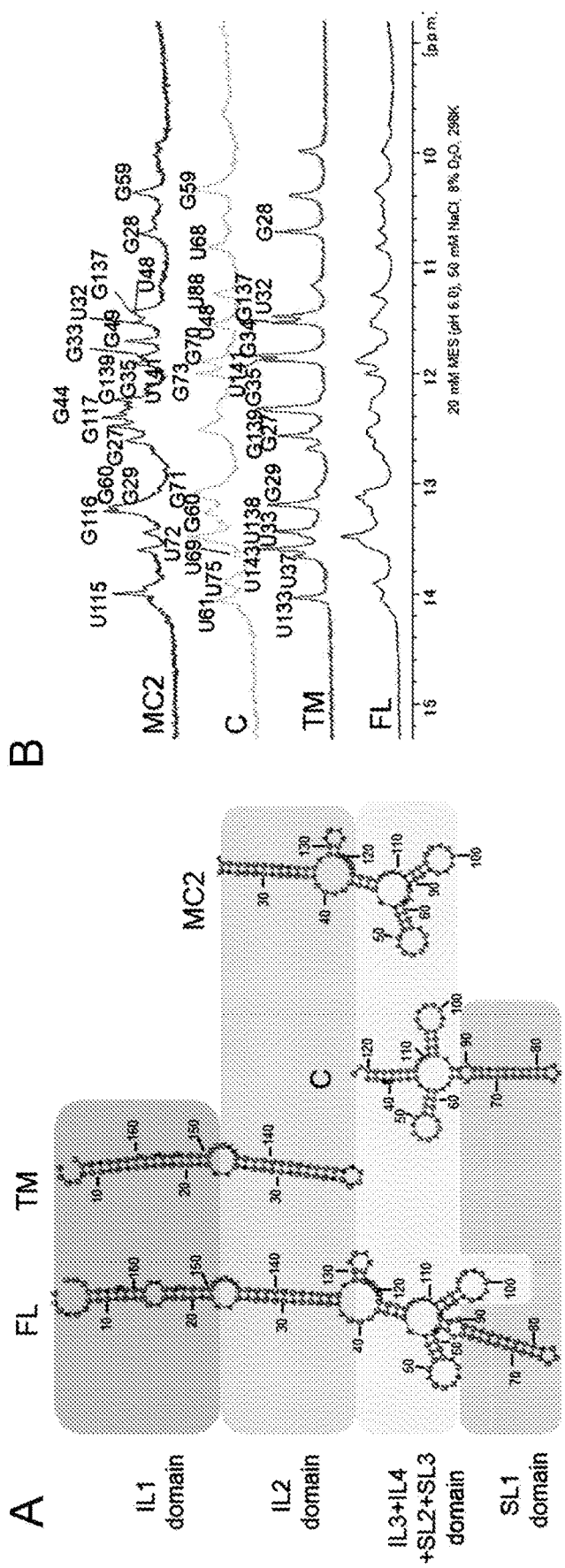
FIGS. 40 and 41 shows the structure dynamics of AS-Uchl1 SINEB2.
Figure 40:
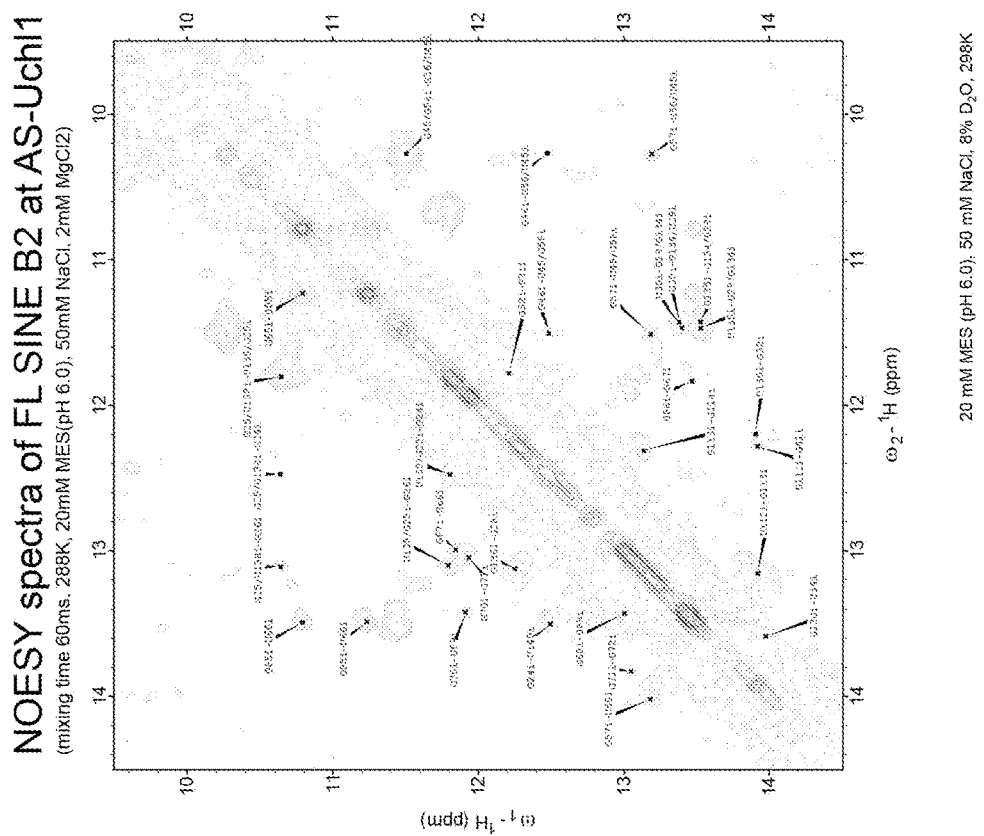

FIG. 40 shows the structure dynamics of AS-Uchl1 SINEB2. The purpose of dividing the SINEB2 RNA structure into smaller fragments is that the full-length (FL) is too big to analyze current NMR magnetic power. The structure needs to be divided to correctly assign imino proton signals of 1H NMR spectra. Divided RNAs should form similar structure to FL. 1H NMR spectra of TM and C and MC2 suggest that they do. In addition, these structures form differently in the NMR aqueous buffer with respect to chemical foot printing measurements (FIG. 2). The structure dynamics may happen in the physiological condition, such as the different cellular compartment (Sun et al., bioRxiv 2018., https://doi.org/10.1101/399386).

FIG. 40A shows the computational prediction structure of FL SINEB2 from AS-Uchl1 and parts of structure of it by RNA fold program. FL was divided into three structures (TM, C and MC2).

FIG. 40B shows the assignment of residues with NMR 1H spectra. Almost all signal peaks of MC2, C, TM structures were confirmed to the FL structure. These results suggest that MC2, C and TM form the same structure to the FL structure.

FIG. 40C shows five stem structures (dotted square marked stem at the left) were assigned at the Nuclear Overhauser effect spectroscopy (NOESY) (right).

Example 40

Figure 41:
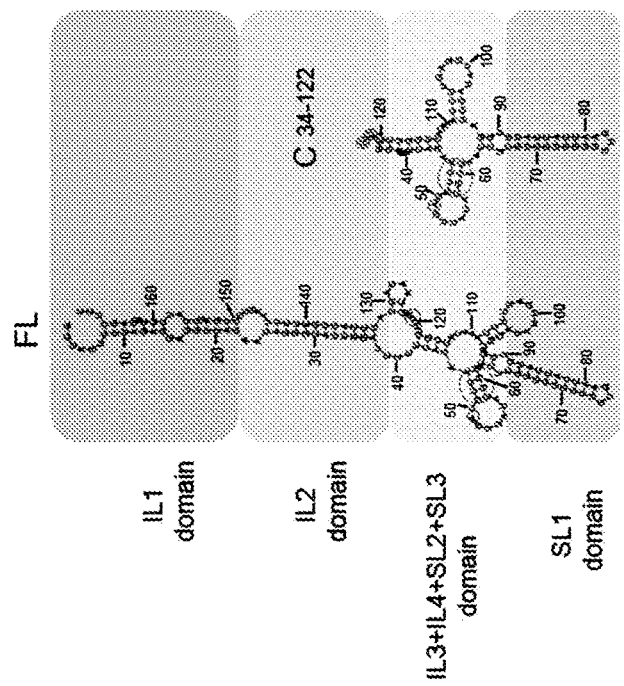
Figure 41:
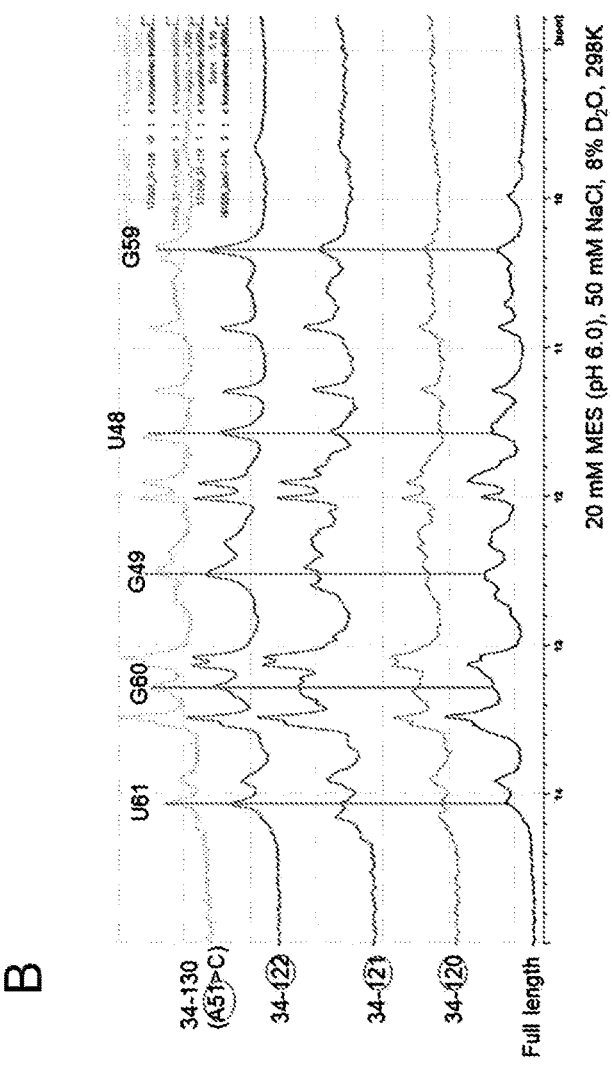

FIG. 41 shows the structure dynamics of AS-Uchl1 SINEB2.

Both computational predictions of FL and C form stem structure at 46-49 and 58-61 (dotted circle in (A)), which was not confirmed by chemical foot printing in FIGS. 1 and 2. In addition, the loop at 50-57 and single strand region at 18-123 were not confirmed by chemical foot printing in FIGS. 1 and 2. However, 1H NMR spectra and NOESY confirmed the stem structure at 46-49 and 58-61 (FIGS. 40B and 40C) as same to computational prediction structures. It was analyzed whether the stem structure of 46-49 and 58-61 is associated with any other unstructured residues at the loop 50-57 and at the single strand region at 18-123 by using A51>C mutant RNA and part of SINEB2 RNAs by 1H NMR spectra. In other words, it was investigated whether undetermined structure of chemical foot printing measurement simultaneously appeared and associated with each other in the NMR buffer condition.

Figure 12:
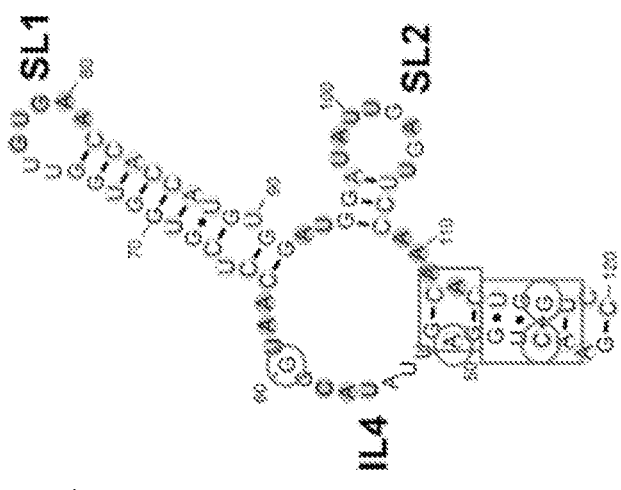
FIG. 12 related to Example 12 shows mutated sequences on the inverted SINE B2 and the effect of these mutations on inverted SINE B2 activity (Western blot and qRT-PCR). The sequence in panel A is SEQ ID NO:7.
Figure 12:
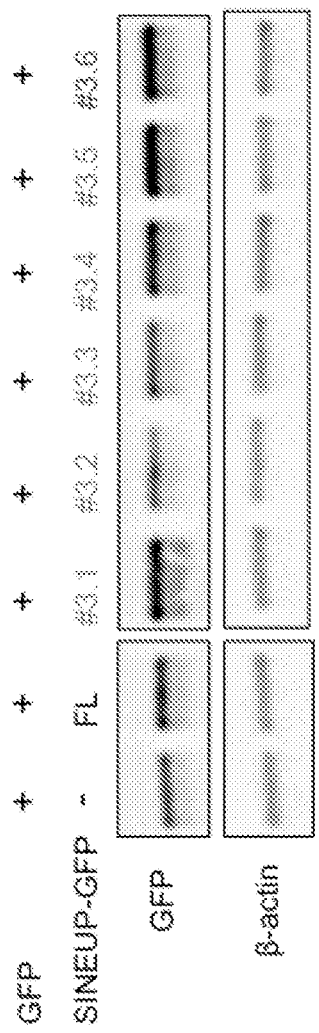
Figure 12:
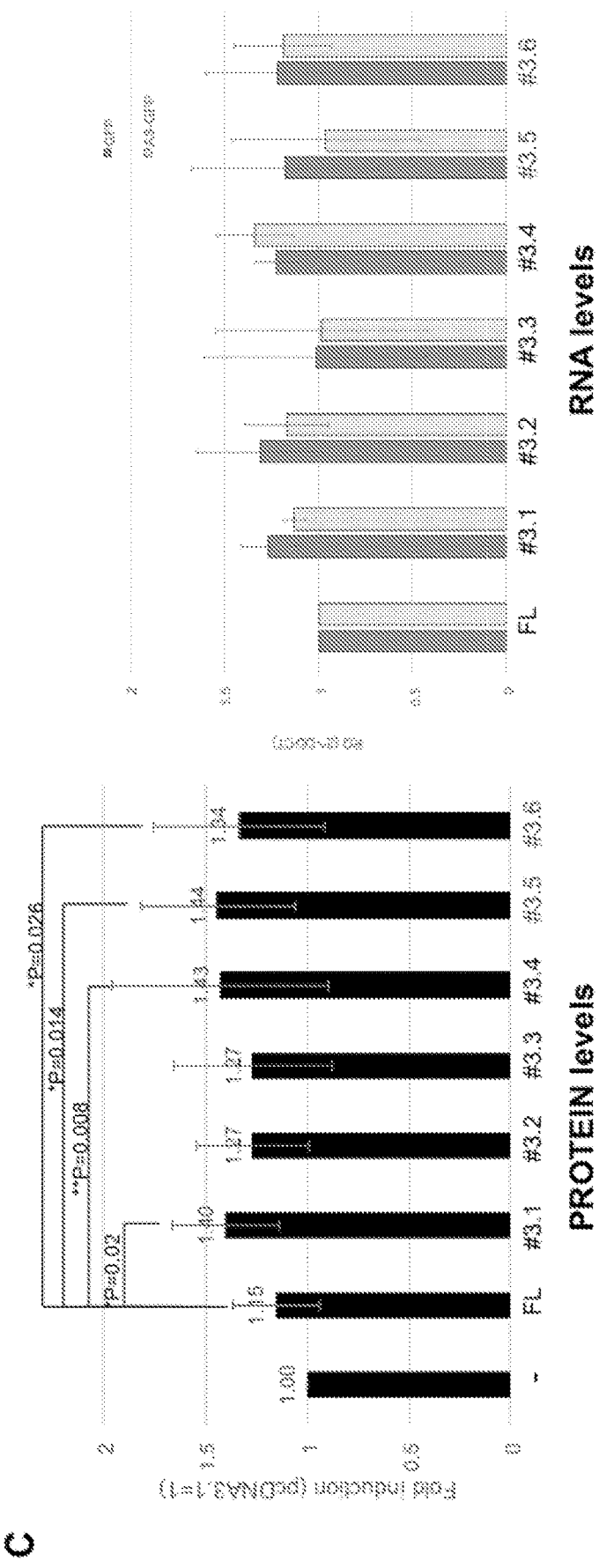

This example demonstrates a) computational prediction structures of FL and C domain (34-122) by RNAfold program. C structure was divided into unfolded region of FL structure (118-123). 5 residues (118-120) at C structure made stem with opposite residues.

b) 1H NMR spectra of three small RNAs (34-120, 34-121 and 34-122) and FL. 34-120 did not show stem of 45-49 and 58-61 (peak at vertical lines of U61, G60, G49, U48 and G59) but other three structures (FL, 34-121 and 34-122) showed these peaks. FIG. 41B shows that unfolded loop from 118-123 were important to form stem at 46-49 and 58-61. FIG. 41B shows 1H NMR spectra of A51C, which increased protein synthesis (FIG. 12). As a result of A51>C mutation, chemical shift happened at peaks of U48 and G59 (vertical lines). Additionally, two unassigned peaks at FL (vertical lines at the left of U61 and U48) disappeared. These peak shifts suggest that mutation at A51 changes the binding position of stems at 46-49 and increase the function of protein synthesis. Over all, loop structure at 50-57 and 118-123 interact with the structure formation of stem at 46-49 and 58-61 in the aqueous condition of NMR buffer (20 mM MES (pH6.0), 50 mM NaCl, 8% D2O, 298K). FIG. 41 suggests that SINEB2 structure is not strict but some structures are dynamic. Circles in A correspond to circles in B.

Example 41

Figure 42:
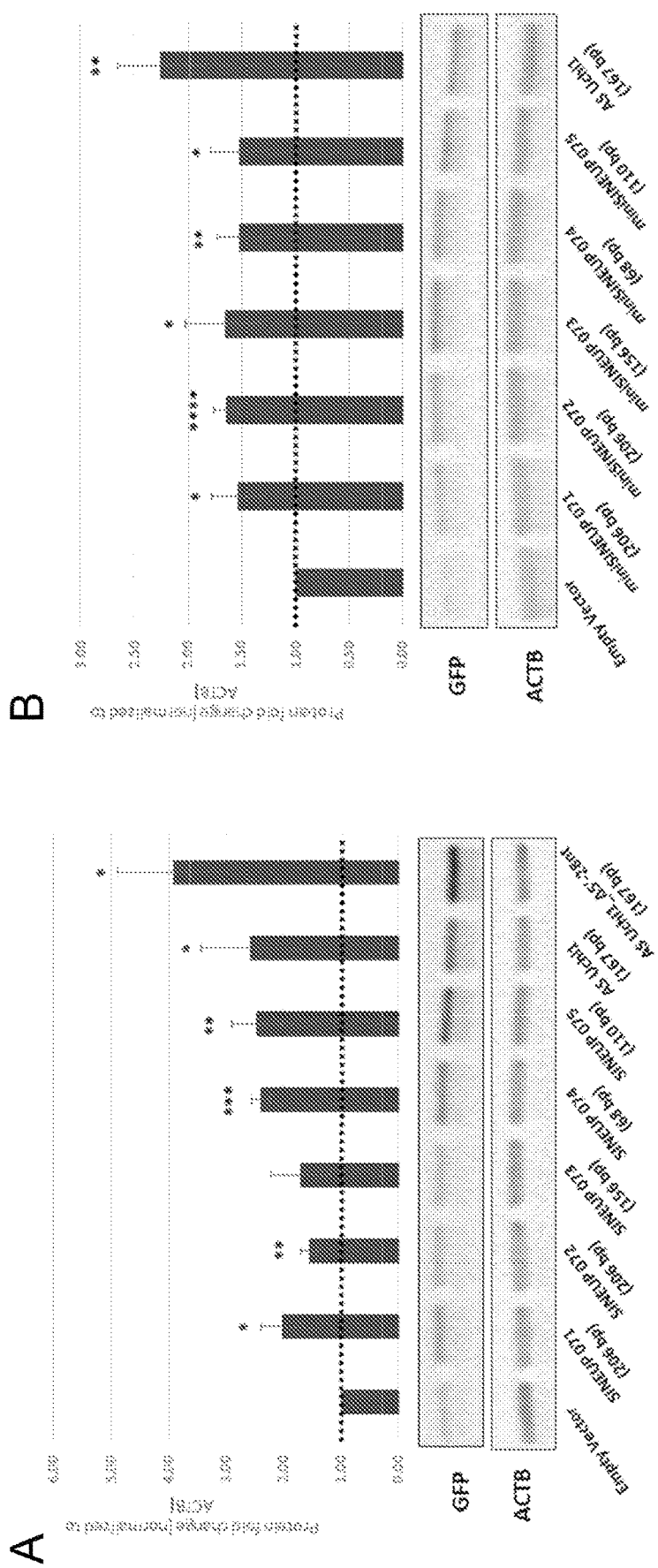
FIG. 42 shows how synthetic SINEUPs of various ED length and structure motif combinations up-regulate GFP protein expression.

FIG. 42 shows how synthetic SINEUPs of various ED length and structure motif combinations up-regulate GFP protein expression.

Average GFP protein fold change in HEK293T/17 cells after co-transfection with sense EGFP and (A) SINEUPs (n=3), and (B) miniSINEUPs (n=4) (24 h post-transfection). Western blot images and corresponding GFP band intensities (normalized to ACTB expression level) calculated using ImageJ software. Empty vector is used as negative control while AS Uchl1 (AS Uchl1 SINEB2 containing SINEUP or miniSINEUP) as positive control. SINEUP IDs are followed by the ED length in parentheses. error bars±SD; ** P<0.00005; * P<0.0005; ** P<0.005; * P<0.05; two-tailed Student's t-test.

Figure 23:
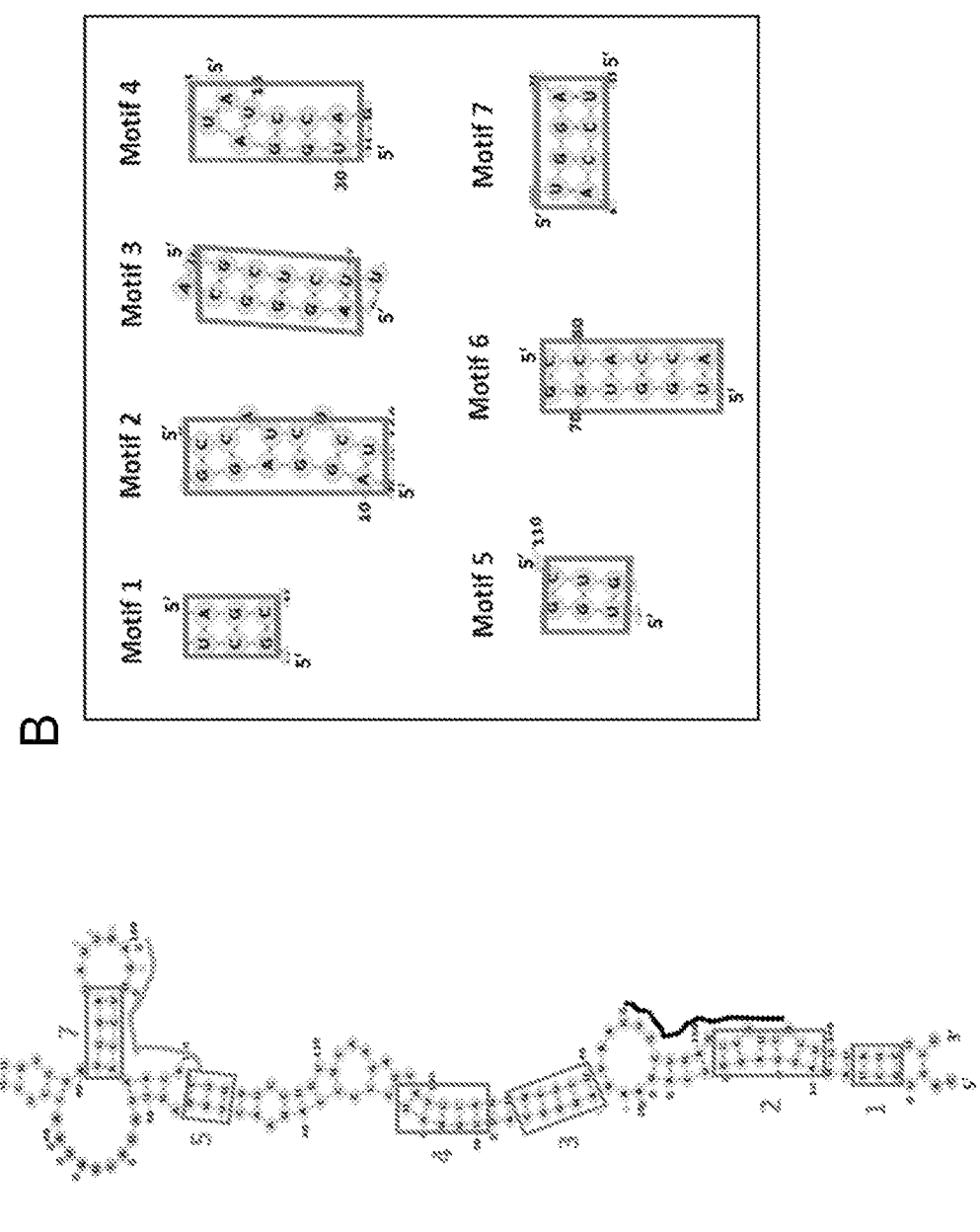
FIG. 23 shows the secondary (2D) structure of the miniSINEUP-GFP effector domain in HEK293T/17 cells and motifs therein. The sequence of panel A is SEQ ID NO:44.

Structure motif combinations (based on the motifs described in FIG. 23 tested in this experiment are provided below with complete features of the construct. For clarity reasons the SEQ ID NOs only indicate the sequence of the effector domain, which is the same in the SINEUP and in the corresponding miniSINEUP.

SINEUP 071/miniSINEUP 071 (206 nt): From 5' end partial motifs 1, partial motifs 2 and 3 (overlapping), complete motif 6, partial motifs 4 and 7

SINEUP 071
Recipient plasmid: pcDNA3.1(−)
Cloning restriction sites: XhoI-HindIII
Features: BD=−40/+32 (+21 nt spacer)
ED (SEQ ID NO:69)=Between SacII and ClaI restriction sites; 206 nt long sequence derived from consensus 2D structure based on global sequence and structure alignment of AS Uchl1, AS Uxt-b, and AS Txnip SINEB2 elements (+Alu and 3' tail region from AS Uchl1)
SINEUP length=1380 nt
miniSINEUP 071
Recipient plasmid: pcDNA3.1(−)
Cloning restriction sites: XhoI-HindIII
Features: BD=−40/+4 (+21 nt spacer)
ED=Between EcoRI and HindIII restriction sites; (SEQ ID NO:69)
SINEUP length=289 nt SINEUP 072/miniSINEUP 072 (206 nt): From 5' end partial motif 2, complete motif 1, partial motif 4, complete motif 7

SINEUP 072
Recipient plasmid: pcDNA3.1(−)
Cloning restriction sites: XhoI-HindIII
Features: BD=−40/+32 (+21 nt spacer)
ED (SEQ ID NO:70)=Between SacII and ClaI restriction sites; 206 nt long sequence derived from consensus 2D structure based on global sequence and structure alignment of AS Uchl1 and AS Uxt-b SINEB2 elements (+Alu and 3' tail region from AS Uchl1)
SINEUP length=1380 nt
miniSINEUP 072
Recipient plasmid: pcDNA3.1(−)
Cloning restriction sites: XhoI-HindIII
Features: BD=−40/+4 (+21 nt spacer)
ED=Between EcoRI and HindIII restriction sites; SEQ ID NO:70
SINEUP length=289 nt SINEUP 073/miniSINEUP 073 (156 nt): From 5' end complete motif 1, partial motifs 2 and 3 (overlapping), partial motif 4, complete motif 6, partial 7

SINEUP 073
Recipient plasmid: pcDNA3.1(−)
Cloning restriction sites: XhoI-HindIII
Features: BD=−40/+32 (+21 nt spacer)
ED (SEQ ID NO:71)=Between SacII and ClaI restriction sites; 156 nt long sequence derived from consensus 2D structure based on local sequence and structure alignment of AS Uchl1 and AS Uxt-b SINEB2 elements (+Alu and 3' tail region from AS Uchl1)
SINEUP length=1330 nt
miniSINEUP 073
Recipient plasmid: pcDNA3.1(−)
Cloning restriction sites: XhoI-HindIII
Features: BD=−40/+4 (+21 nt spacer)
ED=Between EcoRI and HindIII restriction sites; SEQ ID NO:71
SINEUP length=239 nt SINEUP 074/miniSINEUP 074 (68 nt): From 5' end partial 1, 7, 6 (overlapping), partial 2

SINEUP 074
Recipient plasmid: pcDNA3.1(−)
Cloning restriction sites: XhoI-HindIII
Features: BD=−40/+32 (+21 nt spacer)
ED (SEQ ID NO:72)=Between SacII and ClaI restriction sites; 68 nt long sequence derived from consensus 2D structure based on local sequence and structure alignment of AS Uchl1, AS Uxt-b, and AS Txnip SINEB2 elements (+Alu and 3' tail region from AS Uchl1)
SINEUP length=1242 nt
miniSINEUP 074
Recipient plasmid: pcDNA3.1(−)
Cloning restriction sites: XhoI-HindIII
Features: BD=−40/+4 (+21 nt spacer)
ED=Between EcoRI and HindIII restriction sites; SEQ ID NO:72
SINEUP length=151 nt SINEUP 075/miniSINEUP 075 (110 nt): From 5' end complete 1, 2, 3, and 6
Recipient plasmid: pcDNA3.1(−)
Cloning restriction sites: XhoI-HindIII Features: BD=−40/+32 (+21 nt spacer)

ED (SEQ ID NO:73)=Between SacII and ClaI restriction sites; 110 nt; Δ28-32, Δ42-60, Δ90-116, Δ131-135 AS Uchl1 SINEB2 deletion mutant (+Alu and 3' tail region from AS Uchl1)

SINEUP length=1284 nt miniSINEUP 075

Recipient plasmid: pcDNA3.1(−)

Cloning restriction sites: XhoI-HindIII

Features: BD=−40/+4 (+21 nt spacer)

ED=Between EcoRI and HindIII restriction sites; SEQ ID NO:73

SINEUP length=193 nt

AS Uchl1 and AS Uchl1_Δ5'-28 nt (167 nt): Positive control, all of the 7 motifs

All of the motif combinations tested in this experiment up-regulate GFP expression, though none could surpass the protein fold change induced by the positive control. This suggests that different motifs have combinatory effect on SINEUP activity. As explained in Example 22, most of the motifs have similar sequence composition that might compensate for any missing motif and ensure a minimal level of SINEUP activity. Optimum SINEUP effect is obtained by all of the 7 motifs in their respective order as evident from positive control (AS Uchl1 SINEB2). Interestingly, SINEUP 074 and miniSINEUP 074, despite the short ED and therefore lack of motifs, increases GFP protein expression and represents an example of minimal functional sequence required for SINEUP activity.

Example 42

Figure 43:
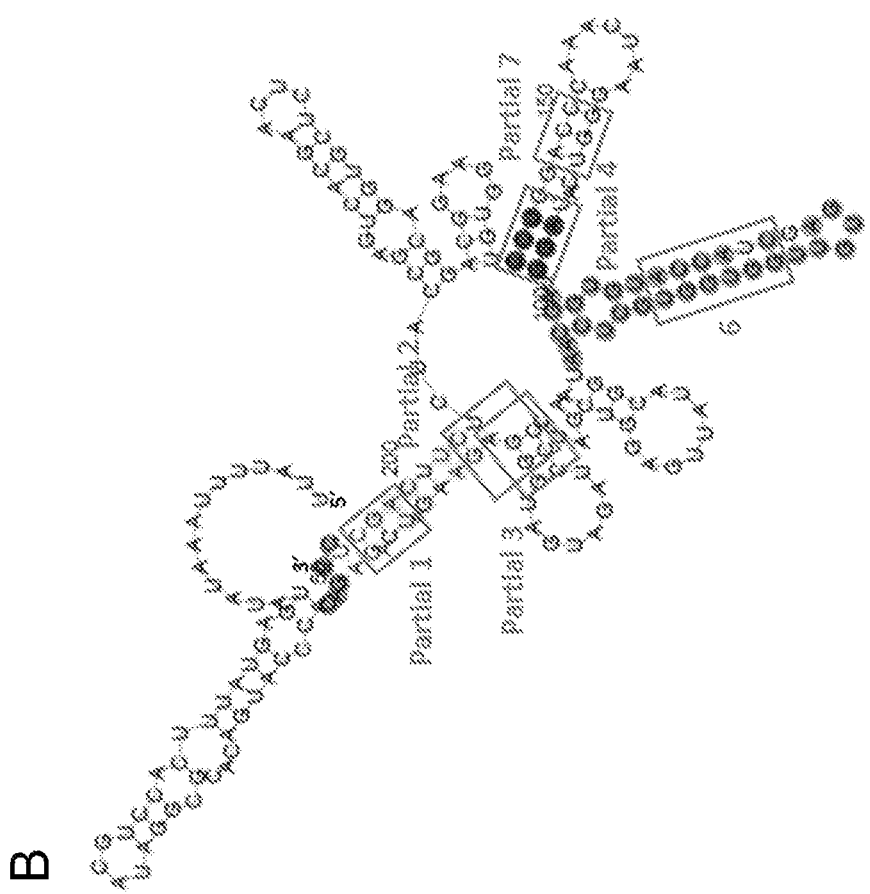
FIG. 43 shows ExpaRNA exact pattern match result for 2D structures of (A) AS Uchl1 SINEB2 in miniSINEUP-GFP (icSHAPE-guided) and (B) miniSINEUP 071 ED (RNAfold-predicted). The sequence of panel A is SEQ ID NO:44. The sequence of panel B is SEQ ID NO:69
Figure 43:
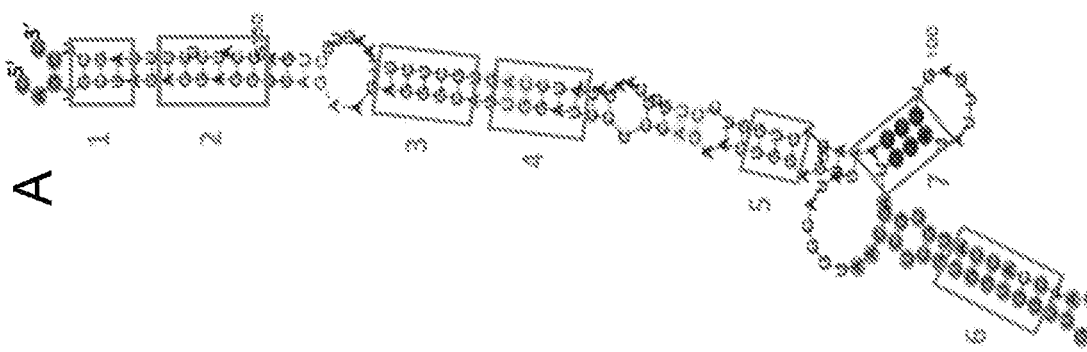

FIG. 43 shows ExpaRNA exact pattern match result for 2D structures of (A) AS Uchl1 SINEB2 in miniSINEUP-GFP (icSHAPE-guided) and (B) miniSINEUP 071 ED (RNAfold-predicted). Different shaded regions indicate corresponding unique patterns of exact sequence and structure match between two RNAs. The position of similar sequence and structure motifs shared among all of the SINEB2s are indicated with squares with their respective motif numbers. Due to their similar sequence composition, in some instances motifs 2 and 3 may overlap, and the same goes for motifs 4, 5, 6, and 7.

Example 43

Figure 44:
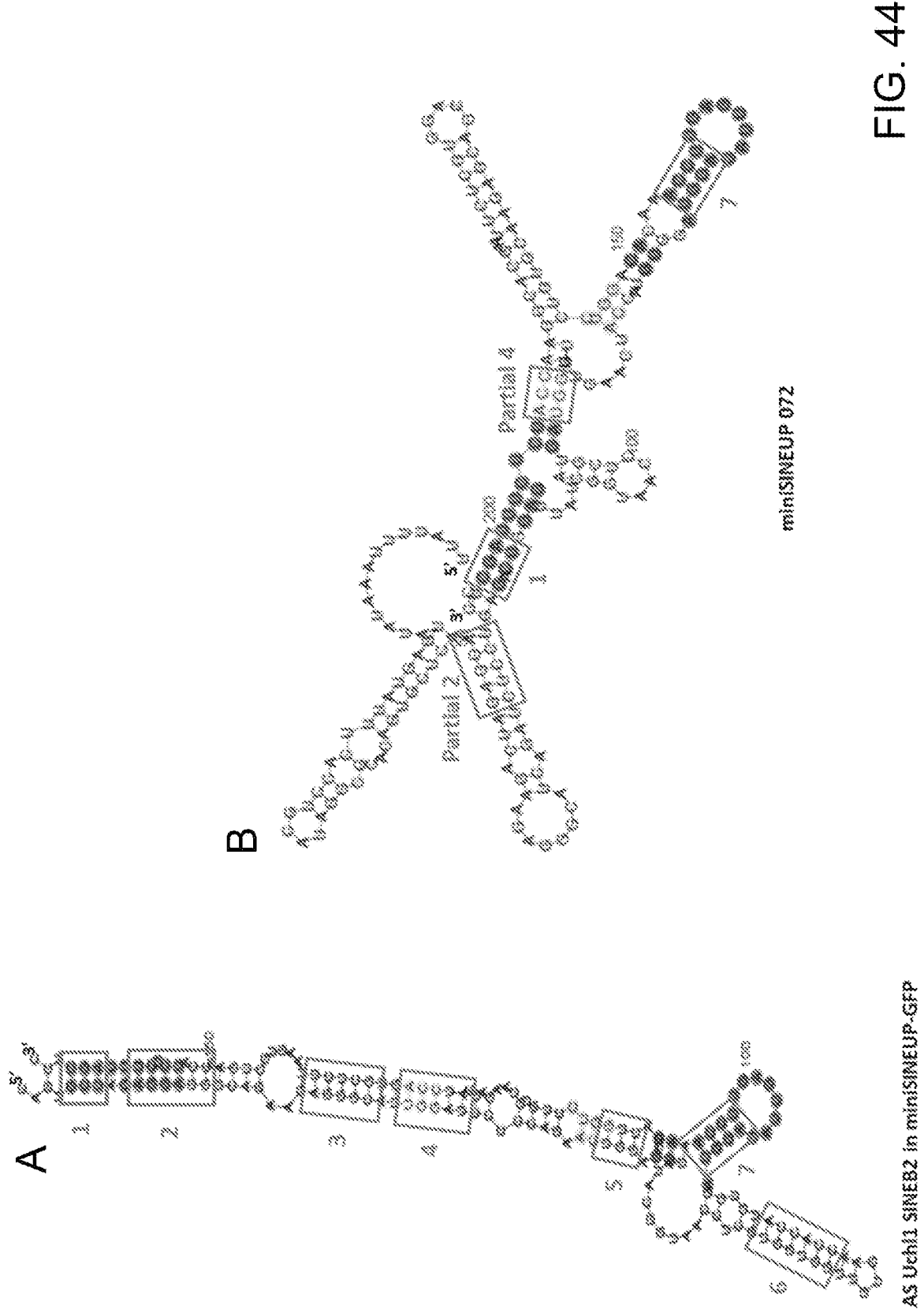
FIG. 44 shows ExpaRNA exact pattern match result for 2D structures of (A) AS Uchl1 SINEB2 in miniSINEUP-GFP (icSHAPE-guided) and (B) miniSINEUP 072 ED (RNAfold-predicted). The sequence of panel A is SEQ ID NO:44. The sequence of panel B is SEQ ID NO:70.

FIG. 44 shows ExpaRNA exact pattern match result for 2D structures of (A) AS Uchl1 SINEB2 in miniSINEUP-GFP (icSHAPE-guided) and (B) miniSINEUP 072 ED (RNAfold-predicted). The same as above applies.

Example 44

Figure 45:
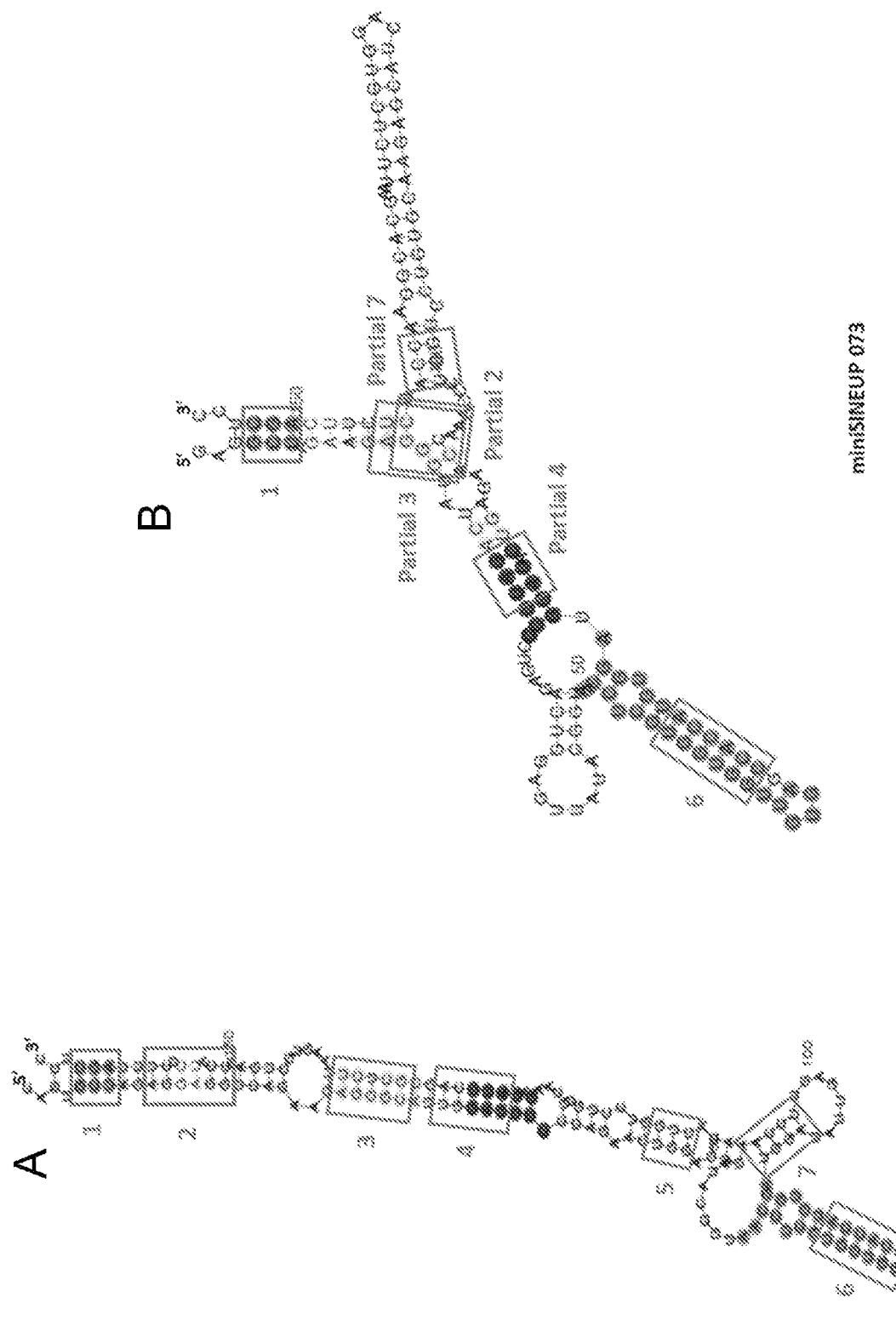
FIG. 45 shows ExpaRNA exact pattern match result for 2D structures of (A) AS Uchl1 SINEB2 in miniSINEUP-GFP (icSHAPE-guided) and (B) miniSINEUP 073 ED (RNAfold-predicted). The sequence of panel A is SEQ ID NO:44. The sequence of panel B is SEQ ID NO:71.

FIG. 45 shows ExpaRNA exact pattern match result for 2D structures of (A) AS Uchl1 SINEB2 in miniSINEUP-GFP (icSHAPE-guided) and (B) miniSINEUP 073 ED (RNAfold-predicted). The same as above applies.

Example 45

Figure 46:
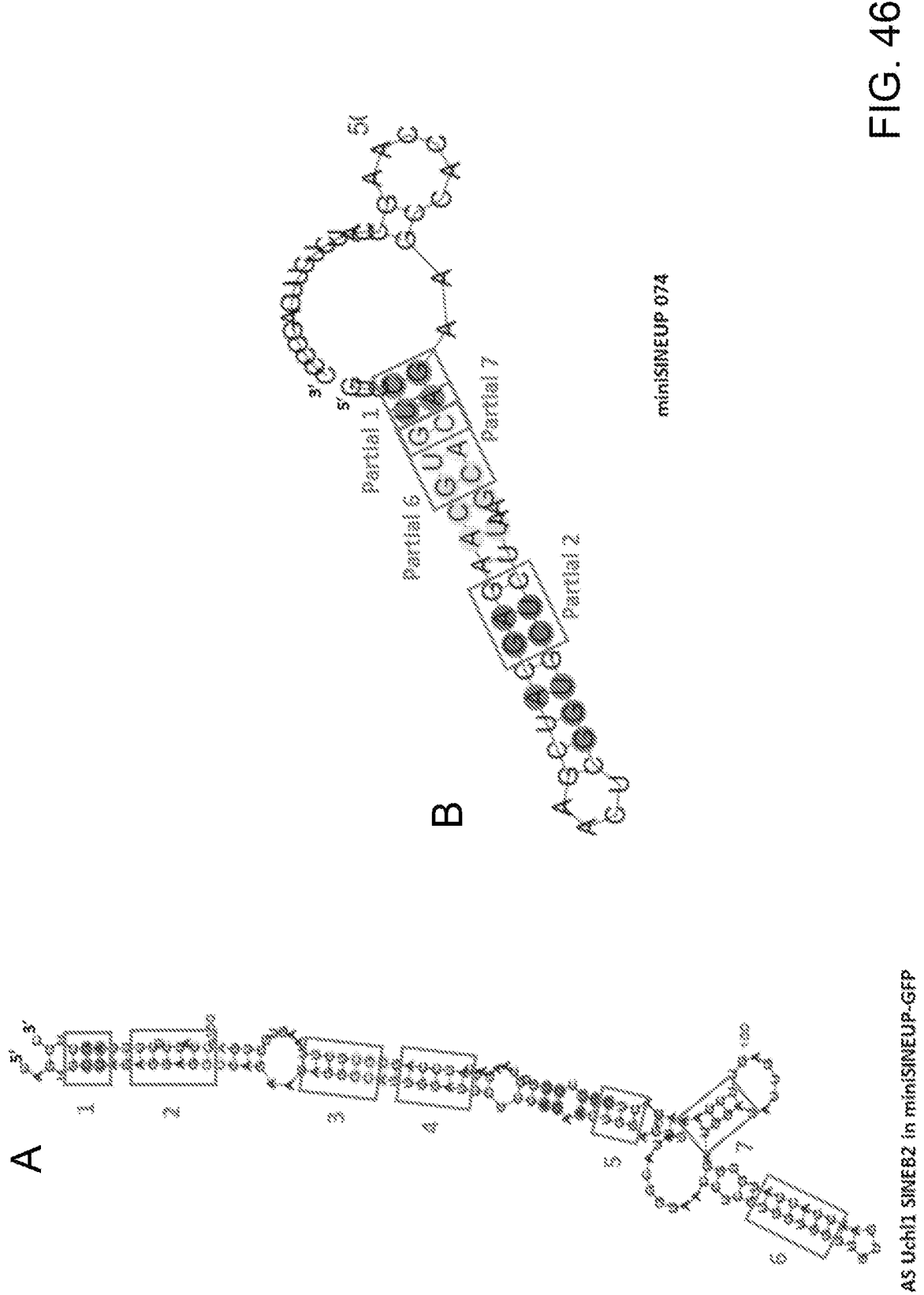
FIG. 46 shows ExpaRNA exact pattern match result for 2D structures of (a) AS Uchl1 SINEB2 in miniSINEUP-GFP (icSHAPE-guided) and (b) miniSINEUP 074 ED (RNAfold-predicted). The sequence of panel A is SEQ ID NO:44. The sequence of panel B is SEQ ID NO:72.

FIG. 46 shows ExpaRNA exact pattern match result for 2D structures of (a) AS Uchl1 SINEB2 in miniSINEUP-GFP (icSHAPE-guided) and (b) miniSINEUP 074 ED (RNAfold-predicted). The same as above applies.

Example 46

Figure 47:
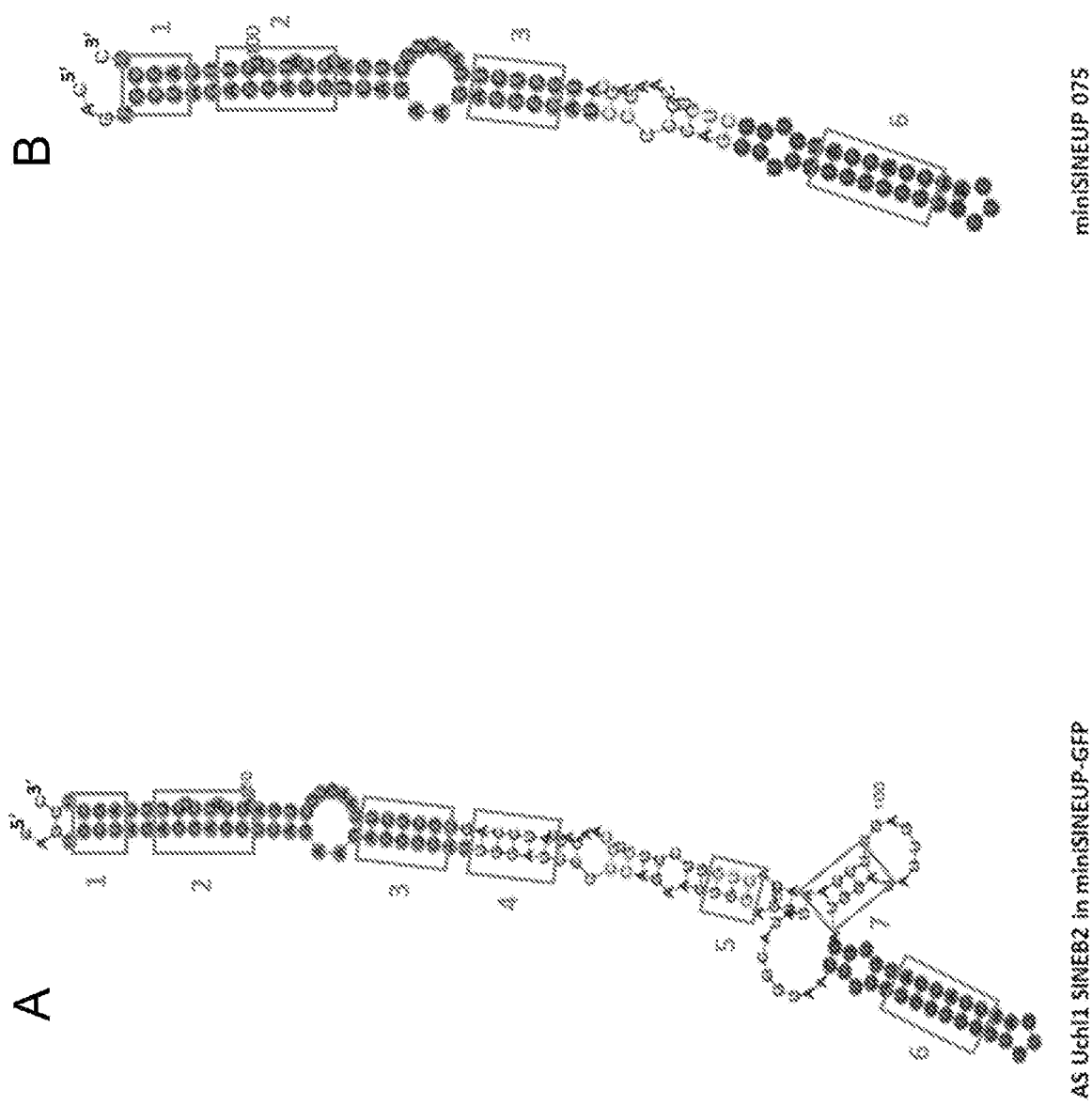
FIG. 47 shows ExpaRNA exact pattern match result for 2D structures of (a) AS Uchl1 SINEB2 in miniSINEUP-GFP (icSHAPE-guided) and (b) miniSINEUP 075 ED (RNAfold-predicted). The sequence of panel A is SEQ ID NO:44. The sequence of panel B is SEQ ID NO:75.

FIG. 47 shows ExpaRNA exact pattern match result for 2D structures of (a) AS Uchl1 SINEB2 in miniSINEUP-GFP (icSHAPE-guided) and (b) miniSINEUP 075 ED (RNAfold-predicted). The same as above applies.

Example 47

Figure 48:
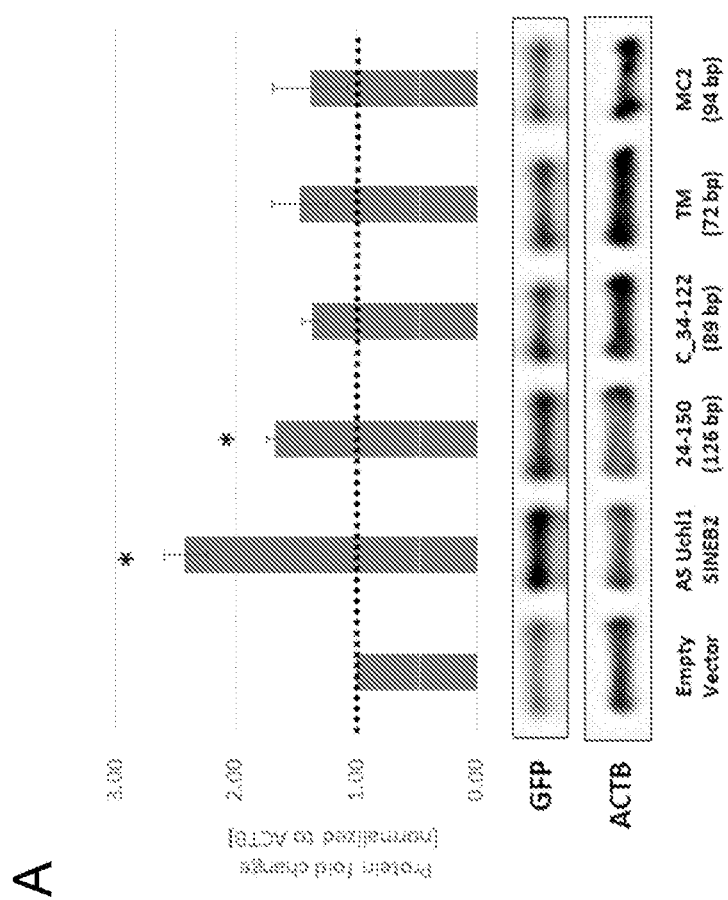
FIG. 48 shows how structure fragments of SINEB2 from AS Uchl1 up-regulate GFP protein expression. In panel B, the sequence "AS Uchl1 SINEB2" is SEQ ID NO:93, the sequence "22-150" is SEQ ID NO:95, the sequence "C_34-
Figure 48:
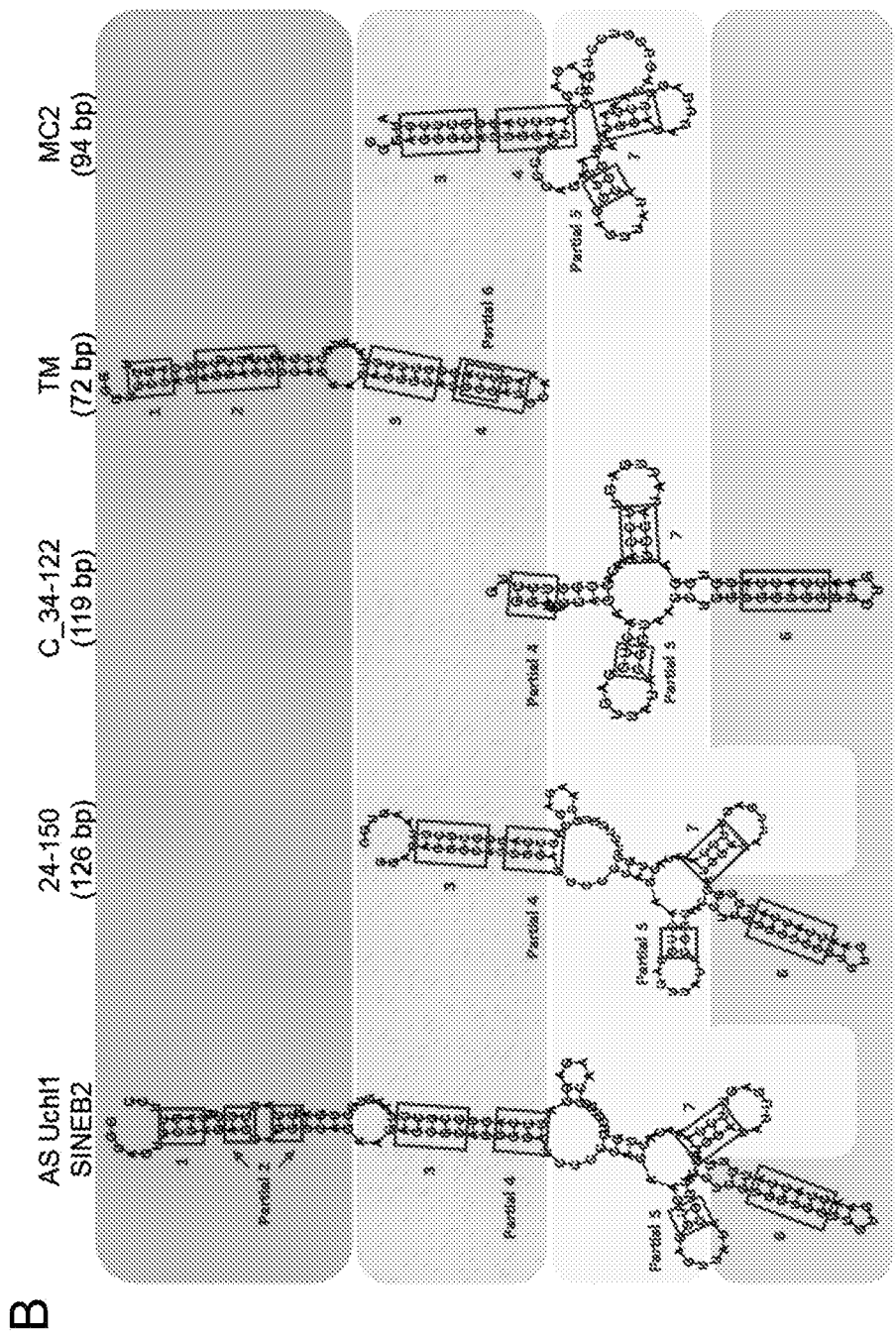

FIG. 48 shows how structure fragments of SINEB2 from AS Uchl1 up-regulate GFP protein expression.

(A) Average GFP protein fold change in HEK293T/17 cells after co-transfection with sense EGFP and SINEUPs (n=2) (24 h post-transfection). Western blot images and corresponding GFP band intensities (normalized to ACTB expression level) calculated using ImageJ software. Empty vector is used as negative control.

All of the structure fragments in this experiment up-regulated GFP expression, though none could surpass the protein fold change induced by the AS Uchl1 SINEB2. These fragments form the same structure as the AS Uchl1 SINEB2 structure (FIG. 23).

This suggests that structure with different motifs have combinatory effect on SINEUP activity. As explained in FIG. 23, most of the motifs have similar sequence composition that might compensate for any missing motif and ensure a minimal level of SINEUP activity. Optimal SINEUP effect is obtained by all of the 7 motifs in their respective order as evident from positive control (AS Uchl1 SINEB2).

(B) This AS Uchl1 SINEB2 structure is confirmed in the NMR spectroscopy solution as alternative structures. Other fragments keep forming as shorter structure of AS Uchl1 SINEB2. Motif combinations correspond to new FIG. 23.

Structure motif combinations (based on the motifs described in FIG. 23) are provided below with complete features of the construct. For clarity reasons the SEQ ID Nos only indicate the sequence of the effector domain.

AS Uchl1 SINEB2: From 5' end complete motifs 1, partial motifs 2, complete motif 3, partial motif 5, complete motif 6 and complete motifs 7

24-150 (126 nt): From 5' end complete motif 3, partial motif 4, partial motif 5, complete motif 6 and complete motif 7

Recipient plasmid: pcDNA3.1(−)

Cloning restriction sites: XhoI-HindIII

Features: BD=−40/+32 (+21 nt spacer)

ED (SEQ ID NO:74)=Between SacII and ClaI restriction sites; 126 nt long sequence derived from AS Uchl1 SINEB2 elements (+Alu and 3' tail region from AS Uchl1)

SINEUP length=1300 nt

C_34-122 (89 nt): From 5' end partial motif 4, 5 and complete motif 6 and complete motif 7

Recipient plasmid: pcDNA3.1(−)

Cloning restriction sites: XhoI-HindIII

Features: BD=−40/+32 (+21 nt spacer)

ED (SEQ ID NO:75)=Between SacII and ClaI restriction sites; 89 nt long sequence contains in AS Uchl1 SINEB2 elements (+Alu and 3' tail region from AS Uchl1)

SINEUP length=1263 nt

TM (72 nt): From 5' end complete motif 1, complete motif 2, complete motif 3, complete motif 4 and partial motifs 6 (overlapping)

Recipient plasmid: pcDNA3.1(−)

Cloning restriction sites: XhoI-HindIII

Features: BD=−40/+32 (+21 nt spacer)

ED (SEQ ID NO:76)=Between SacII and ClaI restriction sites; 72 nt long sequence contains in AS Uchl1 SINEB2 elements (+Alu and 3' tail region from AS Uchl1)
SINEUP length=1246 nt
MC2 (94 nt): From 5' end complete motif 3, complete motif 4, partial motif 5 and complete motif 7. Recipient plasmid: pcDNA3.1(−)
Cloning restriction sites: XhoI-HindIII
Features: BD=−40/+32 (+21 nt spacer)
ED (SEQ ID NO:77)=Between SacII and ClaI restriction sites; 94 nt long sequence derived from AS Uchl1 SINEB2 elements (+Alu and 3' tail region from AS Uchl1)
SINEUP length=1268 nt Example 48

FIG. 49 shows that SINEUPs are active when expressed as circular RNA. Circular SINEUP-DJ-1 (circSINEUP-DJ-1) is able to increase endogenous DJ-1 protein levels in a Binding Domain-dependent manner with no change in target DJ-1 mRNA level in HEK 293T/17 cells.

This example demonstrates that SINEUP sequences can be circular RNA and that these possess translation up-regulation activity in functional nucleic acid molecules with endogenous mRNA. Activity is obtained with the same primary nucleotide sequence but with the 5'end and the 3' end of the linear SINEUP-DJ-1 covalently ligated. FIG. 49A is a schematic representation of the circular SINEUP-DJ-1 RNA (circSINEUP-DJ-1) that contain both the canonical sequence inverted SINE B2 and the Binding Domain for DJ-1 mRNA. FIG. 49B shows translation up-regulation activity of functional nucleic acid molecules targeting endogenously expressed DJ-1 mRNA in which the SINEUP is in the circular form. HEK 293T/17 cells were transfected with an empty vector, or a circular SINEUP-DJ-1 and a circular SINEUP-DJ-deltaBD lacking the antisense sequence to DJ-1 mRNA. Western blot was performed with anti-DJ-1 antibody to monitor overexpressed protein. β-actin was used as loading control. Fold-induction was calculated on Western blot images normalized to β-actin and relative to empty control samples. FIG. 49C presents real time qPCR analysis to quantify circular SINEUP-DJ-1 RNA and DJ-1 mRNA levels proving the mechanism is post-transcriptional.

Advantages

The identification of SINE B2 structural elements allows a structure-directed strategy for the selection and design of SINEUP variants with increased activity and potential utility in humans. In particular, shorter SINEUP variants are advantageous for a number of reasons, among which in vivo delivery and stability.

```
                       SEQUENCE LISTING

<160> NUMBER OF SEQ ID NOS: 96

<210> SEQ ID NO 1
<211> LENGTH: 29
<212> TYPE: RNA
<213> ORGANISM: Mus musculus

<400> SEQUENCE: 1
ccucguggug guugugaacc accaugugg                                         29

<210> SEQ ID NO 2
<211> LENGTH: 61
<212> TYPE: RNA
<213> ORGANISM: Mus musculus

<400> SEQUENCE: 2
guuauacggu aaccucgugg ugguugugaa ccaccaugug gauggauauu gaguuccaaa       60
c                                                                      61

<210> SEQ ID NO 3
<211> LENGTH: 98
<212> TYPE: RNA
<213> ORGANISM: Mus musculus

<400> SEQUENCE: 3 auccccaga acuggaguua uacgguaacc ucgugguggu ugugaaccac caugggaug         60 gauauugagu uccaaacacu gguccugugc aagagcau                              98

<210> SEQ ID NO 4
<211> LENGTH: 129
<212> TYPE: RNA
<213> ORGANISM: Mus musculus

<400> SEQUENCE: 4
gaagagggca uuggauccccc cagaacugga guuauacggu aaccucgugg ugguugugaa     60
```
ccaccaugug gauggauauu gaguuccaaa cacugguccu gugcaagagc auccagugcu    120
cuuaagugc                                                            129

<210> SEQ ID NO 5
<211> LENGTH: 183
<212> TYPE: RNA
<213> ORGANISM: Mus musculus

<400> SEQUENCE: 5
gggcagugcu agaggagguc agaagagggc auuggauccc ccagaacugg aguuauacgg    60
uaaccucgug gugguuguga accaccaugu ggauggauau ugaguccaa acacuggucc     120 ugugcaagag cauccagugc ucuuaagugc ugagccaucu cuuuagcucc agucucuuaa    180
gcu                                                                  183

<210> SEQ ID NO 6
<211> LENGTH: 67
<212> TYPE: RNA
<213> ORGANISM: Mus musculus

<400> SEQUENCE: 6
gaacuggagu uauacgguaa ccucguggug guugugaacc accaugugga uggauauuga    60
guuccaa                                                              67

<210> SEQ ID NO 7
<211> LENGTH: 77
<212> TYPE: RNA
<213> ORGANISM: Mus musculus

<400> SEQUENCE: 7
gaacuggagu uauacgguaa ccucguggug guugugaacc accaugugga uggauauuga    60
guuccaaaca cuggucc                                                   77

<210> SEQ ID NO 8
<211> LENGTH: 107
<212> TYPE: RNA
<213> ORGANISM: Mus musculus

<400> SEQUENCE: 8 ggaucccca gaacuggagu uauacgguaa ccucguggug guugugaacc accaugugga    60
uggauauuga guuccaaaca cugguccugu gcaagagcau ccagugc                  107

<210> SEQ ID NO 9
<211> LENGTH: 127
<212> TYPE: RNA
<213> ORGANISM: Mus musculus

<400> SEQUENCE: 9
agagggcauu ggaucccca gaacuggagu uauacgguaa ccucguggug guugugaacc    60
accaugugga uggauauuga guuccaaaca cugguccugu gcaagagcau ccagugcucu    120
uaagugc                                                              127

<210> SEQ ID NO 10
<211> LENGTH: 170
<212> TYPE: RNA
<213> ORGANISM: Artificial Sequence
<220> FEATURE:
<223> OTHER INFORMATION: nt 1-67 and 78-183 of inverted SINE B2
      transposable element derived from AS Uchl1

<400> SEQUENCE: 10
cagugcuaga ggaggucaga agagggcauu ggauccccca gaacuggagu uauacgguaa    60
ccucugaacc accaugugga uggauauuga guuccaaaca cugguccugu gcaagagcau   120
ccagugcucu uaagugcuga gccaucucuu uagcuccagu cucuuaagcu              170

<210> SEQ ID NO 11
<211> LENGTH: 180
<212> TYPE: RNA
<213> ORGANISM: Artificial Sequence
<220> FEATURE:
<223> OTHER INFORMATION: stemDM mutant - G70A and G73A mutant of
      inverted SINE B2 transposable element derived from AS Uchl1

<400> SEQUENCE: 11
cagugcuaga ggaggucaga agagggcauu ggauccccca gaacuggagu uauacgguaa    60
ccucguagua guugugaacc accaugugga uggauauuga guuccaaaca cugguccugu   120
gcaagagcau ccagugcucu uaagugcuga gccaucucuu uagcuccagu cucuuaagcu   180

<210> SEQ ID NO 12
<211> LENGTH: 38
<212> TYPE: RNA
<213> ORGANISM: Mus musculus

<400> SEQUENCE: 12
gguaaccucg uggugguugu gaaccaccau guggaugg                            38

<210> SEQ ID NO 13
<211> LENGTH: 167
<212> TYPE: RNA
<213> ORGANISM: Artificial Sequence
<220> FEATURE:
<223> OTHER INFORMATION: nt 1-34 and 48-183 of inverted SINE B2
      transposable element derived from AS Uchl1

<400> SEQUENCE: 13
cagugcuaga ggaggucaga agagggcauu guggaguuau acguaaccu cguggugguu    60 gugaaccacc auguggaugg auauugaguu ccaaacacug guccugugca agagcaucca   120
gugcucuuaa gugcugagcc aucucuuuag cuccagucuc uuaagcu                 167

<210> SEQ ID NO 14
<211> LENGTH: 165
<212> TYPE: RNA
<213> ORGANISM: Artificial Sequence
<220> FEATURE:
<223> OTHER INFORMATION: nt 1-146 and 162-183 of inverted SINE B2
      transposable element derived from AS Uchl1

<400> SEQUENCE: 14
cagugcuaga ggaggucaga agagggcauu ggauccccca gaacuggagu uauacgguaa    60
ccucguggug guugugaacc accaugugga uggauauuga guuccaaaca cugguccugu   120
gcaagagcau ccagugcucu uaauuuagcu ccagucucuu aagcu                   165

<210> SEQ ID NO 15
<211> LENGTH: 180
<212> TYPE: RNA
<213> ORGANISM: Artificial Sequence
<220> FEATURE:
<223> OTHER INFORMATION: G60A mutant of inverted SINE B2 transposable
      element derived from AS Uchl1

<400> SEQUENCE: 15
cagugcuaga ggaggucaga agagggcauu ggauccccca gaacuggagu uauacgauaa        60
ccucguggug guugugaacc accaugugga uggauauuga guuccaaaca cguggccugu       120
gcaagagcau ccagugcucu uaagugcuga gccaucucuu uagcuccagu cucuuaagcu       180

<210> SEQ ID NO 16
<211> LENGTH: 180
<212> TYPE: RNA
<213> ORGANISM: Artificial Sequence
<220> FEATURE:
<223> OTHER INFORMATION: G60C mutant of inverted SINE B2 transposable
      element derived from AS Uchl1

<400> SEQUENCE: 16
cagugcuaga ggaggucaga agagggcauu ggauccccca gaacuggagu uauacgcuaa        60
ccucguggug guugugaacc accaugugga uggauauuga guuccaaaca cguggccugu       120
gcaagagcau ccagugcucu uaagugcuga gccaucucuu uagcuccagu cucuuaagcu       180

<210> SEQ ID NO 17
<211> LENGTH: 180
<212> TYPE: RNA
<213> ORGANISM: Artificial Sequence
<220> FEATURE:
<223> OTHER INFORMATION: A51C mutant of inverted SINE B2 transposable
      element derived from AS Uchl1

<400> SEQUENCE: 17
cagugcuaga ggaggucaga agagggcauu ggauccccca gaacuggcgu uauacgguaa        60
ccucguggug guugugaacc accaugugga uggauauuga guuccaaaca cguggccugu       120
gcaagagcau ccagugcucu uaagugcuga gccaucucuu uagcuccagu cucuuaagcu       180

<210> SEQ ID NO 18
<211> LENGTH: 180
<212> TYPE: RNA
<213> ORGANISM: Artificial Sequence
<220> FEATURE:
<223> OTHER INFORMATION: C47G and G117C mutant of inverted SINE B2
      transposable element derived from AS Uchl1

<400> SEQUENCE: 18
cagugcuaga ggaggucaga agagggcauu ggauccccca gaaguggagu uauacgguaa        60
ccucguggug guugugaacc accaugugga uggauauuga guuccaaaca cugcuccugu       120
gcaagagcau ccagugcucu uaagugcuga gccaucucuu uagcuccagu cucuuaagcu       180

<210> SEQ ID NO 19
<211> LENGTH: 180
<212> TYPE: RNA
<213> ORGANISM: Artificial Sequence
<220> FEATURE:
<223> OTHER INFORMATION: 46-49/115-118 stem swap mutant of inverted SINE
      B2 transposable element derived from AS Uchl1

<400> SEQUENCE: 19
cagugcuaga ggaggucaga agagggcauu ggauccccca gauggugagu uauacgguaa        60
ccucguggug guugugaacc accaugugga uggauauuga guuccaaaca cgucaccugu       120
gcaagagcau ccagugcucu uaagugcuga gccaucucuu uagcuccagu cucuuaagcu       180

<210> SEQ ID NO 20
<211> LENGTH: 180
<212> TYPE: RNA

```
<213> ORGANISM: Artificial Sequence
<220> FEATURE:
<223> OTHER INFORMATION: 50-53 and 112-114 base swap mutant of inverted
      SINE B2 transposable element derived from AS Uchl1

<400> SEQUENCE: 20
cagugcuaga ggaggucaga agagggcauu ggaucccca gaacugcacu auacgguaac      60
cucgguggug uugugaacca ccauguggau ggauauugag uuccaaauga gugguccugu    120
gcaagagcau ccagugcucu uaagugcuga gccaucucuu uagcuccagu cucuuaagcu    180

<210> SEQ ID NO 21
<211> LENGTH: 116
<212> TYPE: RNA
<213> ORGANISM: Artificial Sequence
<220> FEATURE:
<223> OTHER INFORMATION: nt 27-142 of inverted SINE B2 transposable
      element derived from AS Uchl1

<400> SEQUENCE: 21
gggcauugga uccccagaa cuggaguuau acguaaccu cguggugguu gugaaccacc       60
auguggaugg auauugaguu ccaaacacug guccugugca agagcaucca gugcuc        116

<210> SEQ ID NO 22
<211> LENGTH: 77
<212> TYPE: RNA
<213> ORGANISM: Artificial Sequence
<220> FEATURE:
<223> OTHER INFORMATION: nt 44-120 A45G mutant of inverted SINE B2
      transposable element derived from AS Uchl1

<400> SEQUENCE: 22
ggacuggagu uauacgguaa ccucguggug guugugaacc accaugugga uggauauuga     60
guuccaaaca cuggucc                                                   77

<210> SEQ ID NO 23
<211> LENGTH: 77
<212> TYPE: RNA
<213> ORGANISM: Artificial Sequence
<220> FEATURE:
<223> OTHER INFORMATION: nt 44-120 A51C mutant of inverted sine B2
      transposable element derived from AS Uchl1

<400> SEQUENCE: 23
gaacuggcgu uauacgguaa ccucguggug guugugaacc accaugugga uggauauuga     60
guuccaaaca cuggucc                                                   77

<210> SEQ ID NO 24
<211> LENGTH: 75
<212> TYPE: RNA
<213> ORGANISM: Artificial Sequence
<220> FEATURE:
<223> OTHER INFORMATION: Rodentia - SINE ID (BC1)

<400> SEQUENCE: 24
ggggguuggg auuuagcuca gugguagagc gcuugccuag caagcgcaag gcccuggguu     60
cgguccucag cuccg                                                     75

<210> SEQ ID NO 25
<211> LENGTH: 95
<212> TYPE: RNA
<213> ORGANISM: Brassica

<400> SEQUENCE: 25
```

```
gccgggacag aauagccuag ugguaacacu agagugaacu ggaucccaag gcaccugggu    60
ucgaguccuc ugggauuccg gagaccgccc gugac                              95

<210> SEQ ID NO 26
<211> LENGTH: 115
<212> TYPE: RNA
<213> ORGANISM: Oryza

<400> SEQUENCE: 26
gagaaacgcc cugggucuuu ccggcuagcu ccacaaggug gugggcuagc cgaccugggu    60
ucgaagccuc accccuucua auuauuugau auuaggccuu cccuaauau ucgug         115

<210> SEQ ID NO 27
<211> LENGTH: 140
<212> TYPE: RNA
<213> ORGANISM: Artificial Sequence
<220> FEATURE:
<223> OTHER INFORMATION: Salmonidae - SmaI

<400> SEQUENCE: 27
gguccuucug uagcucaguu gguagagcau ggcgcuugua acgccagggu aguggguucg    60
auucccggga ccaccccauac guaaaaaugu augcacacau gacuguaagu cgcuuuggau  120
aaaagcgucu gcuaaauggc                                              140

<210> SEQ ID NO 28
<211> LENGTH: 159
<212> TYPE: RNA
<213> ORGANISM: Arabidopsis

<400> SEQUENCE: 28
accaacgugc uguuggccca gugguaaauc ucccaggugg aggugcuggg uucgaggcac    60
guugggaggg aucucuucuc caaaagagau gaauuuaacc uggugugggu cccgccucua   120
ggagauguag ggccuuuggg cuugaacuuc cagauauuc                         159

<210> SEQ ID NO 29
<211> LENGTH: 171
<212> TYPE: RNA
<213> ORGANISM: Brassica

<400> SEQUENCE: 29
acccaggacc ucguagucca guggcuacuac ccucucuuug gggaggggag gucggcuguu    60
cgacucgcgg ggaggggggag gcgugcccag ggcccuaacc gguacaggca caggcuggcg  120
ccgggccuag guggugggcu ggucgaaggc uggucaacac cugguuaauc a            171

<210> SEQ ID NO 30
<211> LENGTH: 185
<212> TYPE: RNA
<213> ORGANISM: Artificial Sequence
<220> FEATURE:
<223> OTHER INFORMATION: Rodentia - B2

<400> SEQUENCE: 30
gggcuggaga gauggcucag ugguuaagag caccugacug cucuuccaga gguccugagu    60
ucaauuccca gcaaccacau ggugggcuca c aaccaucugu aaugagaucu gaugcccucu  120
ucuggugugu cugaagacag cuacaguqua cuuacauaua auaaauaaau aaauaaauaa   180
aucuu                                                              185
```

<210> SEQ ID NO 31
<211> LENGTH: 189
<212> TYPE: RNA
<213> ORGANISM: Artificial Sequence
<220> FEATURE:
<223> OTHER INFORMATION: Salmonidae - HpaI

<400> SEQUENCE: 31

| | | | | | | |
|---|---|---|---|---|---|---|
| ggggcggcag | gguagccuag | ugguuagagc | guuggacuag | uaaccgaaag | guugcaaguu | 60 |
| caaaucccccg | agcugacaag | guacaaaucu | gucguucugc | cccugaacaa | ggcaguuaac | 120 |
| ccacuguucc | uaggccguca | uugaaaauaa | gaauuuguuc | uuaacugacu | ugccuaguua | 180 |
| aauaaaggu | | | | | | 189 |

<210> SEQ ID NO 32
<211> LENGTH: 235
<212> TYPE: RNA
<213> ORGANISM: Equus

<400> SEQUENCE: 32

| | | | | | | |
|---|---|---|---|---|---|---|
| ggggccagcc | ccguggccua | gugguuaagu | ucggcgcgcu | ccgcuucggc | ggcccggggu | 60 |
| ucgccgguuc | ggaucccggg | cgcggaccua | caccacucgu | caggccaugc | uguggcggcg | 120 |
| ucccacauac | aaaauagagg | aagauuggca | cagauguuag | cucagggcca | aucuuccuca | 180 |
| agaaaaaaga | ggaagauugg | caacagaugu | uagcucaggg | cgaaucuucc | ucagc | 235 |

<210> SEQ ID NO 33
<211> LENGTH: 252
<212> TYPE: RNA
<213> ORGANISM: Homo sapiens

<400> SEQUENCE: 33

| | | | | | | |
|---|---|---|---|---|---|---|
| gcagugüggc | gcaguggaua | gagcacggga | ccuggaguca | ggaagaccug | gguucgaauc | 60 |
| ccggcucugc | cacuuacuag | cuguguġacc | uugggcaagu | cacuuaaccu | cucugugccu | 120 |
| caguuuccuc | aucuguaaaa | uggggauaau | aauagcaccu | accacacagg | guuguuguga | 180 |
| ggauuaaaug | agauaauaua | uguaaagcgc | uuagaacagu | gccuggcaca | uaguaagcgc | 240 |
| uauauaaaug | uu | | | | | 252 |

<210> SEQ ID NO 34
<211> LENGTH: 75
<212> TYPE: RNA
<213> ORGANISM: Artificial Sequence
<220> FEATURE:
<223> OTHER INFORMATION: Rodentia - inverted SINE ID (BC1)

<400> SEQUENCE: 34

| | | | | | | |
|---|---|---|---|---|---|---|
| cggagcugag | gaccgaaccc | agggccuugc | gcuugcuagg | caagcgcucu | accacugagc | 60 |
| uaaauccccca | acccc | | | | | 75 |

<210> SEQ ID NO 35
<211> LENGTH: 95
<212> TYPE: RNA
<213> ORGANISM: Brassica

<400> SEQUENCE: 35

| | | | | | | |
|---|---|---|---|---|---|---|
| gucacgggcg | gucuccggaa | ucccagagga | cucgaacccu | ggugccuugg | gauccaguuc | 60 |
| acucuagugu | uaccacuagg | cuauucuguc | ccggc | | | 95 |

```
<210> SEQ ID NO 36
<211> LENGTH: 115
<212> TYPE: RNA
<213> ORGANISM: Oryza

<400> SEQUENCE: 36
cacgaauauu agggaaggac cuaauaucaa auaauuagaa ggggugaggc uucgaaccca        60
ggucggcuag cccaccaccu uguggagcua gccggaagac cccagggcgu uucuc            115

<210> SEQ ID NO 37
<211> LENGTH: 140
<212> TYPE: RNA
<213> ORGANISM: Artificial Sequence
<220> FEATURE:
<223> OTHER INFORMATION: Salmonidae - inverted SmaI

<400> SEQUENCE: 37
gccauuuagc agacgcuuuu auccaaagcg acuuacaguc augugugcau acauuuuac         60 guaugguggu ucccgggaau cgaacccacu acccuggcgu uacaagcgcc augcucuacc       120
aacugagcua cagaaggacc                                                    140

<210> SEQ ID NO 38
<211> LENGTH: 159
<212> TYPE: RNA
<213> ORGANISM: Arabidopsis

<400> SEQUENCE: 38
gaauaucugg aaguucaagc ccaaaggccc uacaucuccu agaggcggga cccacaccag        60
guuaaauuca ucucuuuugg agaagagauc ccucccaacg ugccucgaac ccagcaccuc       120
caccugggag auuuaccacu gggccaacag cacguuggu                              159

<210> SEQ ID NO 39
<211> LENGTH: 171
<212> TYPE: RNA
<213> ORGANISM: Brassica

<400> SEQUENCE: 39
ugauuaacca ggguugacc agccuucgac cagcccacca ccuaggcccg cgccagccu          60 gugccuguac cgguuagggc ccugggcacg ccuccccuc cccgcgaguc gaacagccga        120 ccucccucc ccaaagagga gguaguacca cuggacuacg agguccuggg u                 171

<210> SEQ ID NO 40
<211> LENGTH: 185
<212> TYPE: RNA
<213> ORGANISM: Artificial Sequence
<220> FEATURE:
<223> OTHER INFORMATION: Rodentia - inverted B2

<400> SEQUENCE: 40
aagauuuauu uauuuauuua uuuauuauau guaaguacac guagcuguc uucagacaca         60 ccagaagagg gcaucagauc ucauuacaga ugguugugag ccaccaugug guucuggga        120 auugaacuca ggaccucugg aagagcaguc aggugcucuu aaccacugag ccaucucucc       180
agccc                                                                    185

<210> SEQ ID NO 41
<211> LENGTH: 189
<212> TYPE: RNA
<213> ORGANISM: Artificial Sequence
<220> FEATURE:
```

<223> OTHER INFORMATION: Salmonidae - inverted HpaI

<400> SEQUENCE: 41
accuuuauuu aacuaggcaa gucaguuaag aacaaauucu uauuuucaau gacggccuag     60
gaacagnggg uuaacugccu uguucagggg cagaacgaca gauuuguacc uugucagcuc    120
ggggauuuga acuugcaacc uuucgguuac uaguccaacg cucuaaccac uaggcuaccc    180
ugccgcccc                                                            189

<210> SEQ ID NO 42
<211> LENGTH: 235
<212> TYPE: RNA
<213> ORGANISM: Equus

<400> SEQUENCE: 42
gcugaggaag auucgcccug agcuaacauc uguugccaau cuuccucuuu uuucuugagg     60
aagauuggcc cugagcuaac aucgugcca aucuuccucu auuuguaug ugggacgccg     120 ccacagcaug gccugacgag uggu guaggu ccgcgcccgg gauccgaacc ggcgaacccc   180
gggccgccga agcggagcgc gccgaacuua accacuaggc cacggggcug gcccc         235

<210> SEQ ID NO 43
<211> LENGTH: 252
<212> TYPE: RNA
<213> ORGANISM: Homo sapiens

<400> SEQUENCE: 43
aacauuuaua uagcgcuuac uaugugccag gcacuguucu aagcgcuuua cauauauuau     60
cucauuuaau ccucacaaca acccugugag guaggugcua uuauauccc cauuuuacag    120 augaggaaac ugaggcacag agagguuaag ugacuugccc aaggcacac agcuaguaag    180 uggcagagcc gggauucgaa cccaggucuu ccugacucca ggucccgugc ucuauccacu   240
gcgccacacu gc                                                        252

<210> SEQ ID NO 44
<211> LENGTH: 167
<212> TYPE: RNA
<213> ORGANISM: Mus musculus

<400> SEQUENCE: 44
cagugcuaga ggaggucaga agagggcauu ggaucccca gaacuggagu uauacgguaa      60 ccucgugug guugugaacc accaugugga uggauauuga guccaaaca cuggccugu      120 gcaagagcau ccagugcucu uaagugcuga gccaucucuu uagcucc                  167

<210> SEQ ID NO 45
<211> LENGTH: 107
<212> TYPE: RNA
<213> ORGANISM: Mus musculus

<400> SEQUENCE: 45
gaugccuuag aaguggaguu aagaguugug agcugccguu uuuugguucu gggacucgaa     60
cucguuuccu cugauacuau caaccaccaa gccaucucuu cagcccc                  107

<210> SEQ ID NO 46
<211> LENGTH: 131
<212> TYPE: RNA
<213> ORGANISM: Mus musculus

<400> SEQUENCE: 46

```
gccagaagaa guuguggaau ucccuggaac uggagcaacc aacaguuugu gugcaccaug    60
ugcguaaugg gaaucgaacc ugggucccucu auaagacugg ccagugcucu aacuacuga   120 ggugcauuuc u                                                        131
```

<210> SEQ ID NO 47
<211> LENGTH: 187
<212> TYPE: RNA
<213> ORGANISM: Mus musculus

<400> SEQUENCE: 47

```
uuauuuuaaa uauaugagua uuucaccugc auaggcgcac aguacccaca gagacuagaa    60
gaggguggca gaucuccuga gacuggaguu aaugcuugug agcugccaug uggaugcugg   120
aaaucaaacc cagguccuuu ggaaggcagg caggugcucu aaucaugga agcaucucuu   180 cagcucc                                                             187
```

<210> SEQ ID NO 48
<211> LENGTH: 131
<212> TYPE: RNA
<213> ORGANISM: Mus musculus

<400> SEQUENCE: 48

```
cagcgacauc agaagaggau auuggauccc auuacagaug guugaaggcc accaugucgu    60
ugcugggaau gaacucaaga ccucuggaag agcagucagu gcucuuaacc ucugagccau   120
cucuccagcc c                                                        131
```

<210> SEQ ID NO 49
<211> LENGTH: 114
<212> TYPE: RNA
<213> ORGANISM: Mus musculus

<400> SEQUENCE: 49

```
aucccuucca aagcucaaga ugguuguaag ccacccugug auugcuggga uuugaacuca    60
agaccuccgg aagagcaauu agugcucuua accgcugagc aaucucucca gccc         114
```

<210> SEQ ID NO 50
<211> LENGTH: 357
<212> TYPE: RNA
<213> ORGANISM: Mus musculus

<400> SEQUENCE: 50

```
gugcagugcu agaggagguc agaagagggc auuggauccc ccagaacugg aguuauacgg    60
uaaccucgug gugguuguga accaccaugu ggauggauau ugaguuccaa acacuggucc   120
ugugcaagag cauccagugc ucuuaagugc ugagccaucu cuuuagcucc uuauuuuaaa   180
uauaugagua uuucaccugc auaggcgcac aguacccaca gagacuagaa gaggguggca   240
gaucuccuga gacuggaguu aaugcuugug agcugccaug uggaugcugg aaaucaaacc   300
cagguccuuu ggaaggcagg caggugcucu aaucaugga agcaucucuu cagcucc      357
```

<210> SEQ ID NO 51
<211> LENGTH: 532
<212> TYPE: RNA
<213> ORGANISM: Mus musculus

<400> SEQUENCE: 51

```
gugcagugcu agaggaggc agaagagggc auuggauccc ccagaacugg aguuauacgg    60
```

| | |
|---|---|
| uaaccucgug gugguuguga accaccaugu ggauggauau ugaguuccaa acacuggucc | 120 |
| ugugcaagag cauccagugc ucuuaagugc ugagccaucu cuuuagcucc gugcgaauuc | 180 |
| ggugcagugc uagaggaggu cagaagaggg cauuggaucc cccagaacug gaguuauacg | 240 |
| guaaccucgu gguggguugug aaccaccaug uggauggaua uugaguucca aacacgguc | 300 |
| cugugcaaga gcauccagug cucuuaagug cugagccauc ucuuuagcuc cgugcgaauu | 360 |
| cggugcagug cuagaggagg ucagaagagg gcauuggauc cccagaaacu ggaguuauac | 420 |
| gguaaccucg uggugguugu gaaccaccau guggauggau auugaguucc aaacacuggu | 480 |
| ccugugcaag agcauccagu gcucuuaagu gcugagccau cucuuuagcu cc | 532 |

<210> SEQ ID NO 52
<211> LENGTH: 228
<212> TYPE: RNA
<213> ORGANISM: Mus musculus

<400> SEQUENCE: 52

| | |
|---|---|
| uuuuuuuaaa aauuuauuuu uauuuuaugu guaugagugu uuugccugca uguaugucug | 60 |
| uguaccacgu gcgugccugg ugcccgcgga ggccagaaga gggcgucgga uccccuggaa | 120 |
| cuggaguuac agauggUugu gagccgccau guggugcgcg ggaaucgaac ccggguccuc | 180 |
| uggaagagca gccagugcuc uuaaccgcug agccaucucu ccagcccc | 228 |

<210> SEQ ID NO 53
<211> LENGTH: 214
<212> TYPE: RNA
<213> ORGANISM: Mus musculus

<400> SEQUENCE: 53

| | |
|---|---|
| uuuuuuuuac uuguauaggu guuugccug caugug uauc uaucuaugua ccgaauaugu | 60 |
| uccugguauc cacagagacc aaaaguggau guuguaucuc cugaaauugg agucauagac | 120 |
| aguuaugagc ugccauuuga gugcuuggaa uagaacccag guccucuuaa agagcaucca | 180 |
| gugcucuuaa aaacugagac aucucuguag ccuc | 214 |

<210> SEQ ID NO 54
<211> LENGTH: 200
<212> TYPE: RNA
<213> ORGANISM: Mus musculus

<400> SEQUENCE: 54

| | |
|---|---|
| uuuauuuugc uuuauguguc ugaguguuug cuugaaugua ugucugugua ccacgccugu | 60 |
| accuugugcc uucagaguug agaggagggc auaggaucuc cuggaacugg aauugcaggu | 120 |
| gguugugagc cacccugugg guccggggga ccauaccuca gcaagaacau caugugcucu | 180 |
| uaauuccuga gucuccaacc | 200 |

<210> SEQ ID NO 55
<211> LENGTH: 214
<212> TYPE: RNA
<213> ORGANISM: Mus musculus

<400> SEQUENCE: 55

| | |
|---|---|
| uuuauuuacu uaucuuuaug uguaugagug uguugcagaa cuguuaugu c ugugugucac | 60 |
| augcaugccu gcuguucaug gaguccagaa gagggcaucg gauccccugg aacuggaguu | 120 |
| acagaugagu ggccaugug a auguuaagaa ccaaaccugg guccucugaa agagcagaca | 180 |
| augcucuuaa cuacugagcu gucucuccag cccc | 214 |

<210> SEQ ID NO 56
<211> LENGTH: 205
<212> TYPE: RNA
<213> ORGANISM: Mus musculus

<400> SEQUENCE: 56
uuauuuuauu cguguaagug uuuugccagc aucuaugucu ucgcacuaug ugcaggucug     60
gugccugagg gguccagacg agagcacugg gucuccggga acuggaguua cagaucauug    120
ugagccacca uguggugca gggaaucgaa ccugggaccu cuggaggagc agccacugcu    180
cuuaaccacu acacuauuuc uccag                                          205

<210> SEQ ID NO 57
<211> LENGTH: 121
<212> TYPE: RNA
<213> ORGANISM: Mus musculus

<400> SEQUENCE: 57
ucuguggacc acuguguaca gaagccugag aaggcuagca gaucchcaga acuggaacug     60
ugagacgcug ugcuauggag gugcuaggaa cugaaaaugg auggguccuc ugcaagagca    120
g                                                                    121

<210> SEQ ID NO 58
<211> LENGTH: 191
<212> TYPE: RNA
<213> ORGANISM: Mus musculus

<400> SEQUENCE: 58
uuguuuuaau ugaauggcua uaggguguuu cuucuguaug uauaucuaug uuugguaccu     60
acagaggcau cagauccucu ggaacuguag uugcugacag uugugagcug ucauggggau    120
gcuggaauug aaccuggauc cuaugaaaga acagccagug uucuuaaccg cugagcuauc    180
ucuccaggcc c                                                         191

<210> SEQ ID NO 59
<211> LENGTH: 205
<212> TYPE: RNA
<213> ORGANISM: Mus musculus

<400> SEQUENCE: 59
uuuuuuuuuu aauuuuaaaa aaaaagauuu uauuuauuua uuuuauauau gaugaguaca     60
cugucacucu uuucagacac ccuagaaaag gggggcauca gaucccauua cagaugguug    120
ugagccacau gguugcuggg aauugacccu caggaccucug aaagagcagu cagugcucuc    180
aaccuuugag ucaucucucc agccc                                          205

<210> SEQ ID NO 60
<211> LENGTH: 190
<212> TYPE: RNA
<213> ORGANISM: Mus musculus

<400> SEQUENCE: 60
auguauaucu guaaugggac auacucacau acaugggcac ugagauauaa aaggccagaa     60
gagagcacug gacccucugg aguugagauu cuaagcaguu gugaaccauc ugauguaggu    120
gcugggaacu gaacugggu ccuuugcuag agaaguaugu cucuuaaccau cugagccgua    180 ucuccauccc                                                           190

<210> SEQ ID NO 61
<211> LENGTH: 169
<212> TYPE: RNA
<213> ORGANISM: Mus musculus

<400> SEQUENCE: 61
uaaagauuua uucauuaagu acacuguagc uaucuucaga cgcaucagaa gagggcguca    60
gaucucuuua caggugguug ugagccacca ugugguugcu ggaauuugaa cucaggaccu   120
ucaaaagagc agucaguguu cuuaaccgcu gagccaucuc uccaacccc               169

<210> SEQ ID NO 62
<211> LENGTH: 159
<212> TYPE: RNA
<213> ORGANISM: Mus musculus

<400> SEQUENCE: 62
uuauuuauua uaaguacacu guagcugucu ucagacacaa caaaagaggg cgucagaucu    60
cauuacaggu gguugagcca ccaugugguu gcugggauuu gaacucagga ccuucagaac   120
agucagugcu cuuacccacu gagccagcga gccagcccc                         159

<210> SEQ ID NO 63
<211> LENGTH: 308
<212> TYPE: RNA
<213> ORGANISM: Artificial Sequence
<220> FEATURE:
<223> OTHER INFORMATION: 1-183 SINEUP-GFP polyA

<400> SEQUENCE: 63
cucgagccag ugaacagcuc cucgcccuug cucaccaugg uggcgaccgg uagcgcuagc    60
ggaucugacg guucacuaga ucggccgcc acugugcugg aauuccagug cuagaggagg   120
ucagaagagg gcauuggauc ccccagaacu ggaguuauac gguaaccucg uggugguugu   180
gaaccaccau guggauggau auugaguucc aaacacuggu ccugugcaag agcauccagu   240
gcucuuaagu gcugagccau cucuuuagcu ccaaaaaaaa aaaaaaaaaa aaaaaaaaaa   300
aaaagcuu                                                          308

<210> SEQ ID NO 64
<211> LENGTH: 179
<212> TYPE: RNA
<213> ORGANISM: Artificial Sequence
<220> FEATURE:
<223> OTHER INFORMATION: 59-96 polyA SINEUP-GFP

<400> SEQUENCE: 64
cucgagccag ugaacagcuc cucgcccuug cucaccaugg uggcgaccgg uagcgcuagc    60
ggaucugacg guucacuaga ucggccgcc acugugcugg aauucgguaa ccucguggug   120
guugugaacc accaugugga uggaaaaaaa aaaaaaaaaa aaaaaaaaaa aaaagcuu    179

<210> SEQ ID NO 65
<211> LENGTH: 77
<212> TYPE: RNA
<213> ORGANISM: Artificial Sequence
<220> FEATURE:
<223> OTHER INFORMATION: 44-120 U78G SINEUP

<400> SEQUENCE: 65
gaacuggagu uauacgguaa ccucguggug guugggaacc accaugugga uggauauuga    60
guuccaaaca cuggucc                                                 77

<210> SEQ ID NO 66
<211> LENGTH: 77
<212> TYPE: RNA
<213> ORGANISM: Artificial Sequence
<220> FEATURE:
<223> OTHER INFORMATION: 44-120 GUG77-79CCC SINEUP

<400> SEQUENCE: 66
gaacuggagu uauacgguaa ccucguggug guucccaacc accaugugga uggauauuga    60
guuccaaaca cuggucc                                                  77

<210> SEQ ID NO 67
<211> LENGTH: 77
<212> TYPE: RNA
<213> ORGANISM: Artificial Sequence
<220> FEATURE:
<223> OTHER INFORMATION: 44-120 SINEUP strong

<400> SEQUENCE: 67
ggaccggagu uauacgguaa ccgcguggug guugugaacc accacgcgga uggauauuga    60
guuccaaaca ccggucc                                                  77

<210> SEQ ID NO 68
<211> LENGTH: 77
<212> TYPE: RNA
<213> ORGANISM: Artificial Sequence
<220> FEATURE:
<223> OTHER INFORMATION: 44-120 SINEUP weak

<400> SEQUENCE: 68
gaacuagagu uauacgguaa ccacauggug guugugaacc accaugugga uggauauuga    60
guuccaaaca cuaguuc                                                  77

<210> SEQ ID NO 69
<211> LENGTH: 206
<212> TYPE: RNA
<213> ORGANISM: Artificial Sequence
<220> FEATURE:
<223> OTHER INFORMATION: SINEUP 071 and miniSINEUP 071 effector domain

<400> SEQUENCE: 69
uuauuuuaaa uauaugagua uuucaccugc auaggcgcac aguacccaca gagacuagaa    60
gaggguagua gaucccuag aacuggaguu uauacgguaac cucguggugg uugugagcua   120 ccaugugggau ggauacuggg aaucaaaccc agguccugug gaaggcaggc aggugcucuc   180
aagcacugag ccaucucuuc agcucc                                        206

<210> SEQ ID NO 70
<211> LENGTH: 206
<212> TYPE: RNA
<213> ORGANISM: Artificial Sequence
<220> FEATURE:
<223> OTHER INFORMATION: SINEUP 072 and miniSINEUP 072 effector domain

<400> SEQUENCE: 70
uuauuuuaaa uauaugagua uuucaccugc auaggcgcac agugcucaag gagaucagaa    60
gagggcauca gaucuccuga gacuggaguu uauacgguaac cucgugaugg uugugaacua   120 ccaugugggau ggauauugag uuccaaacac agguccugug caagagcagc aggugcucuu   180
aagcacggaa ccaucucuuu agcucc                                        206

<210> SEQ ID NO 71
<211> LENGTH: 156
<212> TYPE: RNA
<213> ORGANISM: Artificial Sequence
<220> FEATURE:
<223> OTHER INFORMATION: SINEUP 073 and miniSINEUP 073 effector domain

<400> SEQUENCE: 71

```
gaggcuagaa gagggugauca gaucccuga gacuggaguu auacgguaac cucgugugg      60 uugugagcca ccauguggau ggauacugag aaccaaaccc uguccugug caagagcauc     120 aggugcucuu aagcacggaa ccaucucuuc agcucc                              156
```

<210> SEQ ID NO 72
<211> LENGTH: 68
<212> TYPE: RNA
<213> ORGANISM: Artificial Sequence
<220> FEATURE:
<223> OTHER INFORMATION: SINEUP 074 and miniSINEUP 074 effector domain

<400> SEQUENCE: 72

```
guccugugca agagcaucga acucggugcu cuuaagcaca gaagccacca agccaucucu      60
ucagcccc                                                              68
```

<210> SEQ ID NO 73
<211> LENGTH: 110
<212> TYPE: RNA
<213> ORGANISM: Artificial Sequence
<220> FEATURE:
<223> OTHER INFORMATION: SINEUP 075 and miniSINEUP 075 effector domain

<400> SEQUENCE: 73

```
cagugcuaga ggaggucaga agagggcauc ccccagccuc gugugguug ugaaccacca       60 uguggcugug caagagcaug cucuuaagug cugagccauc ucuuuagcuc                110
```

<210> SEQ ID NO 74
<211> LENGTH: 126
<212> TYPE: RNA
<213> ORGANISM: Artificial Sequence
<220> FEATURE:
<223> OTHER INFORMATION: 24-150 effector domain

<400> SEQUENCE: 74

```
gagggcauug gaucccccag aacuggaguu auacgguaac cucguggugg uugugaacca      60
ccauguggau ggauauugag uuccaaacac uguccugug caagagcauc cagugcucuu     120
aagugc                                                              126
```

<210> SEQ ID NO 75
<211> LENGTH: 89
<212> TYPE: RNA
<213> ORGANISM: Artificial Sequence
<220> FEATURE:
<223> OTHER INFORMATION: C_34-122 effector domain

<400> SEQUENCE: 75

```
ggaucccca gaacuggagu uauacgguaa ccucguggug guugugaacc accauggga       60 uggauauuga guuccaaaca cugguccug                                      89
```

<210> SEQ ID NO 76
<211> LENGTH: 72
<212> TYPE: RNA
<213> ORGANISM: Artificial Sequence

```
<220> FEATURE:
<223> OTHER INFORMATION: TM effector domain

<400> SEQUENCE: 76
ugcuagagga ggucagaaga gggcauugga ugcaaaucca gugcucuuaa gugcugagcc    60
aucucuuuag cu                                                       72

<210> SEQ ID NO 77
<211> LENGTH: 94
<212> TYPE: RNA
<213> ORGANISM: Artificial Sequence
<220> FEATURE:
<223> OTHER INFORMATION: MC2 effector domain

<400> SEQUENCE: 77
gagggcauug gauccccag aacuggaguu auacgguaac gauggauauu gaguuccaaa     60
cacugguccu gugcaagagc auccagugcu cuua                                94

<210> SEQ ID NO 78
<211> LENGTH: 137
<212> TYPE: RNA
<213> ORGANISM: Artificial Sequence
<220> FEATURE:
<223> OTHER INFORMATION: Figure 3 panel B, "fragment number 1"

<400> SEQUENCE: 78
gucagaagag ggcauuggau cccccagaac uggaguuaua cgguaaccuc guggugguug    60
ugaaccacca gugggaugga uauugaguuc caaacacugg uccugugcaa gagcauccag   120
ugcucuuaag ugcugac                                                  137

<210> SEQ ID NO 79
<211> LENGTH: 112
<212> TYPE: RNA
<213> ORGANISM: Artificial Sequence
<220> FEATURE:
<223> OTHER INFORMATION: Figure 3 panel B, "fragment number 2"

<400> SEQUENCE: 79
gcauuggauc cccagaacu ggaguuauac gguaaccucg ugguguugu gaaccaccau      60 guggauggau auugaguucc aaacacuggu ccugugcaag agcauccagu gc           112

<210> SEQ ID NO 80
<211> LENGTH: 69
<212> TYPE: RNA
<213> ORGANISM: Artificial Sequence
<220> FEATURE:
<223> OTHER INFORMATION: Figure 3 panel B, "fragment number 4"

<400> SEQUENCE: 80
gaacuggagu uauacgguaa ccucguggug guugugaacc accaugugga uggauauuga    60
guuccaaac                                                            69

<210> SEQ ID NO 81
<211> LENGTH: 24
<212> TYPE: RNA
<213> ORGANISM: Artificial Sequence
<220> FEATURE:
<223> OTHER INFORMATION: Figure 6 panel A

<400> SEQUENCE: 81
ucgugguggu ugugaaccac caug                                           24
```

Figure 16:
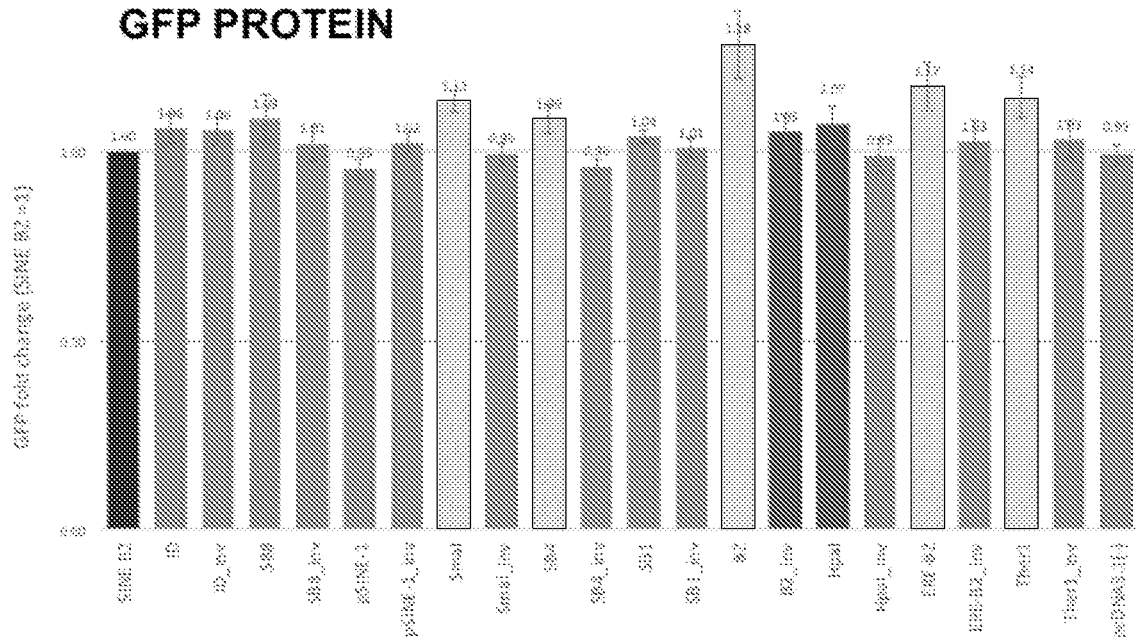
FIG. 16 related to Example 16 shows SINE sequences from evolutionary distant species acting as effector domain in antisense functional nucleic acid molecules with translation up-regulation activity (Western blot and qRT-PCR). The sequence with SINE name ID is SEQ ID NO:82. The sequence with SINE name SB8 is SEQ ID NO:83. The sequence with SINE name p-SINE1 is SEQ ID NO:84. The sequence with SINE name Smal is SEQ ID NO:85. The sequence with SINE name SB4 is SEQ ID NO:86. The sequence with SINE name SB1 is SEQ ID NO:87. The sequence with SINE name B2 is SEQ ID NO:88. The sequence with SINE name Hpal is SEQ ID NO:89. The sequence with SINE name ERE-B2 is SEQ ID NO:90. The sequence with SINE name Ther-1 is SEQ ID NO:91.
Figure 16:
Figure 16:
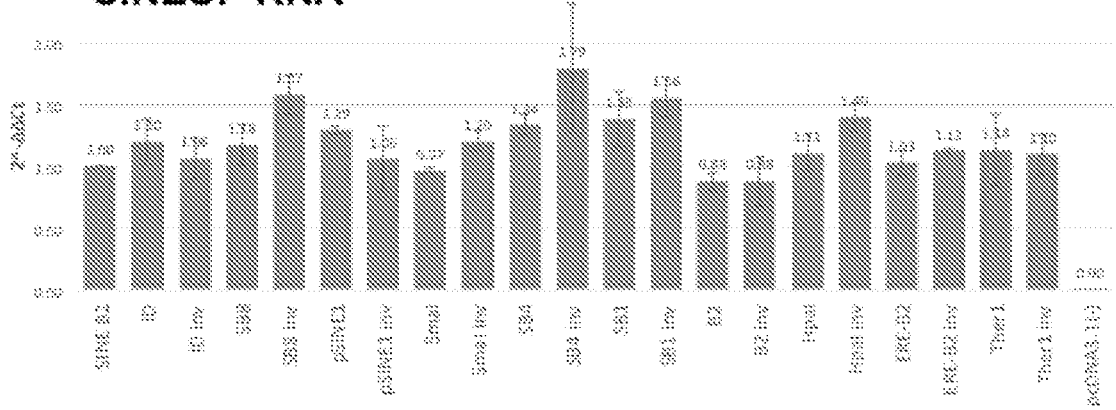

<210> SEQ ID NO 82
<211> LENGTH: 75
<212> TYPE: DNA
<213> ORGANISM: Artificial Sequence
<220> FEATURE:
<223> OTHER INFORMATION: Figure 16 "ID"

<400> SEQUENCE: 82

```
ggggttgggg atttagctca gtggtagagc gcttgcctag caagcgcaag gccctgggtt     60
cggtcctcag ctccg                                                      75
```

<210> SEQ ID NO 83
<211> LENGTH: 95
<212> TYPE: DNA
<213> ORGANISM: Artificial Sequence
<220> FEATURE:
<223> OTHER INFORMATION: Figure 16 "SB8"

<400> SEQUENCE: 83

```
gccgggacag aatagcctag tggtaacact agagtgaact ggatcccaag gcacctgggt     60
tcgagtcctc tgggattccg agaccgccc gtgac                                 95
```

<210> SEQ ID NO 84
<211> LENGTH: 115
<212> TYPE: DNA
<213> ORGANISM: Artificial Sequence
<220> FEATURE:
<223> OTHER INFORMATION: Figure 16 "p-SINE1"

<400> SEQUENCE: 84

```
gagaaacgcc ctggggtctt ccggctagct ccacaaggtg gtgggctagc cgacctgggt     60
tcgaagcctc accccttcta attatttgat attaggtcct tccctaatat tcgtg          115
```

<210> SEQ ID NO 85
<211> LENGTH: 140
<212> TYPE: DNA
<213> ORGANISM: Artificial Sequence
<220> FEATURE:
<223> OTHER INFORMATION: Figure 16 "SmaI"

<400> SEQUENCE: 85

```
ggtccttctg tagctcagtt ggtagagcat ggcgcttgta acgccagggt agtgggttcg     60
attcccggga ccacccatac gtaaaaatgt atgcacacat gactgtaagt cgctttggat    120
aaaagcgtct gctaaatggc                                                140
```

<210> SEQ ID NO 86
<211> LENGTH: 159
<212> TYPE: DNA
<213> ORGANISM: Artificial Sequence
<220> FEATURE:
<223> OTHER INFORMATION: Figure 16 "SB4"

<400> SEQUENCE: 86

```
accaacgtgc tgttggccca gtggtaaatc tcccaggtgg aggtgctggg ttcgaggcac     60
gttgggaggg atctcttctc caaaagagat gaatttaacc tggtgtgggt cccgcctcta    120
ggagatgtag ggcctttggg cttgaacttc cagatattc                           159
```

<210> SEQ ID NO 87
<211> LENGTH: 171
<212> TYPE: DNA
<213> ORGANISM: Artificial Sequence

```
<220> FEATURE:
<223> OTHER INFORMATION: Figure 16 "SB1"

<400> SEQUENCE: 87
acccaggacc tcgtagtcca gtggtactac ctcctctttg gggaggggag gtcggctgtt        60
cgactcgcgg ggaggggagg gcgtgcccag ggccctaacc ggtacaggca caggctggcg       120
ccgggcctag gtggtgggct ggtcgaaggc tggtcaacac ctggttaatc a                171

<210> SEQ ID NO 88
<211> LENGTH: 185
<212> TYPE: DNA
<213> ORGANISM: Artificial Sequence
<220> FEATURE:
<223> OTHER INFORMATION: Figure 16 "B2"

<400> SEQUENCE: 88
gggctggaga gatggctcag tggttaagag cacctgactg ctcttccaga ggtcctgagt        60
tcaattccca gcaaccacat ggtggctcac aaccatctgt aatgagatct gatgccctct       120
tctggtgtgt ctgaagacag ctacagtgta cttacatata ataaataaat aaataaataa       180
atctt                                                                   185

<210> SEQ ID NO 89
<211> LENGTH: 189
<212> TYPE: DNA
<213> ORGANISM: Artificial Sequence
<220> FEATURE:
<223> OTHER INFORMATION: Figure 16 "Hpa1"

<400> SEQUENCE: 89
ggggcggcag ggtagcctag tggttagagc gttggactag taaccgaaag gttgcaagtt        60
caaatccccg agctgacaag gtacaaatct gtcgttctgc ccctgaacaa ggcagttaac       120
ccactgttcc taggccgtca ttgaaaataa gaatttgttc ttaactgact tgcctagtta       180
aataaaggt                                                               189

<210> SEQ ID NO 90
<211> LENGTH: 235
<212> TYPE: DNA
<213> ORGANISM: Artificial Sequence
<220> FEATURE:
<223> OTHER INFORMATION: Figure 16 "ERE-B2"

<400> SEQUENCE: 90
ggggccagcc ccgtggccta gtggttaagt tcggcgcgct ccgcttcggc ggcccggggt        60
tcgccggttc ggatcccggg cgcggaccta caccactcgt caggccatgc tgtggcggcg       120
tcccacatac aaaatagagg aagattggca cagatgttag ctcagggcca atcttcctca       180
agaaaaaaga ggaagattgg caacagatgt tagctcaggg cgaatcttcc tcagc           235

<210> SEQ ID NO 91
<211> LENGTH: 252
<212> TYPE: DNA
<213> ORGANISM: Artificial Sequence
<220> FEATURE:
<223> OTHER INFORMATION: Figure 16 "Ther-1"

<400> SEQUENCE: 91
gcagtgtggc gcagtggata gagcacggga cctggagtca ggaagacctg ggttcgaatc        60
ccggctctgc cacttactag ctgtgtgacc ttgggcaagt cacttaacct ctctgtgcct       120
```
cagtttcctc atctgtaaaa tggggataat aatagcacct acctcacagg gttgttgtga    180
ggattaaatg agataatata tgtaaagcgc ttagaacagt gcctggcaca tagtaagcgc    240
tatataaatg tt                                                        252

<210> SEQ ID NO 92
<211> LENGTH: 144
<212> TYPE: RNA
<213> ORGANISM: Artificial Sequence
<220> FEATURE:
<223> OTHER INFORMATION: Figure 18 panel C

<400> SEQUENCE: 92
gguccuucug uagcucaguu gguagagcau ggcgcuugua acgccagggu aguggguucg    60
auucccggga ccacccauac guaaaaaugu augcacacau gacuguaagu cgcuuuggau   120
aaaagcgucu gcuaaauggc auau                                          144

<210> SEQ ID NO 93
<211> LENGTH: 169
<212> TYPE: RNA
<213> ORGANISM: Artificial Sequence
<220> FEATURE:
<223> OTHER INFORMATION: Figure 40 panel A "FL"; Figure 40 panel C;
      Figure 41 panel A "FL"; Figure 48 panel B "AS Uchl1 SINEB2"

<400> SEQUENCE: 93
ggcagugcua gaggagguca aagagggca uuggauccccc cagaacugga guuauacggu    60
aaccucgugg ugguugugaa ccaccaugug gauggauauu gaguuccaaa cacugguccu   120
gugcaagagc auccagugcu cuuaagugcu gagccaucuc uuuagcucc                169

<210> SEQ ID NO 94
<211> LENGTH: 75
<212> TYPE: RNA
<213> ORGANISM: Artificial Sequence
<220> FEATURE:
<223> OTHER INFORMATION: Figure 40 panel A "TM"; Figure 48 panel B "TM"

<400> SEQUENCE: 94
gggugcuaga ggaggucaga agagggcauu ggaugcaaau ccagugcucu uaagugcuga    60
gccaucucuu uagcu                                                     75

<210> SEQ ID NO 95
<211> LENGTH: 129
<212> TYPE: RNA
<213> ORGANISM: Artificial Sequence
<220> FEATURE:
<223> OTHER INFORMATION: Figure 48 panel B "24 - 150"

<400> SEQUENCE: 95
ggagagggca uuggaucccc cagaacugga guuauacggu aaccucgugg ugguugugaa    60
ccaccaugug gauggauauu gaguuccaaa cacugguccu gugcaagagc auccagugcu   120
cuuaagugc                                                            129

```
<210> SEQ ID NO 96
<211> LENGTH: 96
<212> TYPE: RNA
<213> ORGANISM: Artificial Sequence
<220> FEATURE:
<223> OTHER INFORMATION: Figure 48 panel B "MC2"

<400> SEQUENCE: 96
gggagggcau uggauccccc agaacuggag uuauacggua acgauggaua uugaguucca        60
aacacugguc cugugcaaga gcauccagug cucuua                                  96
```

The invention claimed is:

1. A functional nucleic acid molecule comprising:
   a target binding sequence comprising a sequence reverse complementary to a target mRNA sequence for which protein translation is to be enhanced; and
   a regulatory sequence having a two-dimensional structure comprising a first stem-loop domain (SL-1) comprising a stem with 8 to 12 paired nucleotides and a loop comprising 5 to 9 nucleotides, wherein the regulatory sequence consists of a sequence having at least 90% identity with a sequence selected from the group consisting of SEQ ID NO:7, SEQ ID NO: 12 and SEQ ID NO: 1.

2. The functional nucleic acid molecule according to claim 1, wherein the stem of the first stem-loop domain (SL-1) has an A-type helical three-dimensional structure.

3. The functional nucleic acid molecule according to claim 1, wherein the two-dimensional structure of the regulatory sequence further comprises a second stem-loop domain (SL-2) and a fourth internal loop domain (IL-4) or a fourth stem-loop domain (SL-4), the second stem-loop domain (SL-2) comprising a stem with 2 to 4 paired nucleotides and a loop comprising 6 to 10 nucleotides, the fourth internal loop domain (IL-4) comprising 14 to 24 nucleotides, and the fourth stem-loop domain (SL-4) comprising a stem with 3 to 5 paired nucleotides and a loop comprising 6 to 10 nucleotides.

4. The functional nucleic acid molecule according to claim 3, further comprising a third internal loop domain (IL-3) comprising 6 to 14 nucleotides, a third stem-loop domain (SL-3) comprising a stem with 1 to 3 paired nucleotides and a loop comprising 3 to 5 nucleotides, a second internal loop domain (IL-2) comprising 6 to 12 nucleotides, and a first internal loop domain (IL-1) comprising 6 to 12 nucleotides.

5. The functional nucleic acid molecule according to claim 1, wherein the regulatory sequence comprises a sequence having at least 90% identity with SEQ ID NO:2.

6. The functional nucleic acid molecule according to claim 1, wherein the molecule is circular.

7. A composition comprising a functional nucleic acid molecule according to claim 1.

8. The functional nucleic acid molecule according to claim 1, wherein the regulatory sequence has protein translation enhancing efficiency.

* * * * *